United States Patent
Becker et al.

(10) Patent No.: US 10,689,363 B2
(45) Date of Patent: *Jun. 23, 2020

(54) CRYSTALLINE FORMS OF 1-(4-{[6-AMINO-5-(4-PHENOXY-PHENYL)-PYRIMIDIN-4-YLAMINO]-METHYL}-PIPERIDIN-1-YL)-PROPENONE

(71) Applicant: Merck Patent GmbH, Darmstadt (DE)

(72) Inventors: Axel Becker, Seeheim-Jugenheim (DE); Marco Poma, Rome (IT); Edoardo Burini, Guidonia Montecelio (IT); Christoph Saal, Otzberg (DE); Vedad Theuerkorn, Pfungstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/578,676

(22) Filed: Sep. 23, 2019

(65) Prior Publication Data

US 2020/0017464 A1    Jan. 16, 2020

Related U.S. Application Data

(63) Continuation of application No. 15/902,482, filed on Feb. 22, 2018, now Pat. No. 10,464,923.

(60) Provisional application No. 62/463,913, filed on Feb. 27, 2017, provisional application No. 62/528,238, filed on Jul. 3, 2017.

(51) Int. Cl.
| | | |
|---|---|---|
| *C07D 401/12* | (2006.01) | |
| *A61P 35/00* | (2006.01) | |
| *A61P 35/02* | (2006.01) | |
| *C07D 403/12* | (2006.01) | |

(52) U.S. Cl.
CPC ............ *C07D 401/12* (2013.01); *A61P 35/00* (2018.01); *A61P 35/02* (2018.01); *C07D 403/12* (2013.01); *C07B 2200/13* (2013.01)

(58) Field of Classification Search
CPC .................................................. C07D 401/12
See application file for complete search history.

(56) References Cited

U.S. PATENT DOCUMENTS 10,464,923 B2 * 11/2019 Becker ................... A61P 35/02

FOREIGN PATENT DOCUMENTS

WO    2012/170976    12/2012

OTHER PUBLICATIONS

Berge et al., J. Pharmaceutical Sciences, 1977, 66(1):1-19.
Caira, M., Topics in Current Chemistry, 1998, 198: 163-208.
Ellmeier et al., J. Exp. Med. 2000, 192(11):1611-1623.
Feldhahn et al., J. Exp. Med., 2005, 201(11):1837-1852.
Horwood et al., J Exp Med, 2003, 197(12):1603-1611.
Hunter T., Cell, 1987, 50(5):823-829.
Islam and Smith, Immunol. Rev., 2000, 178:49-63.
Iwaki et al., J. Biol. Chem., 2005, 280(48):40261-40270.
Jansson and Holmdahl, Clin. Exp. Immunol., 1993, 94:459-465.
Kawakami et al., Journal of Leukocyte Biology, 1999, 65:286-290.
Khan et al., Immunity, 1995, 3:283-299.
Lindvall et al., Immunol. Rev., 2005, 203:200-215.
Montalban et al., "Placebo-Controlled Trial of an Oral BTK Inhibitor in Multiple Sclerosis," The New England Journal of Medicine, May 10, 2019, 12 pages DOI: 10.1056/NEJMoa1901981.
Musumeci et al. Expert Opinion on Therapeutic Patents, vol. 27, No. 12, 1305-1318. (Year: 2017).
"Phase IIb Study of Evobrutinib in Subjects With Rheumatoid Arthritis," NIH U.S. National Library of Medicine, ClinicalTrials. gov, Jun. 24, 2019, 6 pages.
Pan et al., Chem. Med Chem., 2007, 2:58-61.
Rastetter et al., Annu Rev Med, 2004, 55:477-503.
Rosen et al., New Eng. J. Med., 1995, 333(7):431-440.
Serajuddin, A., Advanced Drug Delivery Reviews, 2007, 59:603-616.
Vassilev et al., J. Biol. Chem., 1999, 274(3):1646-1656.
Vihinen et al., Frontiers in Bioscience, 2000, 5:d917-928.
Wallace et al., "Phase 2, Randomized, Double-Blind, Placebo-Controlled, Dose-Finding Study, Evaluating the Bruton'S Tyrosine Kinase Inhibitor Evobrutinib in Patients With Systemic Lupus Erythematosus; Study Design," Lupus Science & Medicine 2019; 6(Suppl 1): A1-A227, 2 pages.

* cited by examiner

*Primary Examiner* — Emily A Bernhardt
(74) *Attorney, Agent, or Firm* — Grüneberg and Myers PLLC

(57) ABSTRACT

A solid form of 1-(4-{[6-Amino-5-(4-phenoxy-phenyl)-pyrimidin-4-ylamino]-methyl}-piperidin-1-yl)-propenone, or pharmaceutically acceptable salts thereof, are useful as BTK inhibitors.

6 Claims, 24 Drawing Sheets

Figure 1: Form A2 Powder X-ray diffractogram
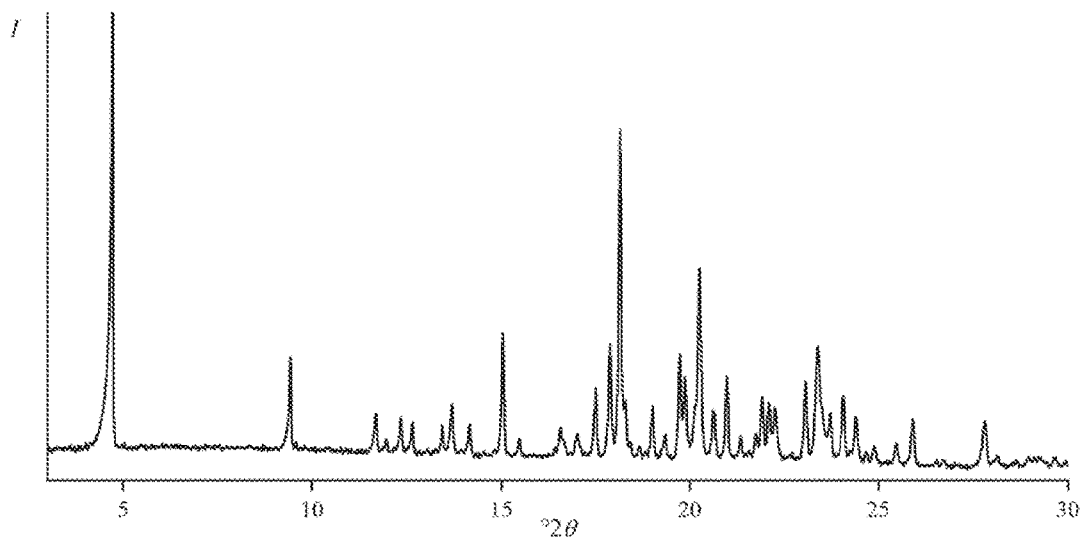
Figure 2: Single Crystal Structure of Free Base Form A2 Viewed Approximately Along A-Axis
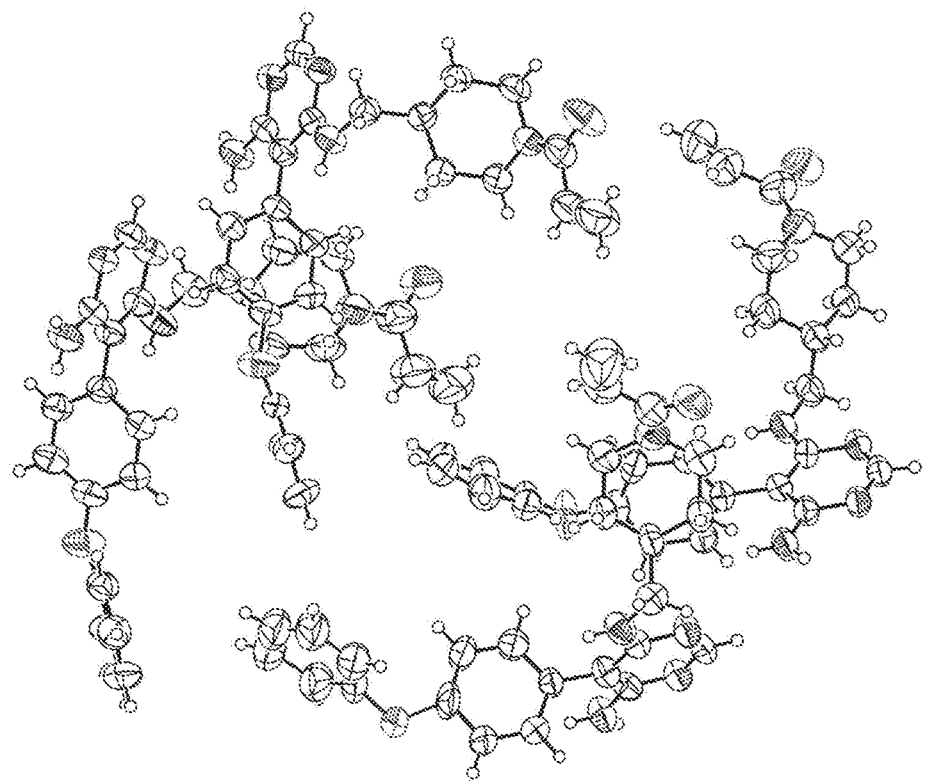

Figure 3: DSC scan of free base form A2 (50 K/min)
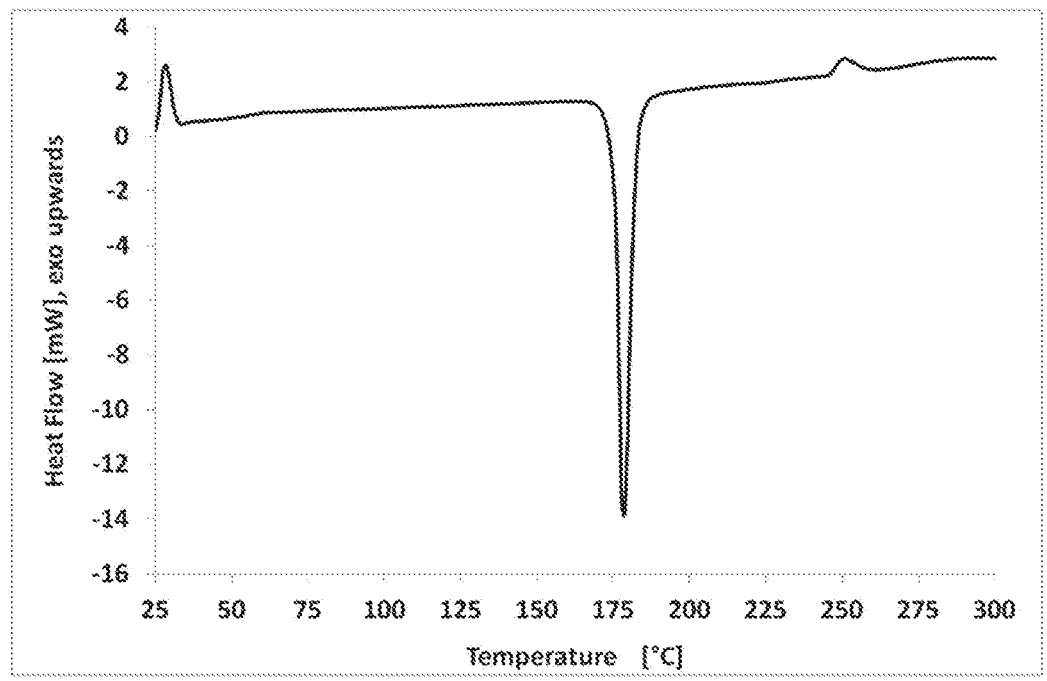
Figure 4: TGA scan of free base form A2 (5 K/min)
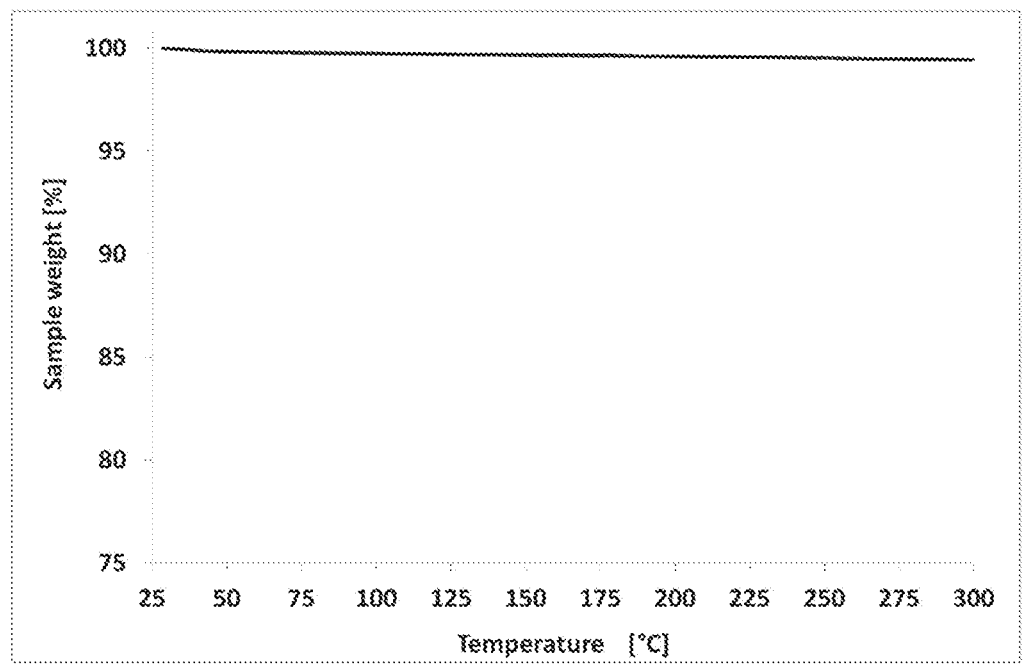

Figure 5: Water Vapour Sorption Isotherm (25 °C) of free base form A2
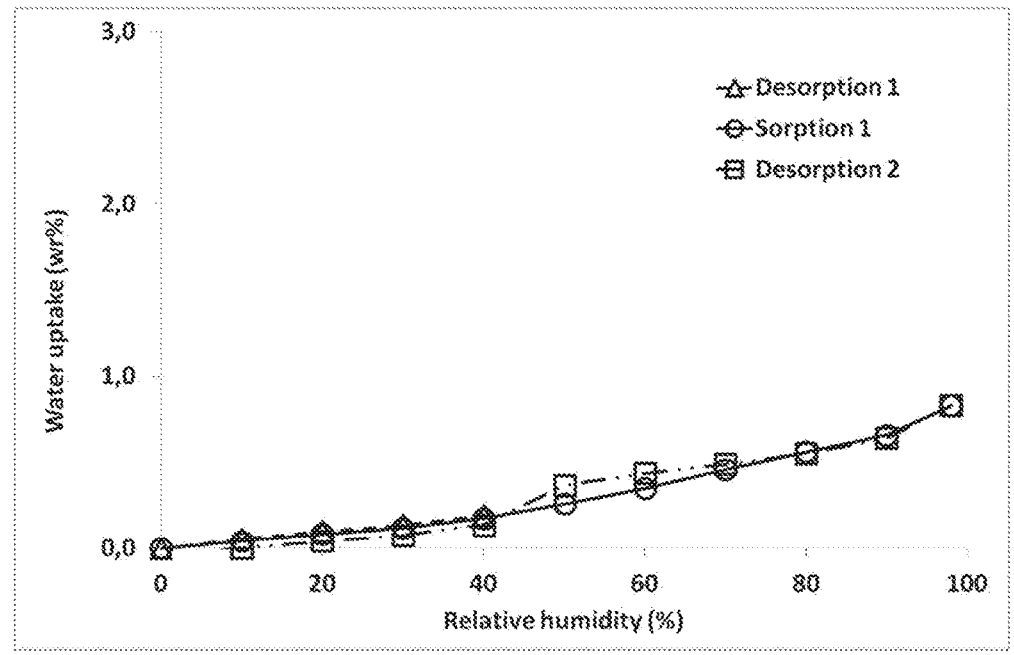
Figure 6: Powder X-ray diffractogram of free base form NF4. The broad peak at 5.5° 2θ is due to the sample holder
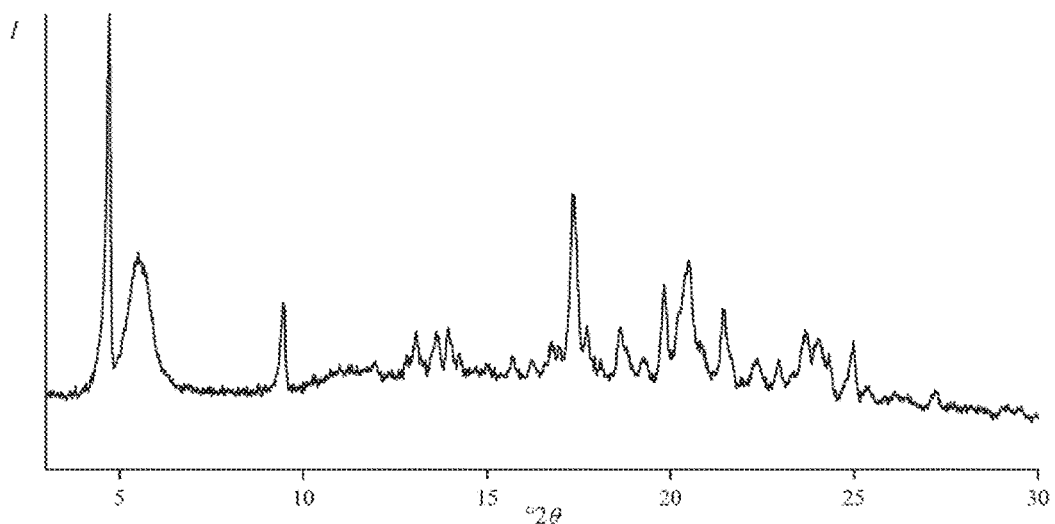

Figure 7: DSC scan of free base form NF4 (50 K/min)
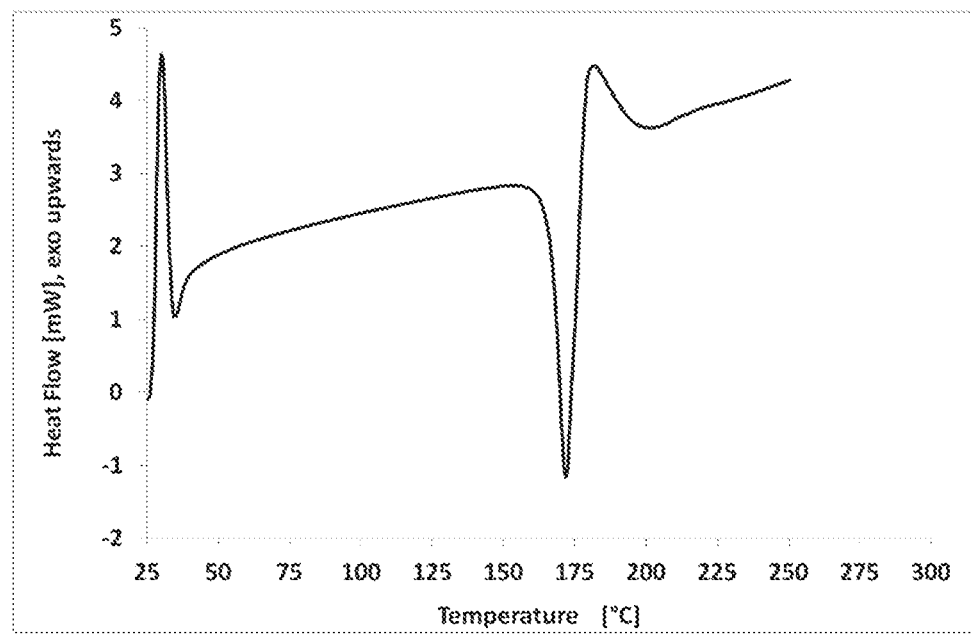
Figure 8: TGA scan of free base form NF4 (5 K/min)
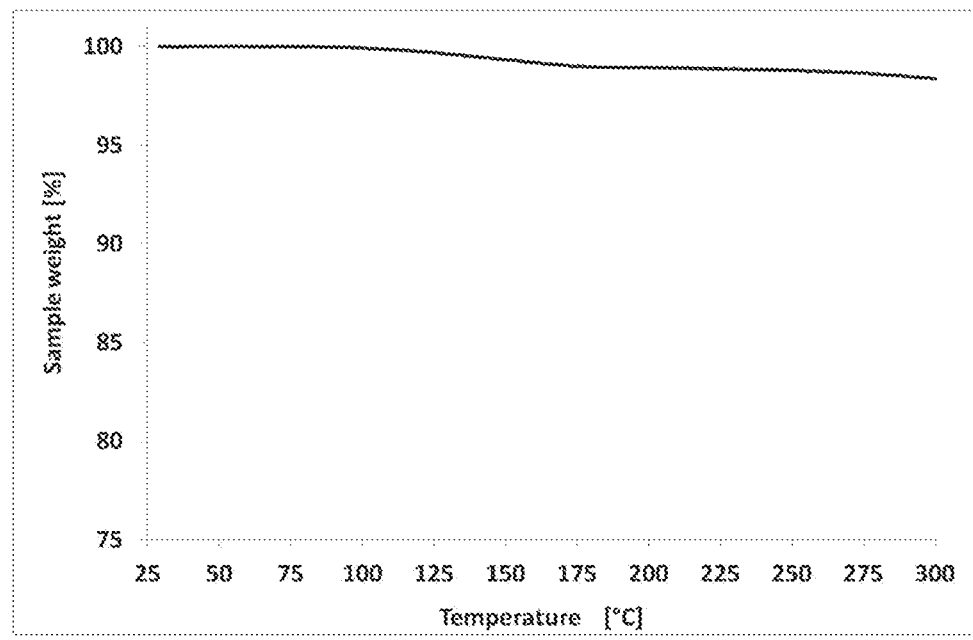

Figure 9: Powder X-ray diffractogram of free base form NF5. The broad peak at 5.5° 2θ is due to the sample holder
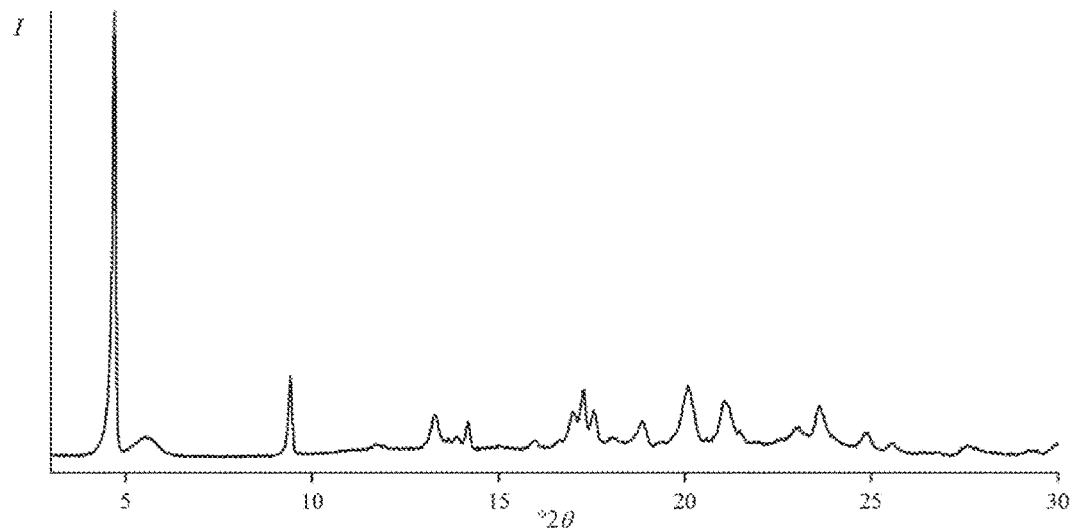
Figure 10: DSC scan of free base form NF5 (50 K/min)
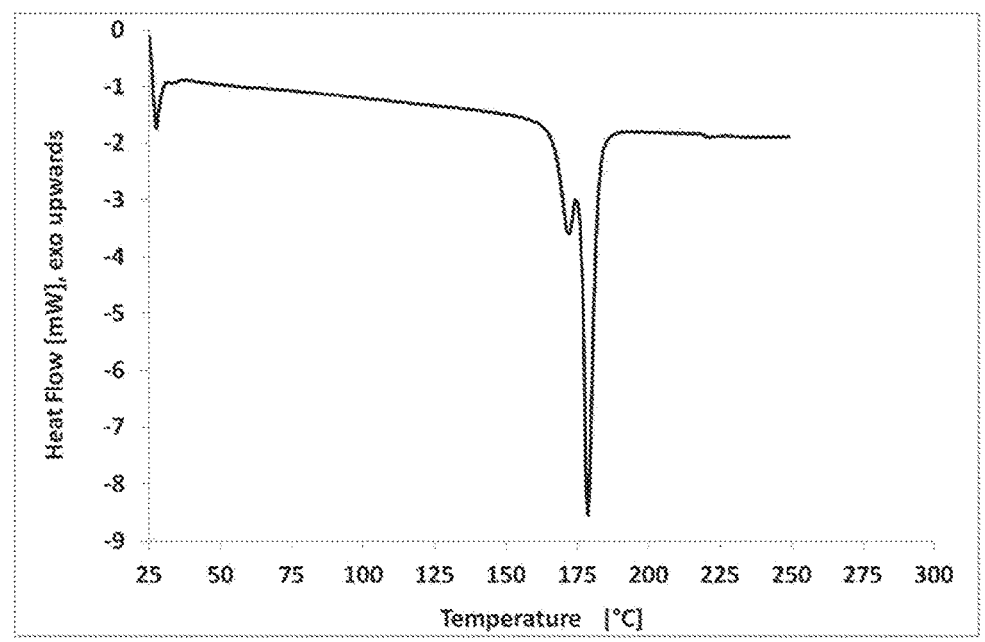

Figure 11: TGA scan of free base form NF5 (5 K/min)
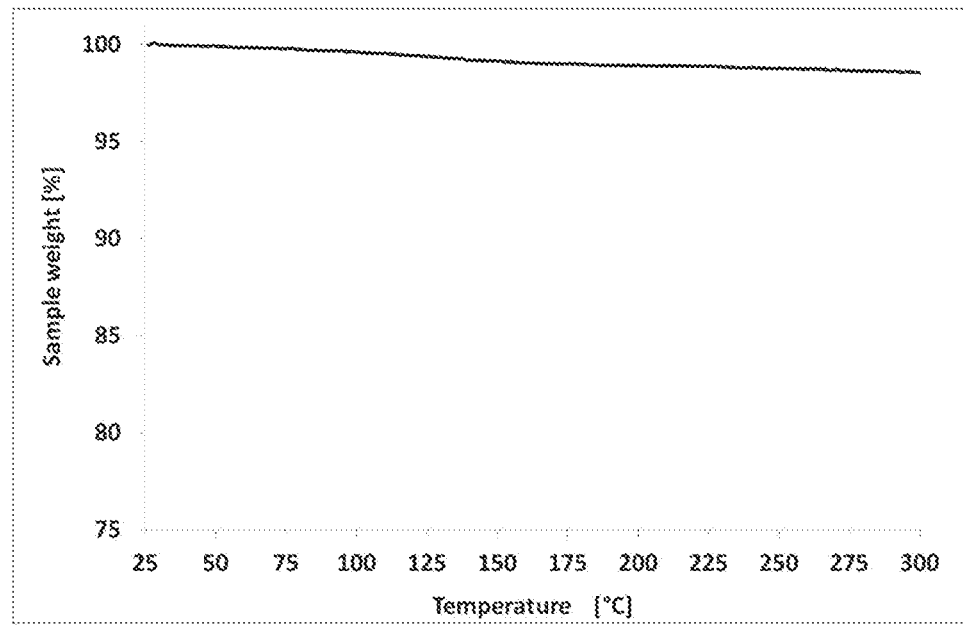
Figure 12: Water Vapour Sorption Isotherm (25 °C) of free base form NF5
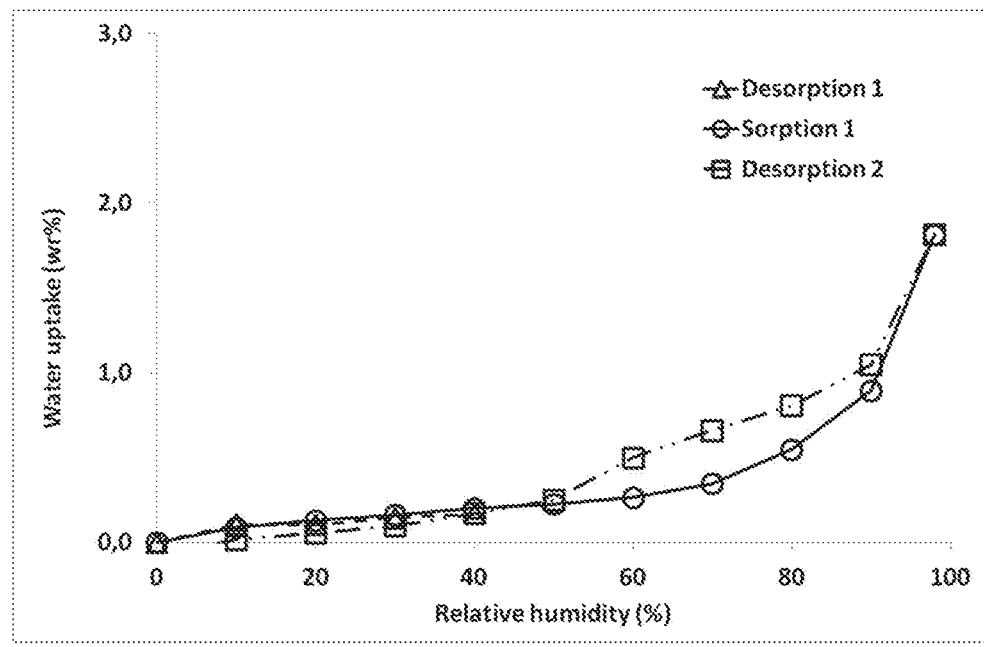

Figure 13: Powder X-ray diffractogram of free base form NF6
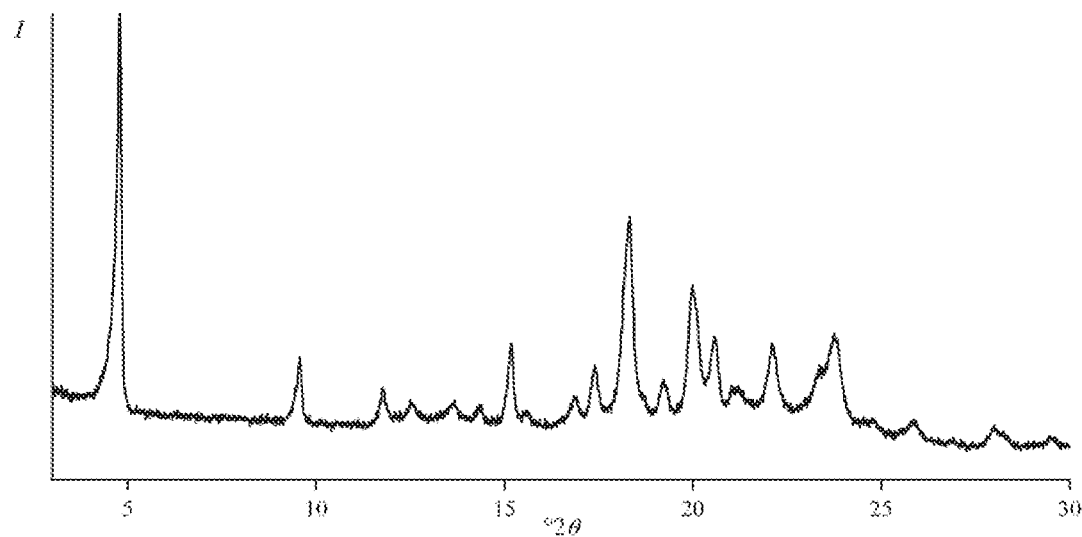
Figure 14: DSC scan of free base form NF6 (50 K/min)
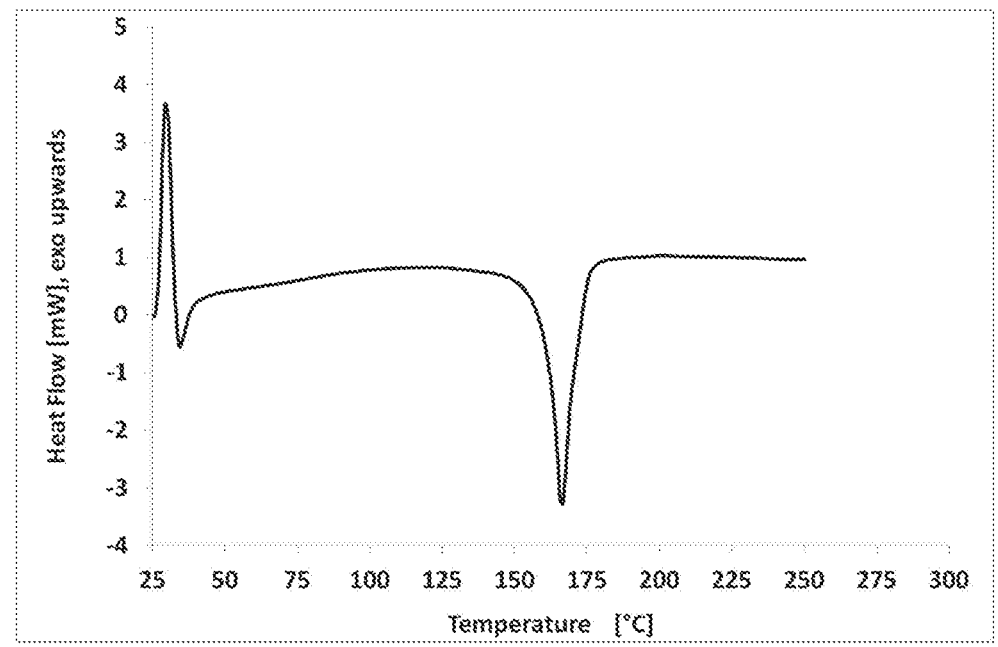

Figure 15: TGA scan of free base form NF6 (5 K/min)
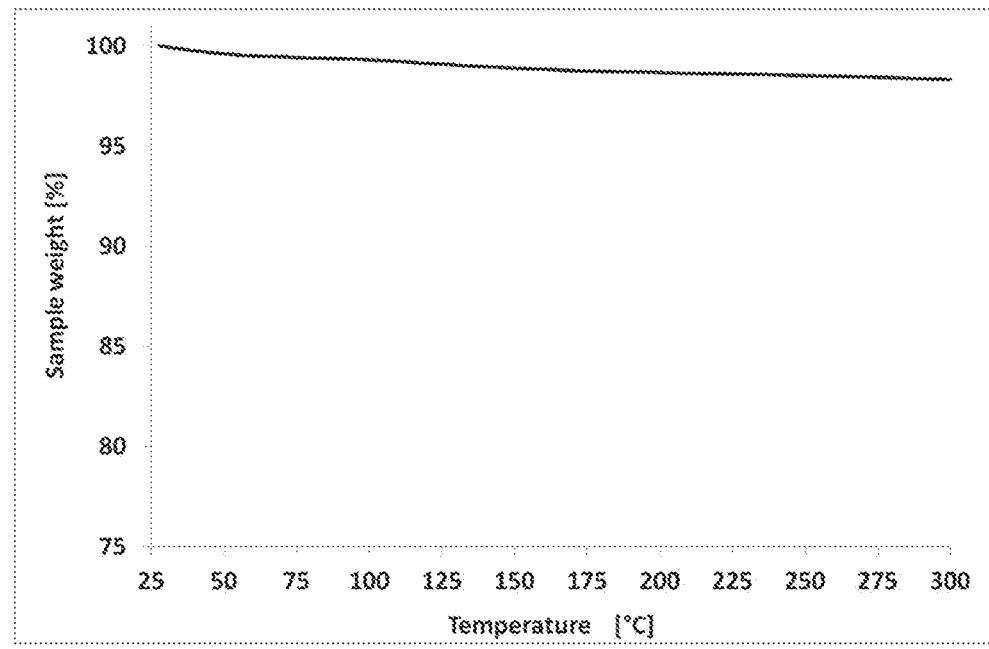
Figure 16: Water Vapour Sorption Isotherm (25 °C) of free base form NF6
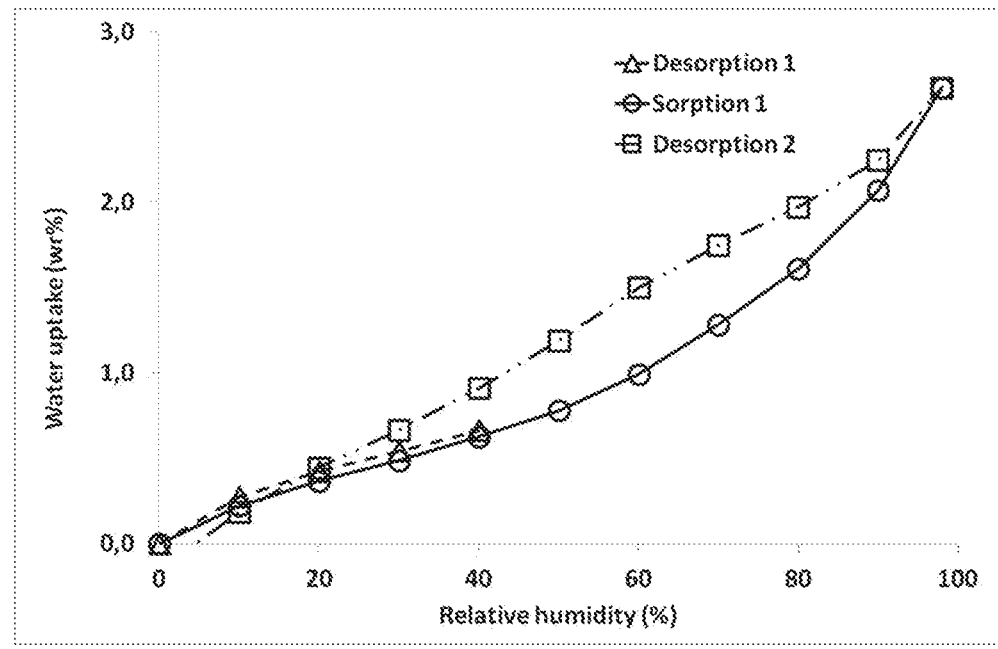

Figure 17: Powder X-ray diffractogram of Malonate salt form Malonate-NF1
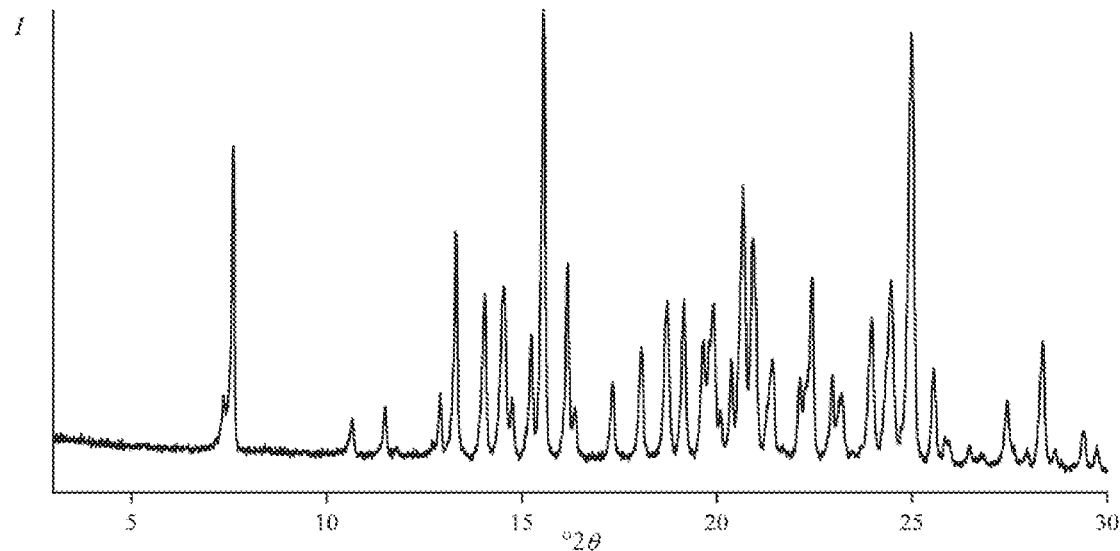
Figure 18: DSC scan of form Malonate-NF1 (5 K/min)
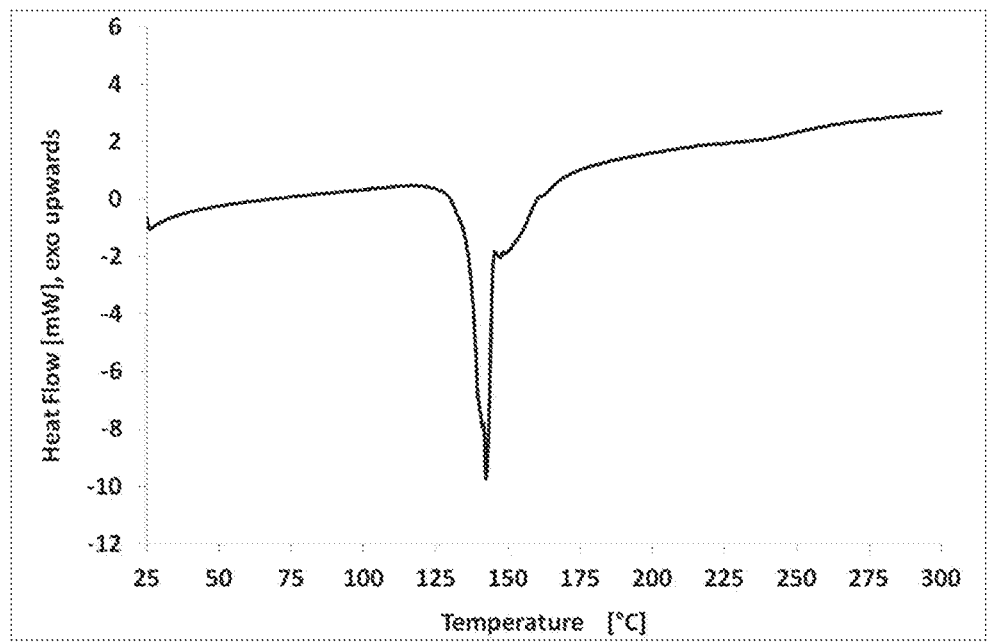

Figure 19: TGA scan of form Malonate-NF1 (5 K/min)
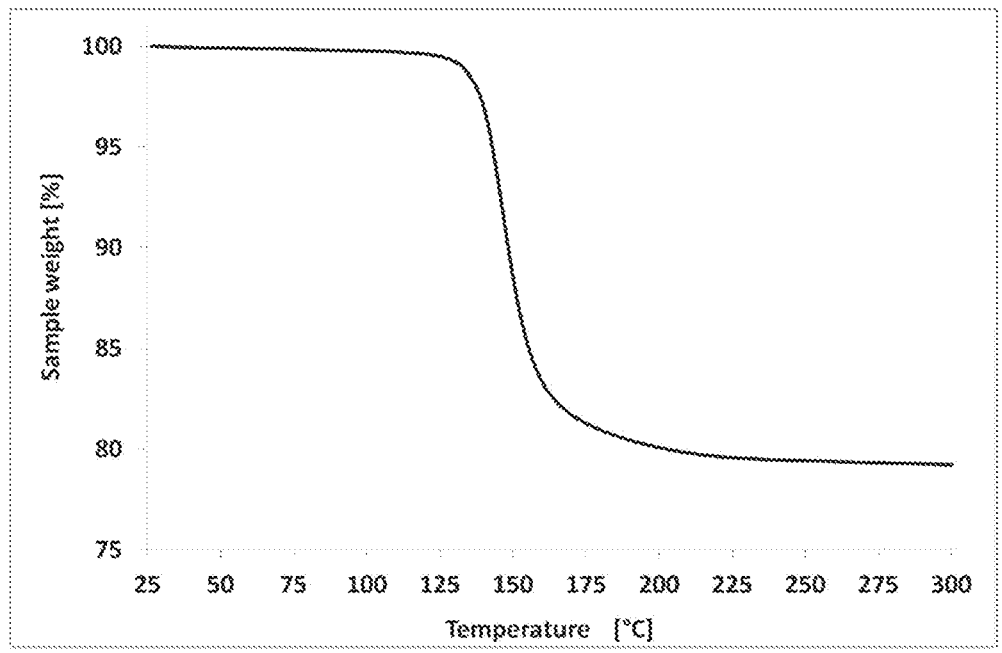
Figure 20: Water Vapour Sorption Isotherm (25 °C) of form Malonate-NF1
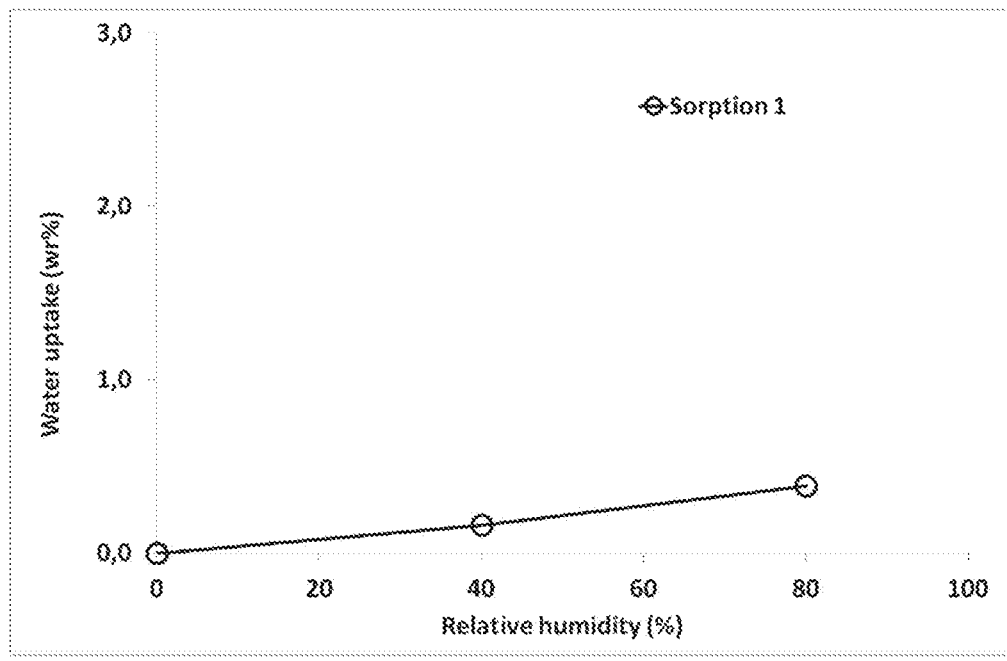

Figure 21: Powder X-ray diffractogram of Succinate salt form Succinate-NF1
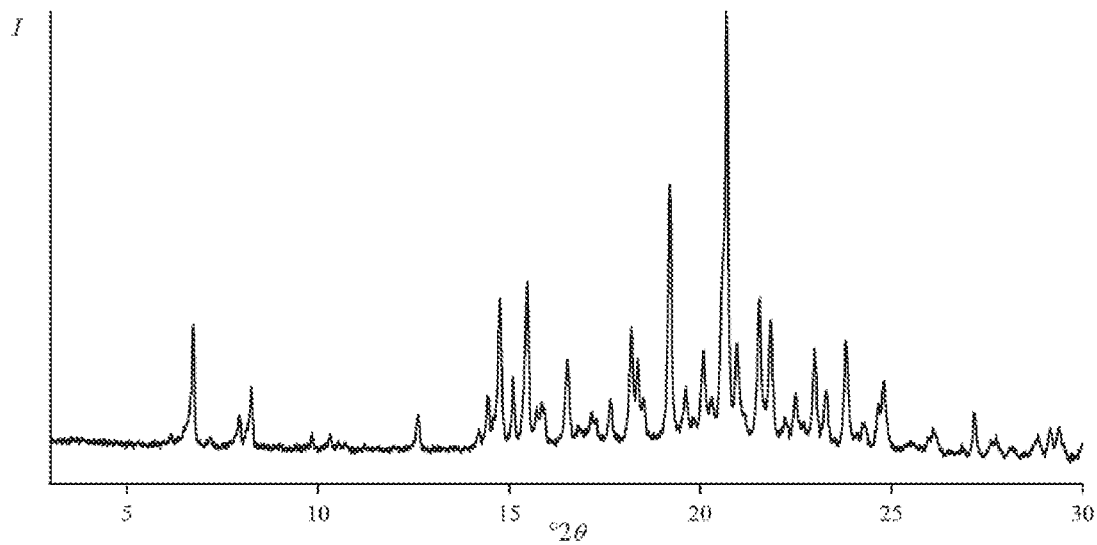
Figure 22: DSC scan of form Succinate-NF1 (5 K/min)
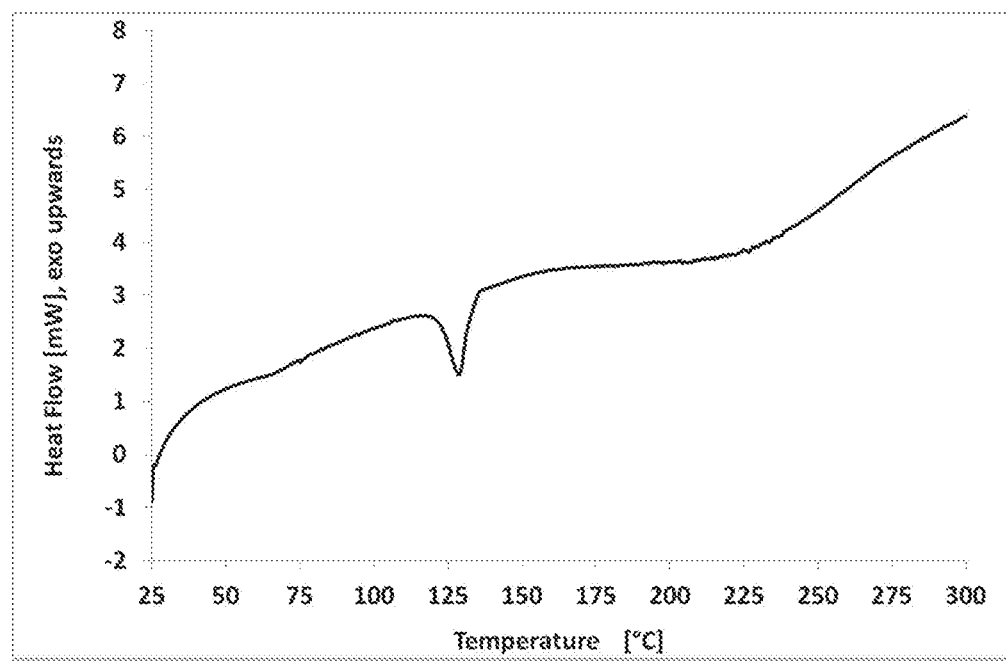

Figure 23: TGA scan of form Succinate-NF1 (5 K/min)
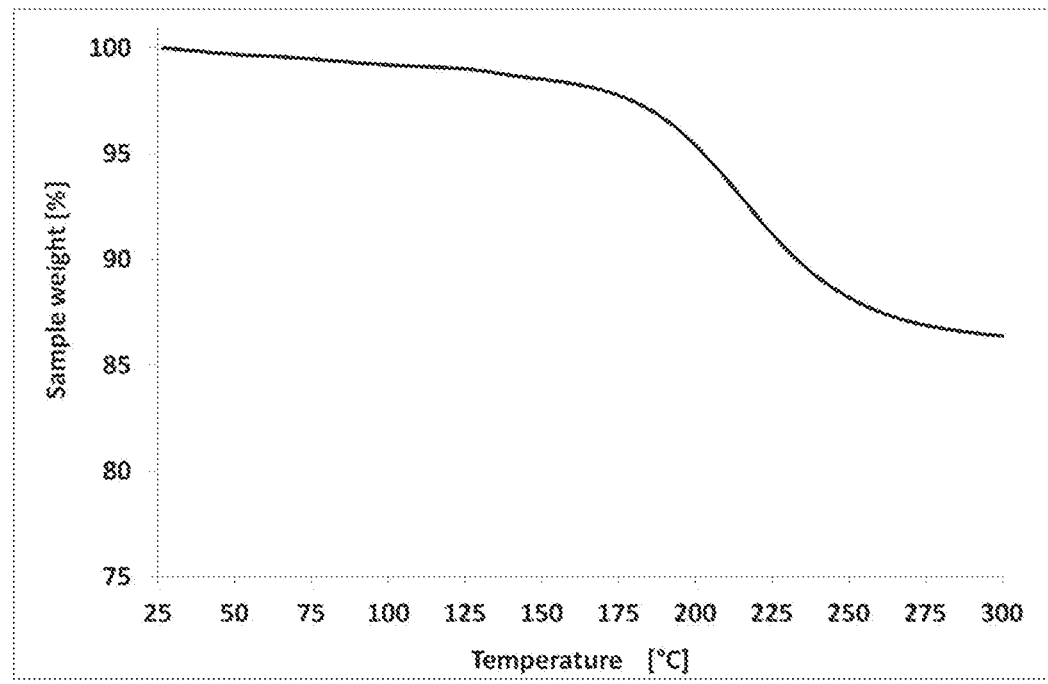
Figure 24: Water Vapour Sorption Isotherm (25 °C) of form Succinate-NF1
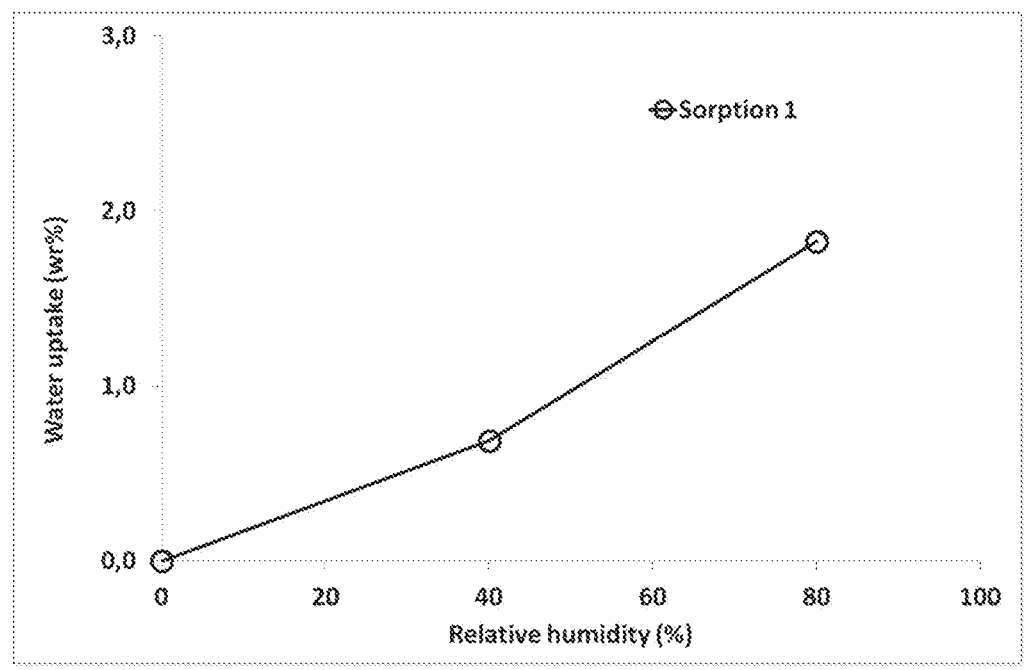

Figure 25: Powder X-ray diffractogram of Oxalate salt form Oxalate-NF1
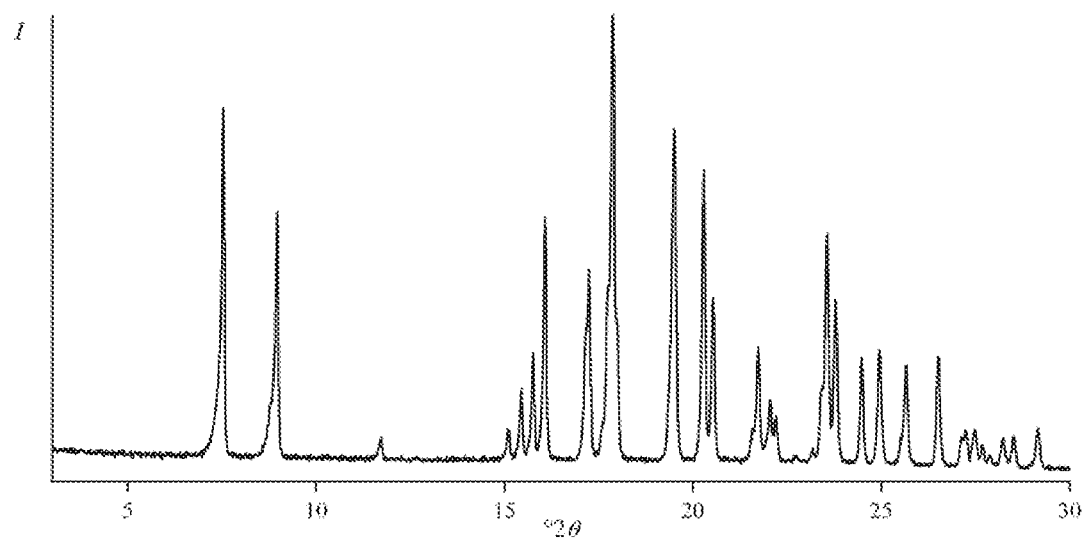
Figure 26: DSC scan of form Oxalate-NF1 (5 K/min)
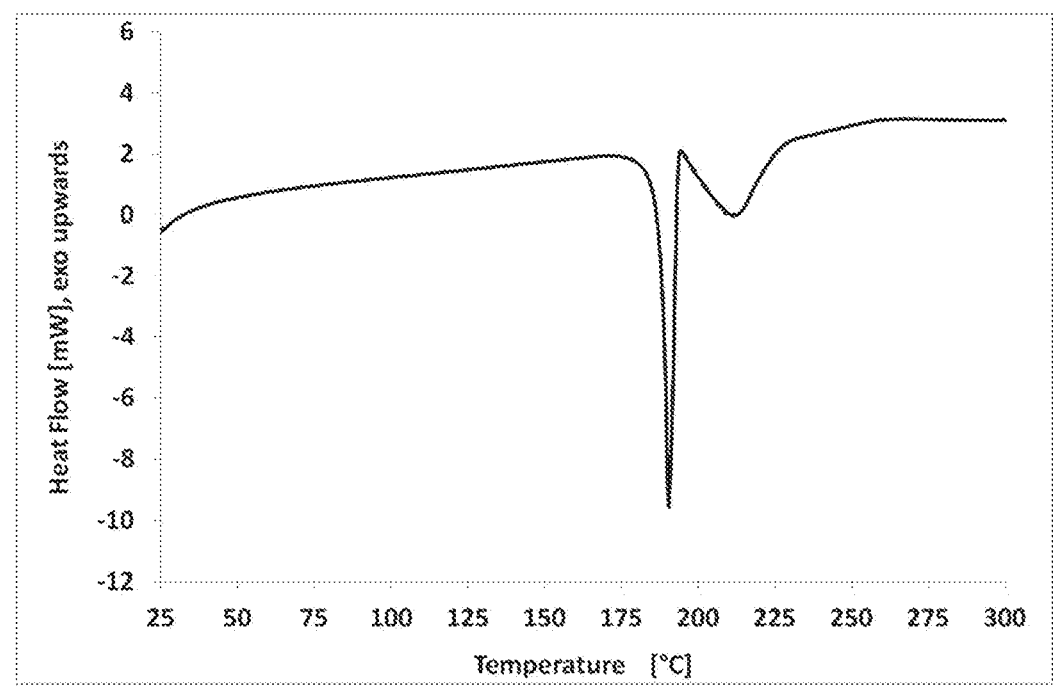

Figure 27: TGA scan of form Oxalate-NF1 (5 K/min)
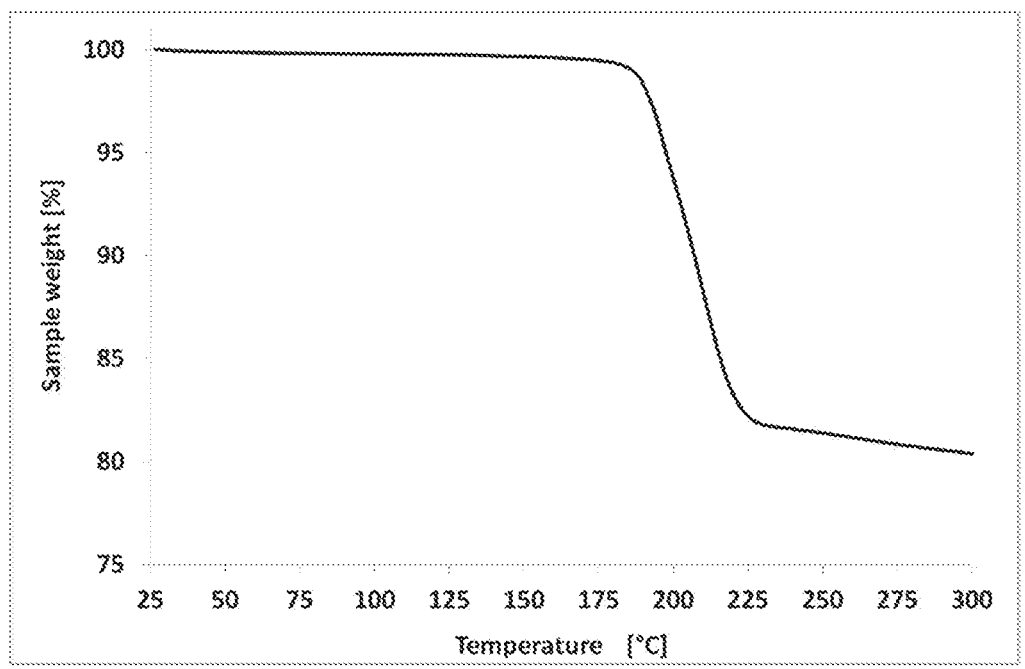

Figure 28: Water Vapour Sorption Isotherm (25 °C) of form Oxalate-NF1
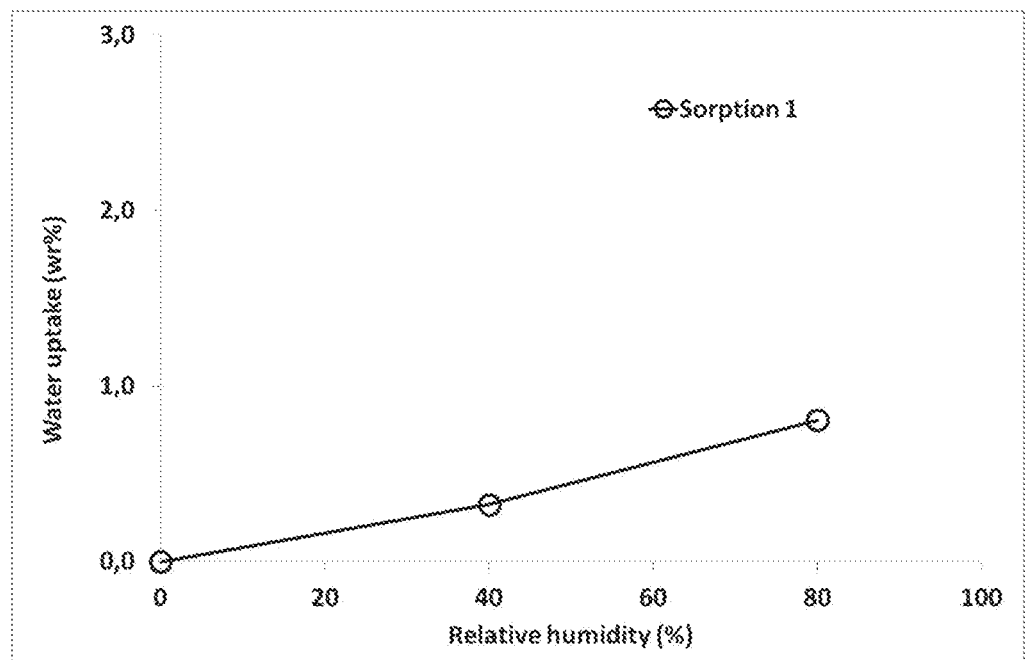
Figure 29: Powder X-ray diffractogram of Fumarate salt form Fumarate-NF1
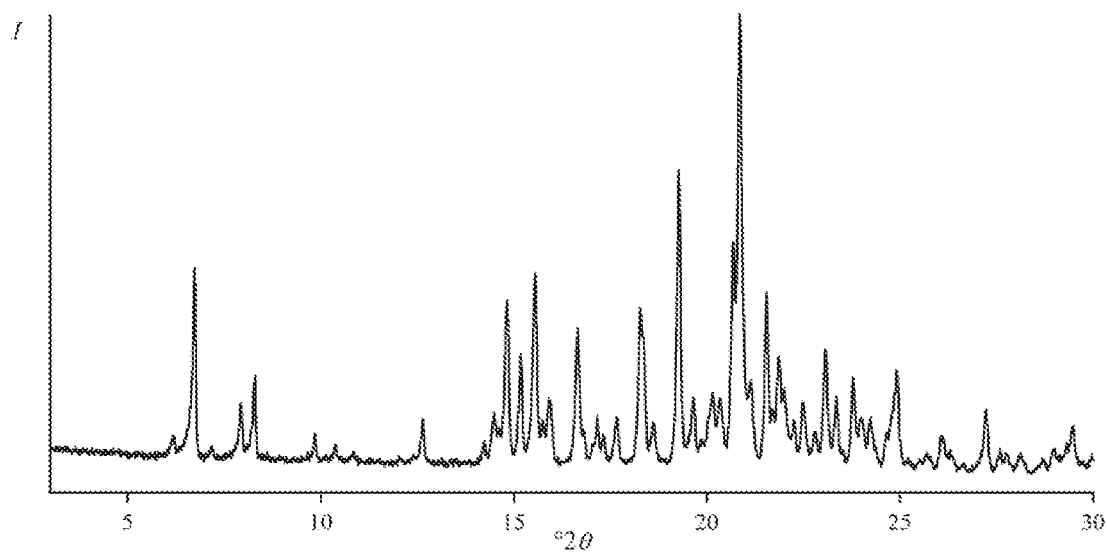

Figure 30: DSC scan of form Fumarate-NF1 (5 K/min)
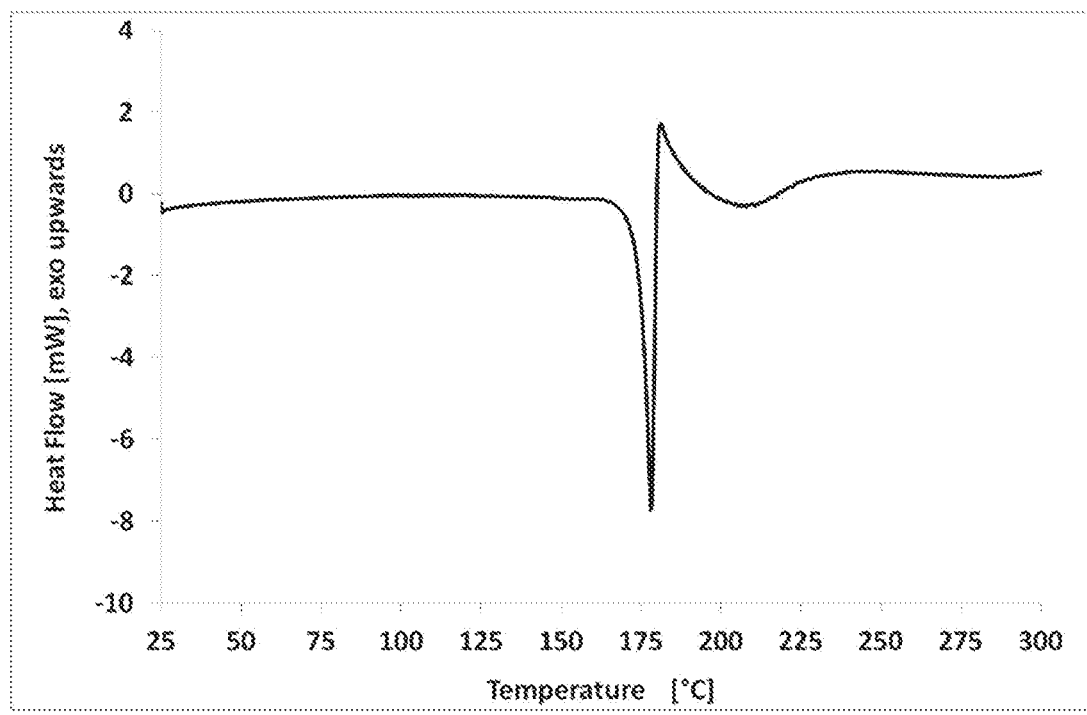
Figure 31: TGA scan of form Fumarate-NF1 (5 K/min)
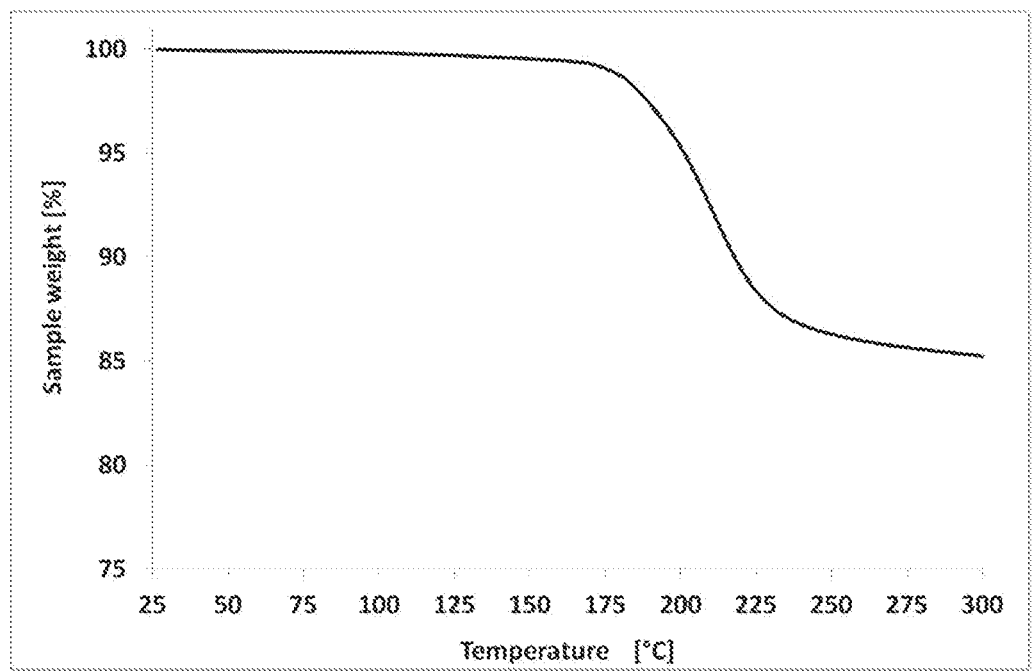

Figure 32: Water Vapour Sorption Isotherm (25 °C) of form Fumarate-NF1
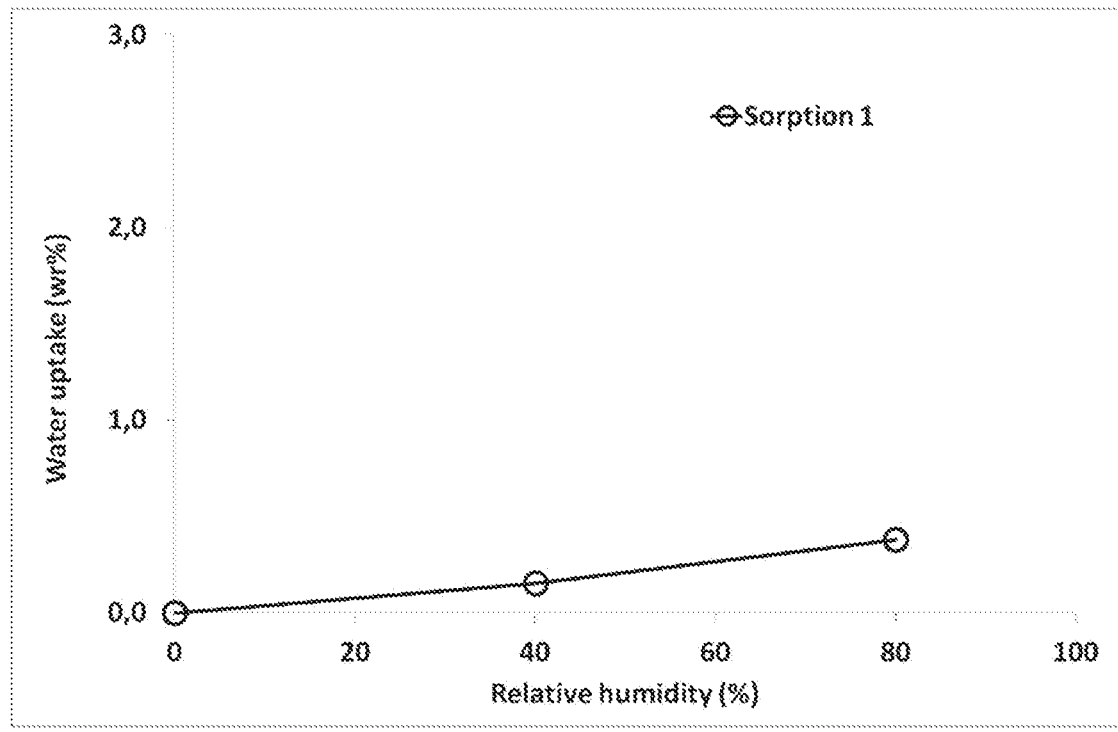
Figure 33: Powder X-ray diffractogram of Maleate salt form Maleate-NF1
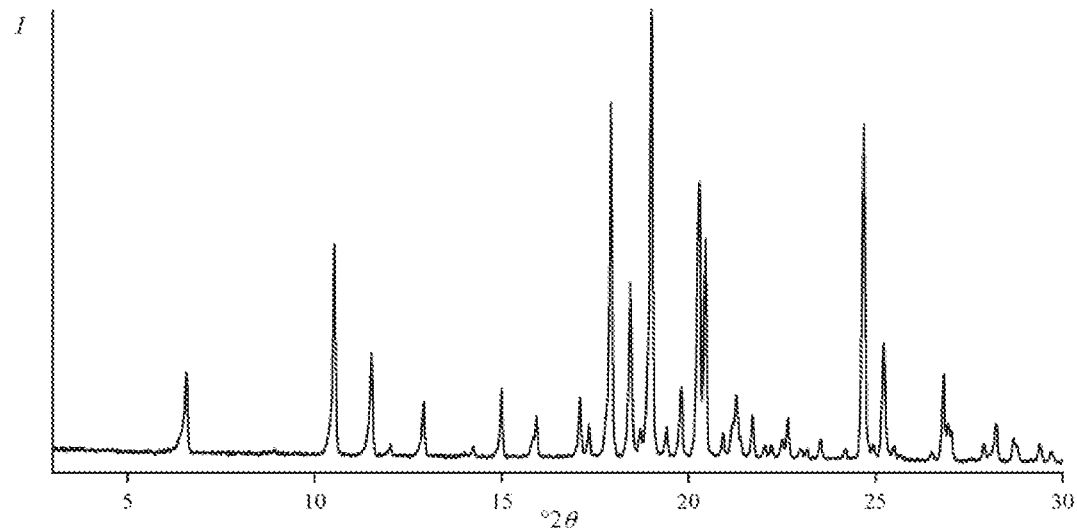

Figure 34: DSC scan of form Maleate-NF1 (5 K/min)
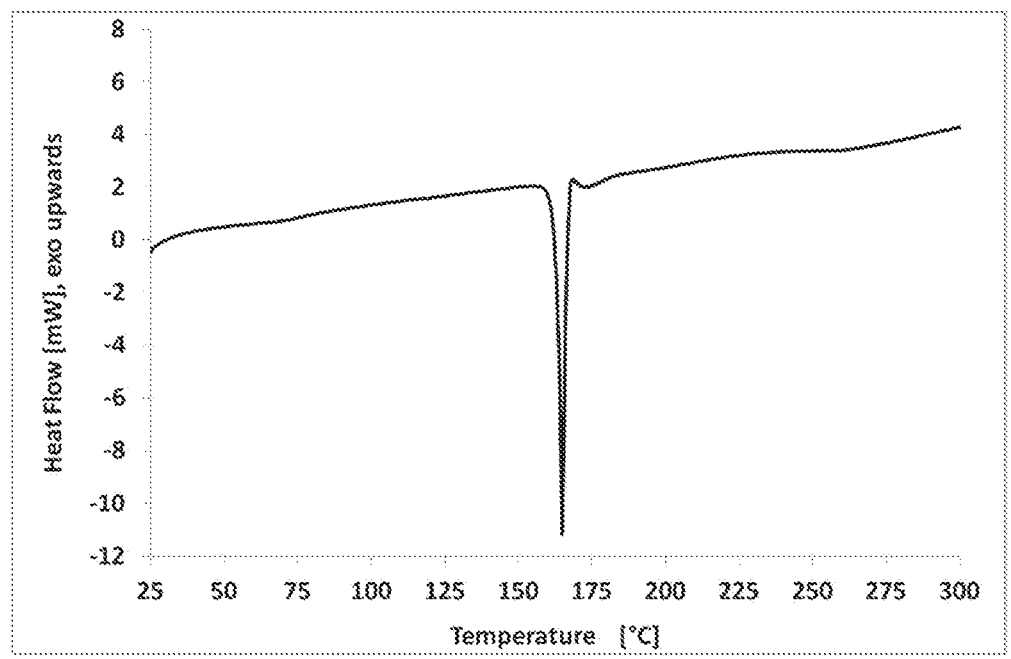
Figure 35: TGA scan of form Maleate-NF1 (5 K/min)
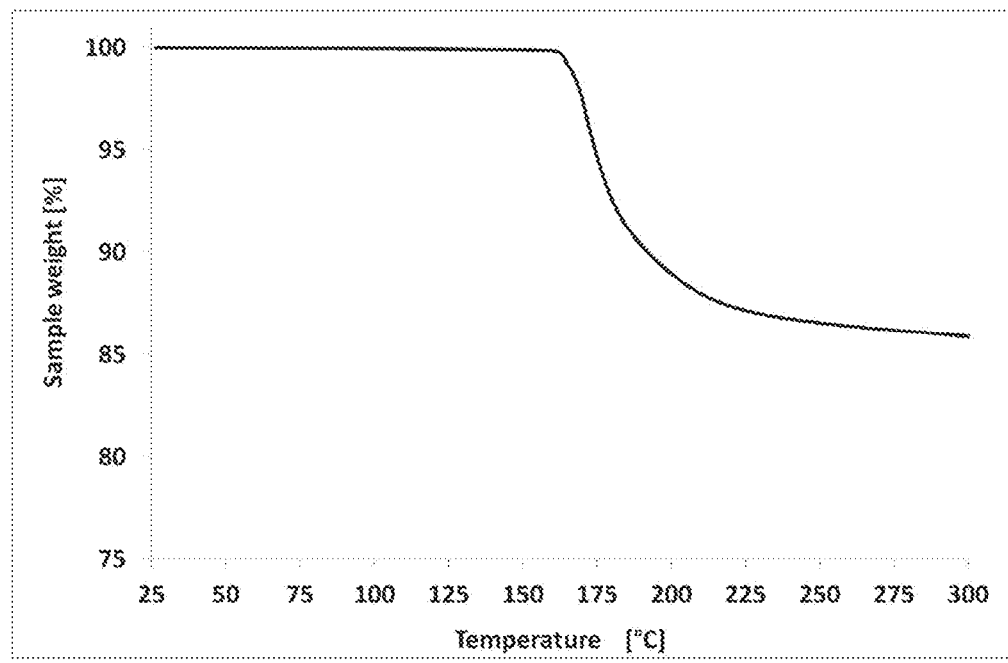

Figure 36: Water Vapour Sorption Isotherm (25 °C) of form Maleate-NF1
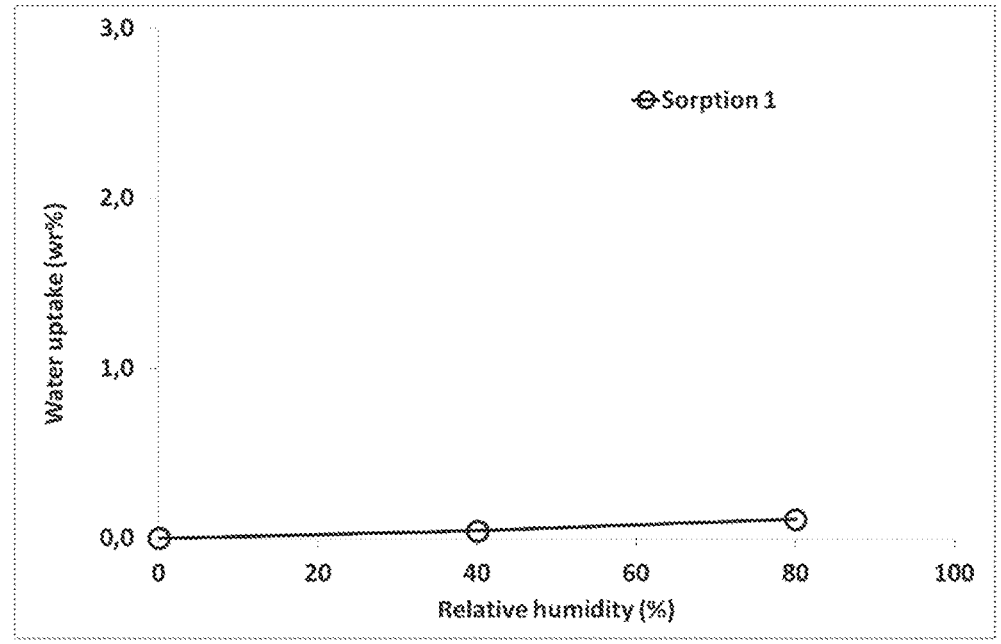
Figure 37: Powder X-ray diffractogram of Citrate salt form Citrate-NF1. The broad peak at 5.5° 2θ is due to the sample holder
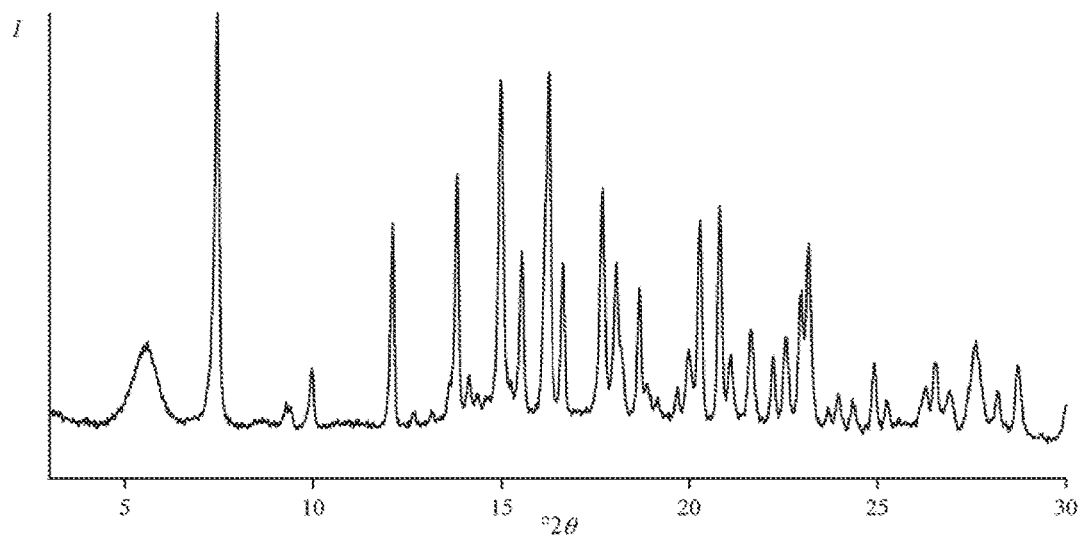

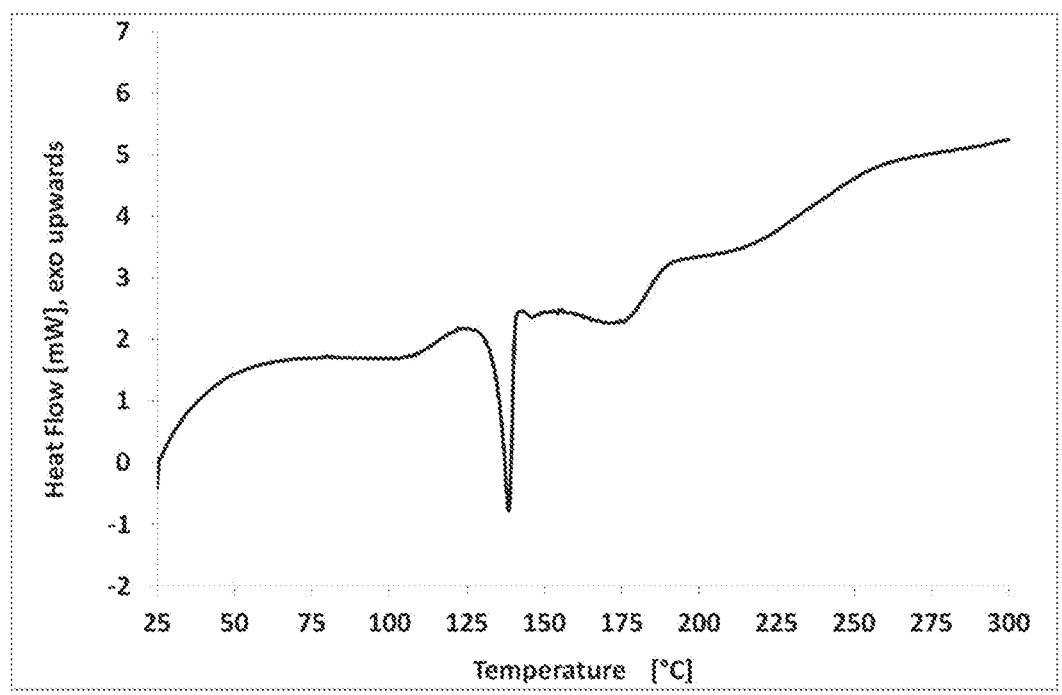
Figure 38: DSC scan of form Citrate-NF1 (5 K/min)

Figure 39: TGA scan of form Citrate-NF1 (5 K/min)
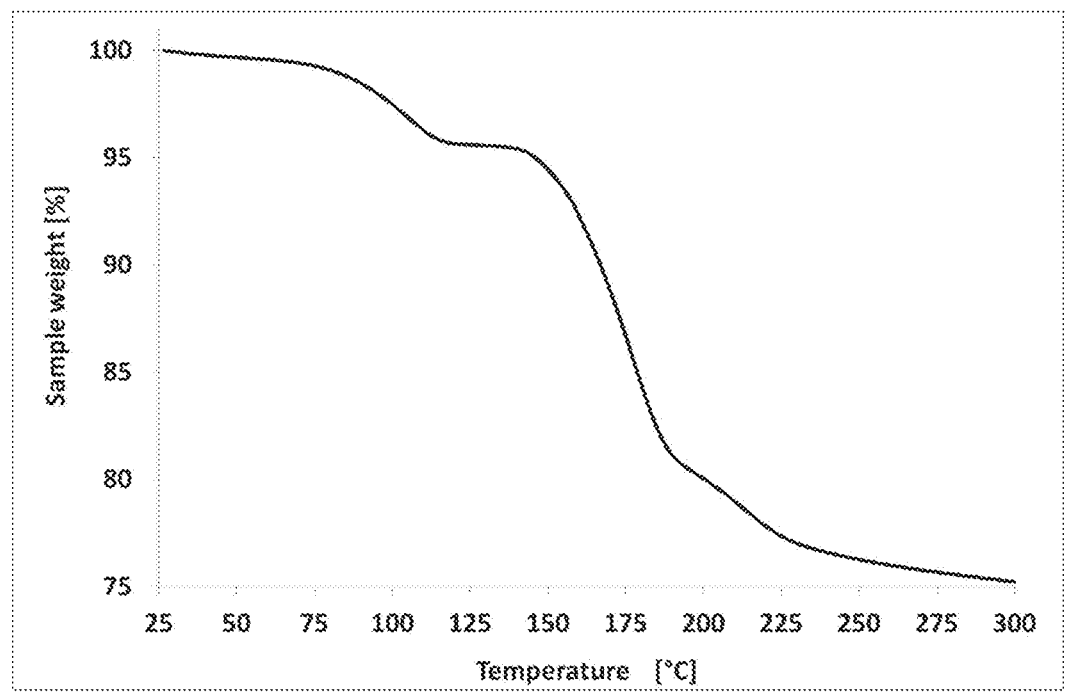
Figure 40: Water Vapour Sorption Isotherm (25 °C) of form Citrate-NF1
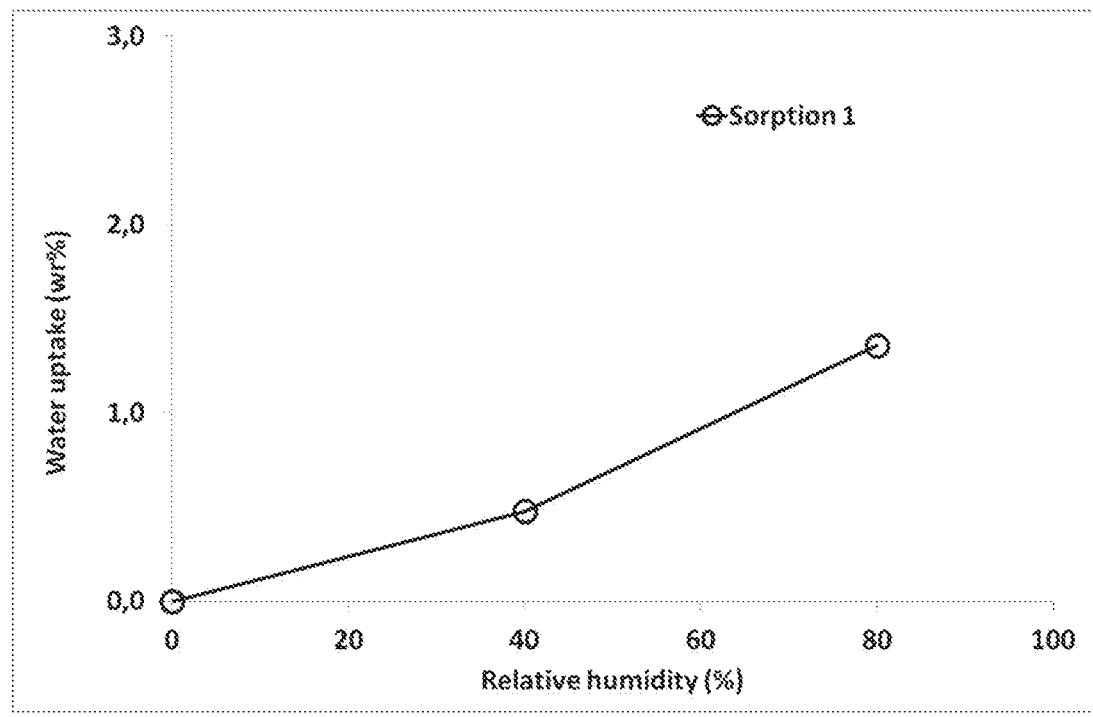

Figure 41: Powder X-ray diffractogram of free base form A1
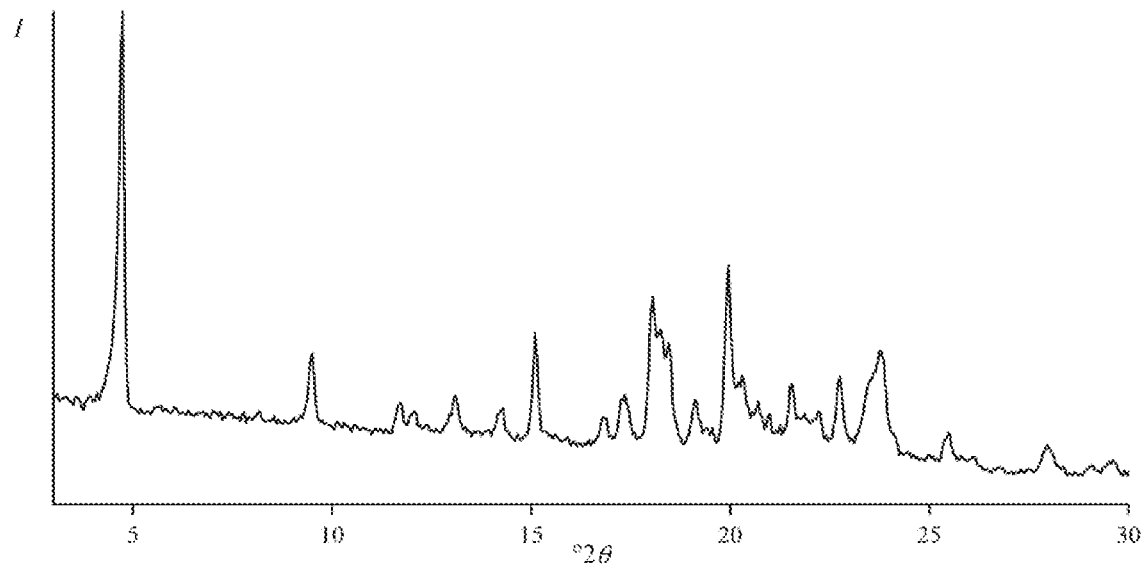
Figure 42: DSC scan of free base form A1 (50 K/min)
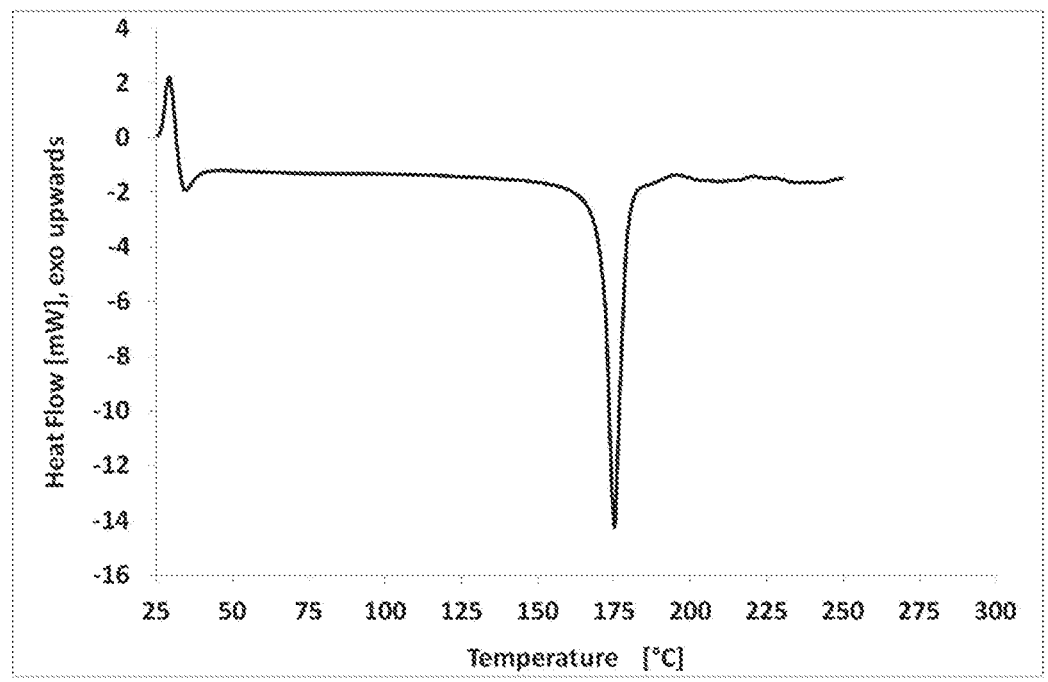

Figure 43: TGA scan of free base form A1 (5 K/min)
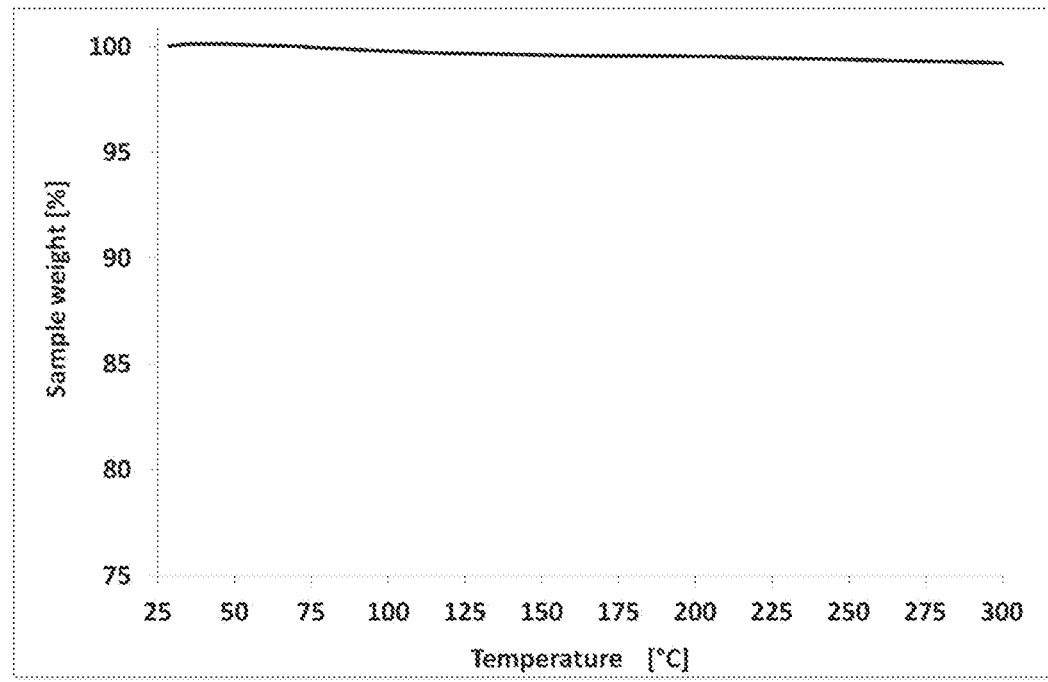
Figure 44: Water Vapour Sorption Isotherm (25 °C) of free base form A1
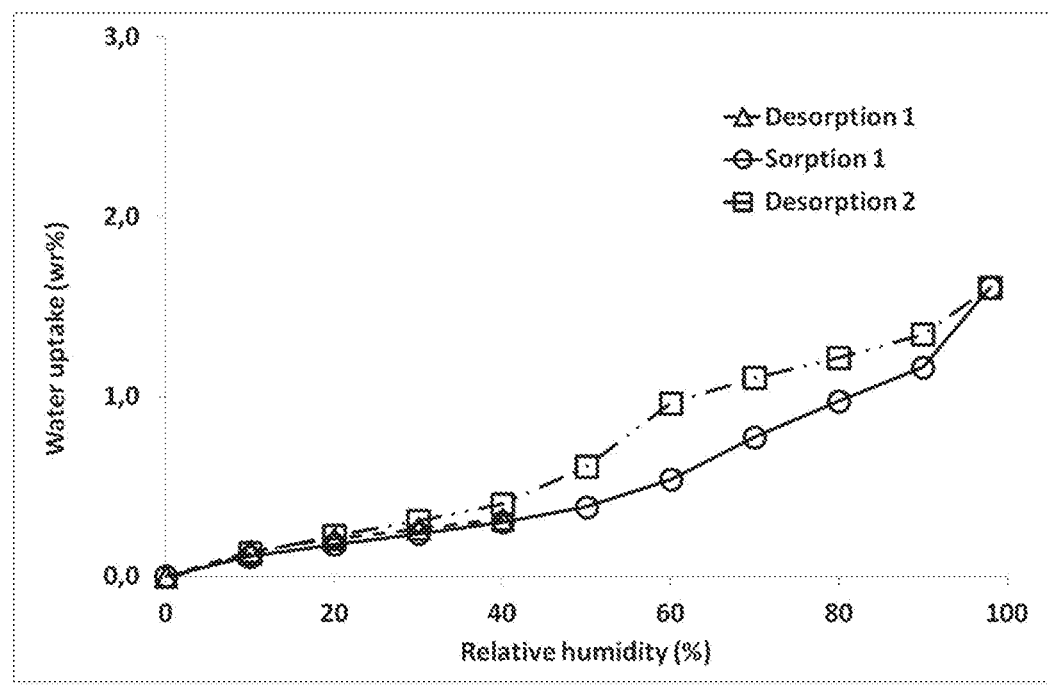

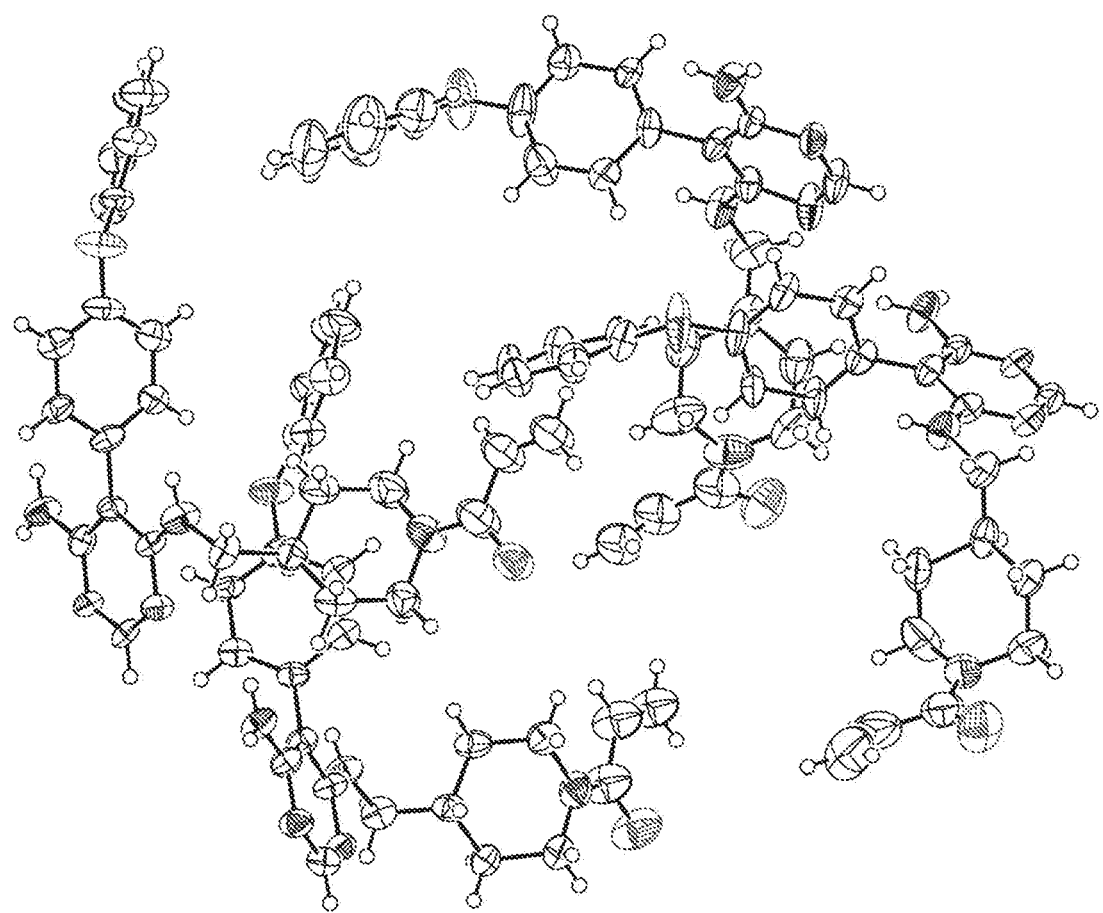
Figure 45: Single crystal structure of free base form A1 viewed approx. along *b*-axis

CRYSTALLINE FORMS OF 1-(4-{[6-AMINO-5-(4-PHENOXY-PHENYL)-PYRIMIDIN-4-YLAMINO]-METHYL}-PIPERIDIN-1-YL)-PROPENONE

RELATED APPLICATION

This application is a continuation of U.S. application Ser. No. 15/902,482, filed on Feb. 22, 2018, now U.S. Pat. No. 10,464,923, which claims the benefit of U.S. Provisional Application No. 62/528,238, filed Jul. 3, 2017, and U.S. Provisional Application No. 62/463,913, filed Feb. 27, 2017, all of which are incorporated in their entireties by reference.

TECHNICAL FIELD OF THE INVENTION

The present invention relates to solid forms of 1-(4-{[6-Amino-5-(4-phenoxy-phenyl)-pyrimidin-4-ylamino]-methyl}-piperidin-1-yl)-propenone (Compound 1) in substantially crystalline form or amorphous form, pharmaceutical compositions thereof, and methods of treatment therewith. The present invention relates to malonate, succinate, oxalate, fumarate, maleate, malate, and citrate salts of 1-(4-{[6-Amino-5-(4-phenoxy-phenyl)-pyrimidin-4-ylamino]-methyl}-piperidin-1-yl)-propenone (Compound 1), as well as solid forms of said salts, in substantially crystalline form, pharmaceutical compositions thereof, and methods of treatment therewith.

BACKGROUND OF THE INVENTION

Protein kinases constitute one of the largest families of human enzymes and regulate many different signaling processes by adding phosphate groups to proteins (T. Hunter. Cell 1987 50:823-829). Specifically, tyrosine kinases phosphorylate proteins on the phenolic moiety of tyrosine residues. The tyrosine kinase family includes members that control cell growth, migration, and differentiation. Abnormal kinase activity has been implicated in a variety of human diseases including cancers, autoimmune and inflammatory diseases. Since protein kinases are among the key regulators of cell signaling, they provide a target to modulate cellular function with small molecular kinase inhibitors and thus make good drug targets. In addition to treatment of kinase-mediated disease processes, selective and efficacious inhibitors of kinase activity are also useful for investigation of cell signaling processes and identification of other cellular targets of therapeutic interest.

There is good evidence that B-cells play a key role in the pathogenesis of autoimmune and/or inflammatory disease. Protein-based therapeutics that deplete B cells such as Rituxan are effective against autoantibody-driven inflammatory diseases such as rheumatoid arthritis (Rastetter et al. Annu Rev Med 2004 55:477). Therefore inhibitors of the protein kinases that play a role in B-cell activation should be useful therapeutics for B-cell mediated disease pathology, such as autoantibody production.

Signaling through the B-cell receptor (BCR) controls a range of B-cell responses including proliferation and differentiation into mature antibody producing cells. The BCR is a key regulatory point for B-cell activity and aberrant signaling can cause deregulated B-cell proliferation and formation of pathogenic autoantibodies that lead to multiple autoimmune and/or inflammatory diseases. Bruton's Tyrosine Kinase (BTK) is a non-BCR associated kinase that is membrane proximal and immediately downstream from BCR. Lack of BTK has been shown to block BCR signaling and therefore inhibition of BTK could be a useful therapeutic approach to block B-cell mediated disease processes. Also, BTK has been reported to play a role in apoptosis (Islam and Smith Immunol. Rev. 2000 178:49,) and thus BTK inhibitors would be useful for the treatment of certain B-cell lymphomas and leukemias (Feldhahn et al. J. Exp. Med. 2005 201:1837).

BTK is a member of the Tec family of tyrosine kinases, and has been shown to be a critical regulator of early B-cell development and mature B-cell activation and survival (Khan et al. Immunity 1995 3:283; Ellmeier et al. J. Exp. Med. 2000 192:1611). Mutation of BTK in humans leads to the condition X-linked agammaglobulinemia (XLA) (reviewed in Rosen et al. New Eng. J. Med. 1995 333:431 and Lindvall et al. Immunol. Rev. 2005 203:200). These patients are immunocompromised and show impaired maturation of B-cells, decreased immunoglobulin and peripheral B-cell levels, diminished T-cell independent immune responses as well as attenuated calcium mobilization following BCR stimulation.

Evidence for a role for BTK in autoimmune and inflammatory diseases has also been provided by BTK-deficient mouse models. In preclinical murine models of systemic lupus erythematosus (SLE), BTK-deficient mice show marked amelioration of disease progression. In addition, BTK-deficient mice are resistant to collagen-induced arthritis (Jansson and Holmdahl Clin. Exp. Immunol. 1993 94:459). A selective BTK inhibitor has demonstrated dose-dependent efficacy in a mouse arthritis model (Z. Pan et al., Chem. Med Chem. 2007 2:58-61).

BTK is also expressed by cells other than B-cells that may be involved in disease processes. BTK is key component of Fc-gamma signaling in myeloid cells. For example, BTK is expressed by mast cells and BTK-deficient bone marrow derived mast cells demonstrate impaired antigen induced degranulation (Iwaki et al. J. Biol. Chem. 2005 280:40261). This shows BTK could be useful to treat pathological mast cells responses such as allergy and asthma. Also monocytes from XLA patients, in which BTK activity is absent, show decreased TNF alpha production following stimulation (Horwood et al. J Exp Med 197:1603, 2003). Therefore TNF alpha mediated inflammation could be modulated by small molecular BTK inhibitors.

SUMMARY OF THE INVENTION

It has now been found that 1-(4-{[6-Amino-5-(4-phenoxy-phenyl)-pyrimidin-4-ylamino]-methyl}-piperidin-1-yl)-propenone (Compound 1), and pharmaceutically acceptable compositions thereof, are effective as inhibitors of BTK.

In one aspect, Compound 1 is in a substantially crystalline and salt free form referred to as Form A2 as described and characterized herein. In one aspect. Compound 1 is in a substantially crystalline and salt free form referred to as Form NF4 as described and characterized herein. In one aspect, Compound 1 is in a substantially crystalline and salt free form referred to as Form NF5 as described and characterized herein. In one aspect, Compound 1 is in a substantially crystalline and salt free form referred to as Form NF6 as described and characterized herein. In another aspect. Compound 1 is in an amorphous form as described and characterized herein.

In certain aspects. Compound 1 is Malonate salt form Malonate-NF1. In certain aspects, Compound 1 is Succinate salt form Succinate-NF1. In certain aspects, Compound 1 is Oxalate salt form Oxalate-NF1. In certain aspects. Compound 1 is Fumarate salt form Fumarate-NF1. In certain aspects, Compound 1 is Maleate salt form Maleate-NF1. In certain aspects, Compound 1 is Citrate salt form Citrate-NF1.

The properties of a solid relevant to its efficacy as a drug can be dependent on the form of the solid. For example, in a drug substance, variation in the solid form can lead to differences in properties such as melting point, dissolution rate, oral absorption, bioavailability, toxicology results and clinical trial results.

Certain advantages of the following solid forms include the following. A2: Crystalline morphic form, very good crystallinity; Slightly hygroscopic acc. to Ph. Eur. (section 5.11.), physisorption processes only; High thermal stability (m.p. ~175° C.); Higher thermodynamic solubility levels compared to prior-art form A1 in intestinal media: FaSSIF: approx. factor 1.5 higher vs form A1 and PBS buffer pH 7.4: approx., factor 2 higher vs form A1; Phase-pure manufacturability in large scale (kg). NF4: Crystalline morphic form, good crystallinity; High thermal stability (m.p. ~165° C.). NF5: Crystalline morphic form, good crystallinity; Slightly hygroscopic acc. to Ph. Eur. (section 5.11.), physisorption processes only; High thermal stability (m.p. ~164° C.); Higher kinetic solubility levels (4 h) compared to prior-art form A1 in biorelevant intestinal media: FaSSIF: approx. factor 1.5 higher vs form A1, NF6; Crystalline morphic form, good crystallinity; Slightly hygroscopic acc. to Ph. Eur. (section 5.11.), physisorption processes only; High thermal stability (m.p. ~158° C.); Higher kinetic solubility levels (4 h) compared to prior-art form A1 in biorelevant intestinal media: FaSSIF: approx. factor 3 higher vs form A1. Malonate-NF1: Crystalline morphic form, very good crystallinity: 1:1 salt stoichiometry; Slightly hygroscopic acc. to Ph. Eur. (section 5.11.), physisorption processes only; High thermal stability (m.p./dec. ~139° C.); Higher dissolution levels (2 h) compared to prior-art form A1 in biorelevant intestinal media: FaSSIF: approx. factor 2 higher vs form A1 and FeSSIF: approx. factor 3.5 higher vs form A1. Succinate-NF1: Crystalline morphic form, very good crystallinity; 1:1 salt stoichiometry; Slightly hygroscopic acc. to Ph. Eur. (section 5.11.), physisorption processes only; High thermal stability (m.p./dec. ~122° C.); Higher dissolution levels (2 h) compared to prior-art form A1 in biorelevant intestinal media: FaSSIF: approx. factor 3 higher vs form A1 and FeSSIF: approx. factor 3.5 higher vs form A1. Oxalate-NF1: Crystalline morphic form, very good crystallinity; 1:1 salt stoichiometry; Slightly hygroscopic acc. to Ph. Eur. (section 5.11.), physisorption processes only; High thermal stability (m.p./dec. ~188° C.); Higher dissolution levels (2 h) compared to prior-art form A1 in biorelevant intestinal media: FaSSIF: approx. factor 1.5 higher vs form A1 and FeSSIF: approx. factor 3.5 higher vs form A1. Fumarate-NF1: Crystalline morphic form, very good crystallinity; 1:1 salt stoichiometry; Slightly hygroscopic acc. to Ph. Eur. (section 5.11.), physisorption processes only; High thermal stability (m.p./dec. ~175° C.). Maleate-NF1: Crystalline morphic form, very good crystallinity; 1:1 salt stoichiometry; Non-hygroscopic acc. to Ph. Eur. (section 5.11.), physisorption processes only; High thermal stability (m.p./dec. ~163° C.). Citrate-NF1: Crystalline morphic form, very good crystallinity; 1:1 salt stoichiometry; Slightly hygroscopic acc. to Ph. Eur. (section 5.11.), physisorption processes only; High thermal stability (m.p./dec. ~134° C.).

Compound 1, and pharmaceutically acceptable compositions thereof, are useful for treating a variety of diseases, disorders or conditions, associated with BTK. Such diseases, disorders, or conditions include those described herein.

BRIEF DESCRIPTION OF THE DRAWINGS

FIG. 1: Form A2 Powder X-ray diffractogram.
FIG. 2: Single Crystal Structure of Free Base Form A2 Viewed Approximately Along A-Axis.
FIG. 3: DSC scan of free base form A2 (50 K/min).
FIG. 4: TGA scan of free base form A2 (5 K/min).
FIG. 5: Water Vapour Sorption Isotherm (25° C.) of free base form A2.
FIG. 6: Powder X-ray diffractogram of free base form NF4.
FIG. 7: DSC scan of free base form NF4 (50 K/min).
FIG. 8: TGA scan of free base form NF4 (5 K/min).
FIG. 9: Powder X-ray diffractogram of free base form NF5.
FIG. 10: DSC scan of free base form NF5 (50 K/min).
FIG. 11: TGA scan of free base form NF5 (5 K/min).
FIG. 12: Water Vapour Sorption Isotherm (25° C.) of free base form NF5.
FIG. 13: Powder X-ray diffractogram of free base form NF6.
FIG. 14: DSC scan of free base form NF6 (50 K/min).
FIG. 15: TGA scan of free base form NF6 (5 K/min).
FIG. 16: Water Vapour Sorption Isotherm (25° C.) of free base form NF6.
FIG. 17: Powder X-ray diffractogram of Malonate salt form Malonate-NF1.
FIG. 18: DSC scan of form Malonate-NF1 (5 K/min).
FIG. 19: TGA scan of form Malonate-NF1 (5 K/min).
FIG. 20: Water Vapour Sorption Isotherm (25° C.) of form Malonate-NF1.
FIG. 21: Powder X-ray diffractogram of Succinate salt form Succinate-NF1.
FIG. 22: DSC scan of form Succinate-NF1 (5 K/min).
FIG. 23: TGA scan of form Succinate-NF1 (5 K/min).
FIG. 24: Water Vapour Sorption Isotherm (25° C.) of form Succinate-NF1.
FIG. 25: Powder X-ray diffractogram of Oxalate salt form Oxalate-NF1.
FIG. 26: DSC scan of form Oxalate-NF1 (5 K/min).
FIG. 27: TGA scan of form Oxalate-NF1 (5 K/min).
FIG. 28: Water Vapour Sorption Isotherm (25° C.) of form Oxalate-NF1.
FIG. 29: Powder X-ray diffractogram of Fumarate salt form Fumarate-NF1.
FIG. 30: DSC scan of form Fumarate-NF1 (5 K/min).
FIG. 31: TGA scan of form Fumarate-NF1 (5 K/min).
FIG. 32: Water Vapour Sorption Isotherm (25° C.) of form Fumarate-NF1.
FIG. 33: Powder X-ray diffractogram of Maleate salt form Maleate-NF1.
FIG. 34: DSC scan of form Maleate-NF1 (5 K/min).
FIG. 35: TGA scan of form Maleate-NF1 (5 K/min).
FIG. 36: Water Vapour Sorption Isotherm (25° C.) of form Maleate-NF1.
FIG. 37: Powder X-ray diffractogram of Citrate salt form Citrate-NF1.
FIG. 38: DSC scan of form Citrate-NF1 (5 K/min).
FIG. 39: TGA scan of form Citrate-NF1 (5 K/min).
FIG. 40: Water Vapour Sorption Isotherm (25° C.) of form Citrate-NF1.
FIG. 41: Powder X-ray diffractogram of free base form A1.
FIG. 42: DSC scan of free base form A1 (50 K/min).
FIG. 43: TGA scan of free base form A1 (5 K/min).
FIG. 44: Water Vapour Sorption Isotherm (25° C.) of free base form A1.

FIG. 45: Single crystal structure of free base form A1 viewed approx. along b-axis.

DETAILED DESCRIPTION OF CERTAIN EMBODIMENTS

1. General Description of Compounds of the Invention

In certain aspects, the present invention provides for inhibitors of BTK. In some embodiments, such compounds include those of the formulae described herein, or a pharmaceutically acceptable salt thereof, wherein each variable is as defined and described herein.

2. Compounds and Definitions

As used herein the term "amorphous" refers to solid forms that consist of disordered arrangements of molecules and do not possess a distinguishable crystal lattice.

As used herein "crystalline" refers to compounds or compositions where the structural units are arranged in fixed geometric patterns or lattices, so that crystalline solids have rigid long range order. The structural units that constitute the crystal structure can be atoms, molecules, or ions. Crystalline solids show definite melting points.

The term "chemically stable", as used herein, means that the solid form of Compound 1 does not decompose into one or more different chemical compounds when subjected to specified conditions, e.g., 40° C./75% relative humidity, for a specific period of time, e.g. 1 day, 2 days, 3 days, 1 week, 2 weeks, or longer. In some embodiments, less than 25% of the solid form of Compound 1 decomposes, in some embodiments, less than about 20%, less than about 15%, less than about 10%, less than about 5%, less than about 3%, less than about 1%, less than about 0.5% of the form of Compound 1 decomposes under the conditions specified. In some embodiments, no detectable amount of the solid form of Compound 1 decomposes.

The term "physically stable", as used herein, means that the solid form of Compound 1 does not change into one or more different physical forms of Compound 1 (e.g. different solid forms as measured by XRPD, DSC, etc.) when subjected to specific conditions, e.g., 40° C./75% relative humidity, for a specific period of time, e.g. 1 day, 2 days, 3 days, 1 week, 2 weeks, or longer. In some embodiments, less than 25% of the solid form of Compound 1 changes into one or more different physical forms when subjected to specified conditions. In some embodiments, less than about 20%, less than about 15%, less than about 10%, less than about 5%, less than about 3%, less than about 1%, less than about 0.5% of the solid form of Compound 1 changes into one or more different physical forms of Compound 1 when subjected to specified conditions. In some embodiments, no detectable amount of the solid form of Compound 1 changes into one or more physically different solid forms of Compound 1.

As used herein, the phrase "substantially amorphous Compound 1" is used interchangeably with the phrases "amorphous Compound 1," "amorphous Compound 1 substantially free of crystalline Compound 1," and "substantially amorphous 1-(4-{[6-Amino-5-(4-phenoxy-phenyl)-pyrimidin-4-ylamino]-methyl}-piperidin-1-yl)-propenone." In some embodiments, substantially amorphous Compound 1 has less than about 30% crystalline Compound 1, for example, less than about 30% of crystalline Compound 1, e.g., less than about 25% crystalline Compound 1, less than about 20% crystalline Compound 1, less than about 15% crystalline Compound 1, less than about 10% crystalline Compound 1, less than about 5% crystalline Compound 1, less than about 2% crystalline Compound 1.

As used herein, the phrase "substantially crystalline Compound 1" is used interchangeably with the phrases "Compound 1," and "crystalline Compound 1 substantially free of amorphous Compound 1." In some embodiments, substantially crystalline Compound 1 has less than about 30% amorphous Compound 1 or other solid forms, for example, less than about 30% of amorphous Compound 1 or other solid forms, e.g., less than about 25% amorphous Compound 1 or other solid forms, less than about 20% amorphous Compound 1 or other solid forms, less than about 15% amorphous Compound 1 or other solid forms, less than about 10% amorphous Compound 1 or other solid forms, less than about 5% amorphous Compound 1 or other solid forms, less than about 2% amorphous Compound 1 or other solid forms. In some embodiments, substantially crystalline Compound 1 has less than about 1% amorphous Compound 1 or other solid forms.

The term "substantially free" (as in the phrase "substantially free of form X") when referring to a designated solid form of Compound 1 (e.g., an amorphous or crystalline form described herein) means that there is less than 20% (by weight) of the designated form(s) or co-form(s) (e.g., a crystalline or amorphous form of Compound 1) present, more preferably, there is less than 10% (by weight) of the designated form(s) present, more preferably, there is less than 5% (by weight) of the designated form(s) present, and most preferably, there is less than 1% (by weight) of the designated form(s) present.

The term "substantially pure" when referring to a designated solid form of Compound 1 (e.g., an amorphous or crystalline solid form described herein) means that the designated solid form contains less than 20% (by weight) of residual components such as alternate polymorphic or isomorphic crystalline form(s) or co-form(s) of Compound 1. It is preferred that a substantially pure solid form of Compound 1 contains less than 10% (by weight) of alternate polymorphic or isomorphic crystalline forms of Compound 1, more preferably less than 5% (by weight) of alternate polymorphic or isomorphic crystalline forms of Compound 1, and most preferably less than 1% (by weight) of alternate polymorphic or isomorphic crystalline forms of Compound 1.

As used herein, a "dispersion" refers to a disperse system in which one substance, the dispersed phase, is distributed, in discrete units, throughout a second substance (the continuous phase or vehicle). The size of the dispersed phase can vary considerably (e.g. colloidal particles of nanometer dimension, to multiple microns in size). In general, the dispersed phases can be solids, liquids, or gases. In the case of a solid dispersion, the dispersed and continuous phases are both solids. In pharmaceutical applications, a solid dispersion can include a crystalline drug (dispersed phase) in an amorphous polymer (continuous phase), or alternatively, an amorphous drug (dispersed phase) in an amorphous polymer (continuous phase). In some embodiments an amorphous solid dispersion includes the polymer constituting the dispersed phase, and the drug constitutes the continuos phase. In some embodiments, the dispersion includes amorphous Compound 1 or substantially amorphous Compound 1.

The term "solid amorphous dispersion" generally refers to a solid dispersion of two or more components, usually a drug and polymer, but possibly containing other components such as surfactants or other pharmaceutical excipients, where Compound 1 is amorphous or substantially amorphous (e.g., substantially free of crystalline Compound 1), and the physical stability and/or dissolution and/or solubility of the amorphous drug is enhanced by the other components.

As used herein, the terms "about" and "approximately", when used in connection with doses, amounts, or weight percent of ingredients of a composition or a dosage form, mean a dose, amount, or weight percent that is recognized by one of ordinary skill in the art to provide a pharmacological effect equivalent to that obtained from the specified dose, amount, or weight percent. Specifically the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range.

The abbreviation "XRPD" stands for X-ray powder diffraction. The term XRPD is used interchangeably with PXRD.

The abbreviation "DSC" stands for differential scanning calorimetry.

The abbreviation "TGA" stands for thermogravimetric analysis.

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version. Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B, and March, J., John Wiley & Sons, New York: 2001, the entire contents of which are hereby incorporated by reference.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

As used herein, the term "modulator" is defined as a compound that binds to and/or inhibits the target with measurable affinity. In certain embodiments, a modulator has an $IC_{50}$ and/or binding constant of less about 50 µM, less than about 1 µM, less than about 500 nM, less than about 100 nM, or less than about 10 nM.

The terms "measurable affinity" and "measurably inhibit," as used herein, means a measurable change in BTK activity between a sample comprising a compound of the present invention, or composition thereof, and BTK, and an equivalent sample comprising BTK, in the absence of said compound, or composition thereof.

3. Description of Exemplary Compounds

According to one aspect, the present invention provides a solid form of compound 1.

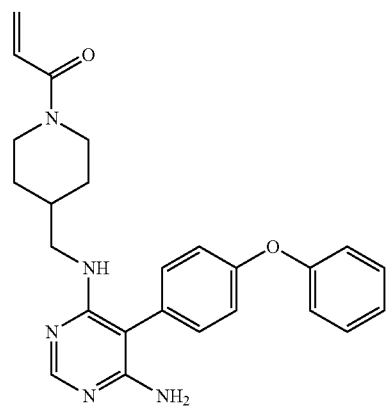

1 or a pharmaceutically acceptable salt thereof.

In certain embodiments, the invention provides solid form A2 of compound 1, solid form NF4 of compound 1, solid form NF5 of compound 1, solid form NF6 of compound 1, solid form A1 of compound 1, solid form Malonate-NF1 of a malonate salt of compound 1, solid form Succinate-NF1 of a succinate salt of compound 1, solid form Oxalate-NF1 of an oxalate salt of compound 1, solid form Fumarate-NF1 of a fumarate salt of compound 1, solid form Maleate-NF1 of a maleate salt of compound 1, solid form L-Malate-NF1 of a L-malate salt of compound 1, solid form Citrate-NF1 of a citrate salt of compound 1, solid form A1 of compound 1, or a solid form mixture of A1 and A2 of compound 1.

In one embodiment, the invention provides 1-(4-{[6-Amino-5-(4-phenoxy-phenyl)-pyrimidin-4-ylamino]-methyl}-piperidin-1-yl)-propenone (Compound 1) characterized as crystalline form A2.

In certain embodiments, form A2 is characterized by one or more 2θ peaks at 4.7, 17.5, and 20.6 degrees. In certain embodiments, form A2 is characterized by two or more 2θ peaks at 4.7, 17.5, and 20.6 degrees. In certain embodiments, form A2 is characterized by 2θ peaks at 4.7, 17.5, and 20.6 degrees.

In certain embodiments, form A2 is characterized by one or more 2θ peaks at 4.7, 9.4, 15.0, 17.5, 17.9, 19.0, 19.7, 20.6 and 23.4 degrees. In certain embodiments, form A2 is characterized by two or more 2θ peaks at 4.7, 9.4, 15.0, 17.5, 17.9, 19.0, 19.7, 20.6 and 23.4 degrees. In certain embodiments, form A2 is characterized by three or more 2θ peaks at 4.7, 9.4, 15.0, 17.5, 17.9, 19.0, 19.7, 20.6 and 23.4 degrees. In certain embodiments, form A2 is characterized by four or more 2θ peaks at 4.7, 9.4, 15.0, 17.5, 17.9, 19.0, 19.7, 20.6 and 23.4 degrees. In certain embodiments, form A2 is characterized by five or more 2θ peaks at 4.7, 9.4, 15.0, 17.5, 17.9, 19.0, 19.7, 20.6 and 23.4 degrees. In certain embodiments, form A2 is characterized by six or more 2θ peaks at 4.7, 9.4, 15.0, 17.5, 17.9, 19.0, 19.7, 20.6 and 23.4 degrees. In certain embodiments, form A2 is characterized by seven or more 2θ peaks at 4.7, 9.4, 15.0, 17.5, 17.9, 19.0, 19.7, 20.6 and 23.4 degrees. In certain embodiments, form A2 is characterized by 2θ peaks at 4.7, 9.4, 15.0, 17.5, 17.9, 19.0, 19.7, 20.6 and 23.4 degrees.

In certain embodiments, form A2 is characterized by 2θ peaks at

| No. | °2θ (Cu—K$\alpha_1$ radiation) ± 0.2° |
|---|---|
| 1 | 4.7 |
| 2 | 9.4 |
| 3 | 11.7 |
| 4 | 12.4 |
| 5 | 12.7 |
| 6 | 13.4 |
| 7 | 13.7 |
| 8 | 14.2 |
| 9 | 15.0 |
| 10 | 16.6 |
| 11 | 17.5 |
| 12 | 17.9 |
| 13 | 18.2 |
| 14 | 19.0 |
| 15 | 19.7 |
| 16 | 20.3 |
| 17 | 20.6 |
| 18 | 21.0 |
| 19 | 21.9 |
| 20 | 22.2 |
| 21 | 23.1 |
| 22 | 23.4 |
| 23 | 25.9 |
| 24 | 27.8 |

In another embodiment, form A2 is characterized by a diffraction pattern substantially similar to that of FIG. 1.

A Powder X-Ray Diffraction pattern of free base form A2 was obtained by standard techniques as described in the European Pharmacopeia 6$^{th}$ Edition chapter 2.9.33, and was characterised by the following X-ray powder diffractogram (monochromatic Cu—K$\alpha_1$ radiation, λ=1.5406 Å, Stoe Sta-diP 611 KL transmission diffractometer). See Example 4.

In certain embodiments, form A2 is characterized by a crystal form, having a monoclinic space group P2$_1$ with the lattice parameters (at 200 K) a=9.4±0.1 Å, b=37.2±0.2 Å, c=12.8±0.1 Å, and β=91.9±0.50 (with α=γ=90°). Single crystal X-Ray Structure data were obtained on free base form A2 as well (SuperNova diffractometer from Agilent, equipped with CCD Detector using Cu K$_\alpha$ radiation at 200 K).

In certain embodiments, form A2 is an anhydrous form.

Other physical properties of form A2 include the following: Thermal behavior of form A2 shows a melting peak onset at approx. 175±2° C. (based on multiple measurements on different samples of form A2). Thermogravimetric analysis reveals very low weight loss <0.5 wt % up to this temperature. DSC scan of form A2 was acquired on a Mettler-Toledo DSC 821 with a heating rate of 50 K/min, using nitrogen purge gas at 50 mL/min. TGA scan of form A2 was acquired on a Mettler-Toledo TGA 851 with a heating rate of 5 K/min, using nitrogen purge gas at 50 mL/min. Water Vapour Sorption behavior of form A2 reveals small water uptake levels ≤1 wt % in the relative humidity (rh) range 0-98% rh, and very slightly elevated water uptake levels ≤2 wt % in the relative humidity (rh) range 90-98% rh. Form A2 can be classified as slightly hygroscopic according to Ph. Eur. Criteria (section 5.11.). Water Vapour Sorption isotherm was acquired on a DVS-Intrinsic system from SMS. Kinetic solubility of form A2 in Fasted-State Simulated Intestinal Fluid [FaSSIF, pH 6.5] at RT (approx 22° C.) was determined to be approx. 25 µg/mL (after 2 h) (see example 8a). Thermodynamic solubility (24 h) of form A2 at 37° C. was determined to be approx. 33 µg/mL in Fasted-State Simulated Intestinal Fluid [FaSSIF, pH 6.5], and approx. 27 µg/mL in USP Phosphate buffer [pH 7.4], respectively (see example 8b). In certain embodiments, form A2 provides good crystallinity, is slightly hygroscopic, provides high thermal stability, and has very good manufacturability in larger scale. Surprisingly, form A2 exhibits higher thermodynamic solubility compared to form A1 despite being exceptionally stable upon heating as well as upon exposure to elevated relative humidity levels.

In one embodiment, the invention provides 1-(4-{[6-Amino-5-(4-phenoxy-phenyl)-pyrimidin-4-ylamino]-methyl}-piperidin-1-yl)-propenone (Compound 1) characterized as crystalline form NF4.

In certain embodiments, form NF4 is characterized by one or more 2θ peaks at 4.7, 16.8, and 20.8 degrees. In certain embodiments, form NF4 is characterized by two or more 2θ peaks at 4.7, 16.8, and 20.8 degrees. In certain embodiments, form NF4 is characterized by 2θ peaks at 4.7, 16.8, and 20.8 degrees.

In certain embodiments, form NF4 is characterized by one or more 2θ peaks at 4.7, 9.5, 16.8, 17.4, 17.7, 19.8, 20.4, and 20.8 degrees. In certain embodiments, form NF4 is characterized by two or more 2θ peaks at 4.7, 9.5, 16.8, 17.4, 17.7, 19.8, 20.4, and 20.8 degrees. In certain embodiments, form NF4 is characterized by three or more 2θ peaks at 4.7, 9.5, 16.8, 17.4, 17.7, 19.8, 20.4, and 20.8 degrees. In certain embodiments, form NF4 is characterized by four or more 2θ peaks at 4.7, 9.5, 16.8, 17.4, 17.7, 19.8, 20.4, and 20.8 degrees. In certain embodiments, form NF4 is characterized by five or more 2θ peaks at 4.7, 9.5, 16.8, 17.4, 17.7, 19.8, 20.4, and 20.8 degrees. In certain embodiments, form NF4 is characterized by six or more 2θ peaks at 4.7, 9.5, 16.8, 17.4, 17.7, 19.8, 20.4, and 20.8 degrees. In certain embodiments, form NF4 is characterized by seven or more 2θ peaks at 4.7, 9.5, 16.8, 17.4, 17.7, 19.8, 20.4, and 20.8 degrees. In certain embodiments, form NF4 is characterized by 2θ peaks at 4.7, 9.5, 16.8, 17.4, 17.7, 19.8, 20.4, and 20.8 degrees.

In certain embodiments, form NF4 is characterized by 2θ peaks at

| No. | °2θ (Cu—Kα$_1$ radiation) ± 0.2° |
|---|---|
| 1 | 4.7 |
| 2 | 9.5 |
| 3 | 13.1 |
| 4 | 13.6 |
| 5 | 14.0 |
| 6 | 16.8 |
| 7 | 17.4 |
| 8 | 17.7 |
| 9 | 18.6 |
| 10 | 18.8 |
| 11 | 19.3 |
| 12 | 19.8 |
| 13 | 20.4 |
| 14 | 20.8 |
| 15 | 21.4 |
| 16 | 22.3 |
| 17 | 22.9 |
| 18 | 23.7 |
| 19 | 24.0 |
| 20 | 24.9 |

In another embodiment, form NF4 is characterized by a diffraction pattern substantially similar to that of FIG. 6.

A Powder X-Ray Diffraction pattern of free base form NF4 was obtained by standard techniques as described in the European Pharmacopeia 6$^{th}$ Edition chapter 2.9.33, and was characterised by the following X-ray powder diffractogram (monochromatic Cu—Kα$_1$ radiation, λ=1.5406 Å, Stoe StadiP 611 KL transmission diffractometer). See Example 5.

In another embodiment, form NF4 is characterized as a crystalline anhydrous form.

Other physical properties of form NF4 include the following: Thermal behavior of form NF4 shows a melting peak onset at approx. 165±1° C. (based on multiple measurements on one sample of form NF4). Thermogravimetric analysis reveals very low weight loss 51.0 wt % up to this temperature. DSC and TGA profiles are displayed below. DSC scan of form NF4 was acquired on a Mettler-Toledo DSC 821 with a heating rate of 50 K/min, using nitrogen purge gas at 50 mL/min. TGA scan of form NF4 was acquired on a Mettler-Toledo TGA 851 with a heating rate of 5 K/min, using nitrogen purge gas at 50 mL/min. Overall, free base form NF4 reveals acceptable solid-state properties (satisfying crystallinity, high thermal stability).

In one embodiment, the invention provides 1-(4-{[6-Amino-5-(4-phenoxy-phenyl)-pyrimidin-4-ylamino]-methyl}-piperidin-1-yl)-propenone (Compound 1) characterized as crystalline form NF5.

In certain embodiments, form NF5 is characterized by one or more 2θ peaks at 4.7, 9.4, and 20.1 degrees. In certain embodiments, form NF5 is characterized by two or more 2θ peaks at 4.7, 9.4, and 20.1 degrees. In certain embodiments, form NF5 is characterized by 2θ peaks at 4.7, 9.4, and 20.1 degrees.

In certain embodiments, form NF5 is characterized by one or more 2θ peaks at 4.7, 9.4, 13.3, 14.2, 17.0, 17.3, 17.5, 20.1, and 21.1 degrees. In certain embodiments, form NF5 is characterized by two or more 2θ peaks at 4.7, 9.4, 13.3, 14.2, 17.0, 17.3, 17.5, 20.1, and 21.1 degrees. In certain embodiments, form NF5 is characterized by three or more 2θ peaks at 4.7, 9.4, 13.3, 14.2, 17.0, 17.3, 17.5, 20.1, and 21.1 degrees. In certain embodiments, form NF5 is characterized by four or more 2θ peaks at 4.7, 9.4, 13.3, 14.2, 17.0, 17.3, 17.5, 20.1, and 21.1 degrees. In certain embodiments, form NF5 is characterized by five or more 2θ peaks at 4.7, 9.4, 13.3, 14.2, 17.0, 17.3, 17.5, 20.1, and 21.1 degrees. In certain embodiments, form NF5 is characterized by six or more 2θ peaks at 4.7, 9.4, 13.3, 14.2, 17.0, 17.3, 17.5, 20.1, and 21.1 degrees. In certain embodiments, form NF5 is characterized by seven or more 2θ peaks at 4.7, 9.4, 13.3, 14.2, 17.0, 17.3, 17.5, 20.1, and 21.1 degrees. In certain embodiments, form NF5 is characterized by 2θ peaks at 4.7, 9.4, 13.3, 14.2, 17.0, 17.3, 17.5, 20.1, and 21.1 degrees.

In certain embodiments, form NF5 is characterized by 2θ peaks at

| No. | °2θ (Cu—Kα$_1$ radiation) ± 0.2° |
|---|---|
| 1 | 4.7 |
| 2 | 9.4 |
| 3 | 13.3 |
| 4 | 14.2 |
| 5 | 15.9 |
| 6 | 17.0 |
| 7 | 17.3 |
| 8 | 17.5 |
| 9 | 18.1 |
| 10 | 18.9 |
| 11 | 20.1 |
| 12 | 21.1 |
| 13 | 23.0 |
| 14 | 23.6 |
| 15 | 24.9 |
| 16 | 25.5 |

In another embodiment, form NF5 is characterized by a diffraction pattern substantially similar to that of FIG. 9.

A Powder X-Ray Diffraction pattern of free base form NF5 was obtained by standard techniques as described in the European Pharmacopeia 6$^{th}$ Edition chapter 2.9.33, and was characterised by the following X-ray powder diffractogram (monochromatic Cu—Kα$_1$ radiation, λ=1.5406 Å, Stoe StadiP 611 KL transmission diffractometer). See Example 6.

In another embodiment, form NF5 is characterized as a crystalline anhydrous form.

Other physical properties of form NF5 include the following: Thermal behavior of form NF5 shows a melting peak onset at approx. 164±2° C. (based on multiple measurements on different samples of form NF5). Thermogravimetric analysis reveals very low weight loss <0.5 wt % up to this temperature. DSC scan of form NF5 was acquired on a Mettler-Toledo DSC 821 with a heating rate of 50 K/min, using nitrogen purge gas at 50 mL/min. TGA scan of form NF5 was acquired on a Mettler-Toledo TGA 851 with a heating rate of 5 K/min, using nitrogen purge gas at 50 mL/min. Water Vapour Sorption behavior of form NF5 reveals small water uptake levels ≤1 wt % in the relative humidity (rh) range 0-90% rh, and very slightly elevated water uptake levels ≤2 wt % at relative humidity (rh) level of 98% rh. Form NF5 can be classified as slightly hygroscopic according to Ph. Eur. Criteria (section 5.11.). Water Vapor Sorption isotherm (25° C.) of Form NF5 is displayed below. Water Vapour Sorption isotherm was acquired on a DVS-Intrinsic system from SMS. Kinetic solubility of form NF5 in Fasted-State Simulated Intestinal Fluid [FaSSIF, pH 6.5] at RT (approx 22° C.) was determined to be approx. 30 μg/mL (after 2 h) and approx. 45 μg/mL (after 4 h), respectively (see example 8a). Overall, free base form NF5 reveals good solid-state properties (good crystallinity, slightly hygroscopic, high thermal stability). Surprisingly, form NF5 exhibits higher kinetic solubility compared to form A1 despite being exceptionally stable upon heating as well as upon exposure to elevated relative humidity levels.

In one embodiment, the invention provides 1-(4-{[6-Amino-5-(4-phenoxy-phenyl)-pyrimidin-4-ylamino]-methyl}-piperidin-1-yl)-propenone (Compound 1) characterized as crystalline form NF6.

In certain embodiments, form NF6 is characterized by one or more 2θ peaks at 4.79, 17.39, and 20.01 degrees. In certain embodiments, form NF6 is characterized by two or more 2θ peaks at 4.79, 17.39, and 20.01 degrees. In certain embodiments, form NF6 is characterized by 2θ peaks at 4.79, 17.39, and 20.01 degrees.

In certain embodiments, form NF6 is characterized by one or more 2θ peaks at 4.79, 9.56, 15.16, 17.39, 20.01, 20.57, 22.10, 23.38, and 23.73 degrees. In certain embodiments, form NF6 is characterized by two or more 2θ peaks at 4.79, 9.56, 15.16, 17.39, 20.01, 20.57, 22.10, 23.38, and 23.73 degrees. In certain embodiments, form NF6 is characterized by three or more 2θ peaks at 4.79, 9.56, 15.16, 17.39, 20.01, 20.57, 22.10, 23.38, and 23.73 degrees. In certain embodiments, form NF6 is characterized by four or more 2θ peaks at 4.79, 9.56, 15.16, 17.39, 20.01, 20.57, 22.10, 23.38, and 23.73 degrees. In certain embodiments, form NF6 is characterized by five or more 2θ peaks at 4.79, 9.56, 15.16, 17.39, 20.01, 20.57, 22.10, 23.38, and 23.73 degrees. In certain embodiments, form NF6 is characterized by six or more 2θ peaks at 4.79, 9.56, 15.16, 17.39, 20.01, 20.57, 22.10, 23.38, and 23.73 degrees. In certain embodiments, form NF6 is characterized by seven or more 2θ peaks at 4.79, 9.56, 15.16, 17.39, 20.01, 20.57, 22.10, 23.38, and 23.73 degrees. In certain embodiments, form NF6 is characterized by 2θ peaks at 4.79, 9.56, 15.16, 17.39, 20.01, 20.57, 22.10, 23.38, and 23.73 degrees.

In certain embodiments, form NF6 is characterized by 2θ peaks at

| No. | °2θ (Cu—K$\alpha_1$ radiation) ± 0.2° |
|---|---|
| 1 | 4.79 |
| 2 | 9.56 |
| 3 | 11.76 |
| 4 | 12.53 |
| 5 | 13.65 |
| 6 | 14.35 |
| 7 | 15.16 |
| 8 | 15.61 |
| 9 | 16.86 |
| 10 | 17.39 |
| 11 | 18.29 |
| 12 | 19.21 |
| 13 | 20.01 |
| 14 | 20.57 |
| 15 | 21.21 |
| 16 | 22.10 |
| 17 | 23.38 |
| 18 | 23.73 |
| 19 | 25.83 |

In another embodiment, form NF6 is characterized by a diffraction pattern substantially similar to that of FIG. 13.

A Powder X-Ray Diffraction pattern of free base form NF6 was obtained by standard techniques as described in the European Pharmacopeia 6$^{th}$ Edition chapter 2.9.33, and was characterised by the following X-ray powder diffractogram (monochromatic Cu—K$\alpha_1$ radiation. λ=1.5406 Å. Stoe StadiP 611 KL transmission diffractometer). See Example 7.

In another embodiment, form NF6 is characterized as a crystalline anhydrous form.

Other physical properties of form NF6 include the following: Thermal behavior of form NF6 shows a melting peak onset at approx. 158±1° C. (based on multiple measurements on one sample of form NF6). Thermogravimetric analysis reveals very low weight loss <0.5 wt % up to this temperature. DSC scan of form NF6 was acquired on a Mettler-Toledo DSC 821 with a heating rate of 50 K/min, using nitrogen purge gas at 50 mL/min. TGA scan of form NF6 was acquired on a Mettler-Toledo TGA 851 with a heating rate of 5 K/min, using nitrogen purge gas at 50 mL/min. Water Vapour Sorption behavior of form NF6 reveals small water uptake levels ≤2 wt % in the relative humidity (rh) range 0-80% rh, and slightly elevated water uptake levels ≤3 wt % in the relative humidity (rh) range 90-98% rh. Form NF6 can be classified as slightly hygroscopic according to Ph. Eur. Criteria (section 5.11.). Water Vapor Sorption isotherm (25° C.) of Form NF6 is displayed below. Water Vapour Sorption isotherm was acquired on a DVS-Intrinsic system from SMS. Kinetic solubility of form NF6 in Fasted-State Simulated Intestinal Fluid [FaSSIF, pH 6.5] at RT (approx 22° C.) was determined to be approx. 95 μg/mL (after 2 h) and approx. 80 μg/mL (after 4 h), respectively (see example 8a). Overall, free base form NF6 reveals good solid-state properties (good crystallinity, slightly hygroscopic, high thermal stability), with very good manufacturability in larger scale. Surprisingly, form NF6 exhibits pronouncedly higher kinetic solubility compared to form A1 despite being exceptionally stable upon heating as well as upon exposure to elevated relative humidity levels.

In one embodiment, the invention provides a malonate salt of 1-(4-{[6-Amino-5-(4-phenoxy-phenyl)-pyrimidin-4-ylamino]-methyl}-piperidin-1-yl)-propenone (Compound 1). In certain embodiments, the invention provides a malonate salt of Compound 1 characterized as Malonate-NF1.

In certain embodiments, form Malonate-NF1 is characterized by one or more 2θ peaks at 7.6, 15.6, and 25.0 degrees. In certain embodiments, form Malonate-NF1 is characterized by two or more 2θ peaks at 7.6, 15.6, and 25.0 degrees. In certain embodiments, form Malonate-NF1 is characterized by 2θ peaks at 7.6, 15.6, and 25.0 degrees.

In certain embodiments, form Malonate-NF1 is characterized by one or more 2θ peaks at 7.6, 12.9, 15.6, 16.2, 20.7, 20.9, 22.4, and 25.0 degrees. In certain embodiments, form Malonate-NF1 is characterized by two or more 2θ peaks at 7.6, 12.9, 15.6, 16.2, 20.7, 20.9, 22.4, and 25.0 degrees. In certain embodiments, form Malonate-NF1 is characterized by three or more 2θ peaks at 7.6, 12.9, 15.6, 16.2, 20.7, 20.9, 22.4, and 25.0 degrees. In certain embodiments, form Malonate-NF1 is characterized by four or more 2θ peaks at 7.6, 12.9, 15.6, 16.2, 20.7, 20.9, 22.4, and 25.0 degrees. In certain embodiments, form Malonate-NF1 is characterized by five or more 2θ peaks at 7.6, 12.9, 15.6, 16.2, 20.7, 20.9, 22.4, and 25.0 degrees. In certain embodiments, form Malonate-NF1 is characterized by six or more 2θ peaks at 7.6, 12.9, 15.6, 16.2, 20.7, 20.9, 22.4, and 25.0 degrees. In certain embodiments, form Malonate-NF1 is characterized by seven or more 2θ peaks at 7.6, 12.9, 15.6, 16.2, 20.7, 20.9, 22.4, and 25.0 degrees. In certain embodiments, form Malonate-NF1 is characterized by 2θ peaks at 7.6, 12.9, 15.6, 16.2, 20.7, 20.9, 22.4, and 25.0 degrees.

In certain embodiments, form Malonate-NF1 is characterized by 2θ peaks at

| No. | °2θ (Cu—Kα₁ radiation) ± 0.2° |
|---|---|
| 1 | 7.4 |
| 2 | 7.6 |
| 3 | 10.7 |
| 4 | 11.5 |
| 5 | 12.9 |
| 6 | 13.3 |
| 7 | 14.0 |
| 8 | 14.6 |
| 9 | 15.3 |
| 10 | 15.6 |
| 11 | 16.2 |
| 12 | 17.3 |
| 13 | 18.1 |
| 14 | 18.7 |
| 15 | 19.2 |
| 16 | 19.7 |
| 17 | 19.9 |
| 18 | 20.7 |
| 19 | 20.9 |
| 20 | 21.4 |
| 21 | 22.4 |
| 22 | 24 |
| 23 | 24.5 |
| 24 | 25.0 |
| 25 | 25.6 |
| 26 | 28.4 |

In another embodiment, form Malonate-NF1 is characterized by a diffraction pattern substantially similar to that of FIG. 17.

A Powder X-Ray Diffraction pattern of Malonate salt form Malonate-NF1 was obtained by standard techniques as described in the European Pharmacopeia 6$^{th}$ Edition chapter 2.9.33, and was characterised by the following X-ray powder diffractogram (monochromatic Cu-Kα₁ radiation. λ=1.5406 Å. Stoe StadiP 611 KL transmission diffractometer). See Example 10a.

In another embodiment, form Malonate-NF1 is characterized as a crystalline anhydrous form.

Other physical properties of form Malonate-NF1 include the following: $^1$H-NMR spectroscopic data reveal a API:Malonate molar ratio of 1:1. Thermal behavior of form Malonate-NF1 shows a melting/decomposition peak onset at approx. 139° C. Thermogravimetric analysis reveals very low weight loss <0.5 wt % up to this temperature. DSC scan of form Malonate-NF1 was acquired on a Mettler-Toledo DSC 821 with a heating rate of 5 K/min, using nitrogen purge gas at 50 mL/min. TGA scan of form Malonate-NF1 was acquired on a Mettler-Toledo TGA 851 with a heating rate of 5 K/min, using nitrogen purge gas at 50 mL/min. Water Vapour Sorption behavior of form Malonate-NF1 reveals very small water uptake levels <0.5 wt % in the relative humidity (rh) range 0-80% rh. Form Malonate-NF1 can be classified as slightly hygroscopic according to Ph. Eur. Criteria (section 5.11.). Reduced Water Vapour Sorption isotherm (25° C.) of Form Malonate-NF1 (with adsorption levels at 40% rh and 80% rh) is displayed below. Water Vapour Sorption isotherm was acquired on a DVS-Intrinsic system from SMS. Dissolution level of form Malonate-NF1 in Fasted-State Simulated Intestinal Fluid [FaSSIF, pH 6.5] at 37° C. was determined to be approx. 75 µg/mL (after 2 h), and dissolution level of form Malonate-NF1 in Fed-State Simulated Intestinal Fluid [FeSSIF, pH 5.0] at 37° C. was determined to be approx. 740 µg/mL (after 2 h), respectively, by far exceeding corresponding dissolution levels of free base form A1 (see example 11). Overall, form Malonate-NF1 reveals very good solid-state properties (good crystallinity, slightly hygroscopic, high thermal stability). Surprisingly, form Malonate-NF1 exhibits pronouncedly higher kinetic solubility compared to free base form A1 in combination with low tendency for hygroscopicity and hydrate/solvate formation.

In one embodiment, the invention provides a succinate salt of 1-(4-{[6-Amino-5-(4-phenoxy-phenyl)-pyrimidin-4-ylamino]-methyl}-piperidin-1-yl)-propenone (Compound 1). In certain embodiments, the invention provides a succinate salt of Compound 1 characterized as Succinate-NF1.

In certain embodiments, form Succinate-NF1 is characterized by one or more 2θ peaks at 6.7, 19.2, and 20.7 degrees. In certain embodiments, form Succinate-NF1 is characterized by two or more 2θ peaks at 6.7, 19.2, and 20.7 degrees. In certain embodiments, form Succinate-NF1 is characterized by 2θ peaks at 6.7, 19.2, and 20.7 degrees.

In certain embodiments, form Succinate-NF1 is characterized by one or more 2θ peaks at 6.7, 14.7, 15.5, 19.2, 20.7, 21.6, and 21.9 degrees. In certain embodiments, form Succinate-NF1 is characterized by two or more 2θ peaks at 6.7, 14.7, 15.5, 19.2, 20.7, 21.6, and 21.9 degrees. In certain embodiments, form Succinate-NF1 is characterized by three or more 2θ peaks at 6.7, 14.7, 15.5, 19.2, 20.7, 21.6, and 21.9 degrees. In certain embodiments, form Succinate-NF1 is characterized by four or more 2θ peaks at 6.7, 14.7, 15.5, 19.2, 20.7, 21.6, and 21.9 degrees. In certain embodiments, form Succinate-NF1 is characterized by five or more 2θ peaks at 6.7, 14.7, 15.5, 19.2, 20.7, 21.6, and 21.9 degrees. In certain embodiments, form Succinate-NF1 is characterized by six or more 2θ peaks at 6.7, 14.7, 15.5, 19.2, 20.7, 21.6, and 21.9 degrees. In certain embodiments, form Succinate-NF1 is characterized by 2θ peaks at 6.7, 14.7, 15.5, 19.2, 20.7, 21.6, and 21.9 degrees.

In certain embodiments, form Succinate-NF1 is characterized by 2θ peaks at

| No. | °2θ (Cu—Kα₁ radiation) ± 0.2° |
|---|---|
| 1 | 6.2 |
| 2 | 6.7 |
| 3 | 8.0 |
| 4 | 8.3 |
| 5 | 12.6 |
| 6 | 14.4 |
| 7 | 14.7 |
| 8 | 15.1 |
| 9 | 15.5 |
| 10 | 16.5 |
| 11 | 17.6 |
| 12 | 18.2 |
| 13 | 19.2 |
| 14 | 20.1 |
| 15 | 20.7 |
| 16 | 21.0 |
| 17 | 21.6 |
| 18 | 21.9 |
| 19 | 23.0 |
| 20 | 23.3 |
| 21 | 23.8 |
| 22 | 24.8 |

In another embodiment, form Succinate-NF1 is characterized by a diffraction pattern substantially similar to that of FIG. 21.

A Powder X-Ray Diffraction pattern of Succinate-NF1 was obtained by standard techniques as described in the European Pharmacopeia 6$^{th}$ Edition chapter 2.9.33, and was characterised by the following X-ray powder diffractogram (monochromatic Cu—Kα₁ radiation, λ=1.5406 Å. Stoe StadiP 611 KL transmission diffractometer). See Example 10b.

In another embodiment, form Succinate-NF1 is characterized as a crystalline anhydrous form.

Other physical properties of form Succinate-NF1 include the following: ¹H-NMR spectroscopic data reveal a API:Succinate molar ratio of 1:1. Thermal behavior of form Succinate-NF1 shows a melting/decomposition peak onset at approx. 122° C. Thermogravimetric analysis reveals low weight loss <1.0 wt % up to this temperature. DSC scan of form Succinate-NF1 was acquired on a Mettler-Toledo DSC 821 with a heating rate of 5 K/min, using nitrogen purge gas at 50 mL/min. TGA scan of form Succinate-NF1 was acquired on a Mettler-Toledo TGA 851 with a heating rate of 5 K/min, using nitrogen purge gas at 50 mL/min. Water Vapour Sorption behavior of form Succinate-NF1 reveals small water uptake levels ≤2.0 wt % in the relative humidity (rh) range 0-80% rh. Form Succinate-NF1 can be classified as slightly hygroscopic according to Ph. Eur. Criteria (section 5.11.). Reduced Water Vapour Sorption isotherm (25° C.) of Form Succinate-NF1 (with adsorption levels at 40% rh and 80% rh) is displayed below. Water Vapour Sorption isotherm was acquired on a DVS-Intrinsic system from SMS. Dissolution level of form Succinate-NF1 in Fasted-State Simulated Intestinal Fluid [FaSSIF, pH 6.5] at 37° C. was determined to be approx. 100 μg/mL (after 2 h), and dissolution level of form Succinate-NF1 in Fed-State Simulated Intestinal Fluid [FeSSIF, pH 5.0] at 37° C. was determined to be approx. 743 μg/mL (after 2 h), respectively, by far exceeding corresponding dissolution levels of free base form A1 (see example 11). Overall, form Succinate-NF1 reveals very good solid-state properties (good crystallinity, slightly hygroscopic, high thermal stability). Surprisingly, form Succinate-NF1 exhibits pronouncedly higher kinetic solubility compared to free base form A1 in combination with low tendency for hygroscopicity and hydrate/solvate formation.

In one embodiment, the invention provides an oxalate salt of 1-(4-{[6-Amino-5-(4-phenoxy-phenyl)-pyrimidin-4-ylamino]-methyl}-piperidin-1-yl)-propenone (Compound 1). In certain embodiments, the invention provides an oxalate salt of Compound 1 characterized as Oxalate-NF1.

In certain embodiments, form Oxalate-NF1 is characterized by one or more 2θ peaks at 7.5, 17.8, and 19.5 degrees. In certain embodiments, form Oxalate-NF1 is characterized by two or more 2θ peaks at 7.5, 17.8, and 19.5 degrees. In certain embodiments, form Oxalate-NF1 is characterized by 2θ peaks at 7.5, 17.8, and 19.5 degrees.

In certain embodiments, form Oxalate-NF1 is characterized by one or more 2θ peaks at 7.5, 9.0, 16.1, 17.3, 17.8, 19.5, 20.3, and 23.8 degrees. In certain embodiments, form Oxalate-NF1 is characterized by two or more 2θ peaks at 7.5, 9.0, 16.1, 17.3, 17.8, 19.5, 20.3, and 23.8 degrees. In certain embodiments, form Oxalate-NF1 is characterized by three or more 2θ peaks at 7.5, 9.0, 16.1, 17.3, 17.8, 19.5, 20.3, and 23.8 degrees. In certain embodiments, form Oxalate-NF1 is characterized by four or more 2θ peaks at 7.5, 9.0, 16.1, 17.3, 17.8, 19.5, 20.3, and 23.8 degrees. In certain embodiments, form Oxalate-NF1 is characterized by five or more 2θ peaks at 7.5, 9.0, 16.1, 17.3, 17.8, 19.5, 20.3, and 23.8 degrees. In certain embodiments, form Oxalate-NF1 is characterized by six or more 2θ peaks at 7.5, 9.0, 16.1, 17.3, 17.8, 19.5, 20.3, and 23.8 degrees. In certain embodiments, form Oxalate-NF1 is characterized by 2θ peaks at 7.5, 9.0, 16.1, 17.3, 17.8, 19.5, 20.3, and 23.8 degrees.

In certain embodiments, form Oxalate-NF1 is characterized by 2θ peaks at

| No. | °2θ (Cu—Kα₁ radiation) ± 0.2° |
|---|---|
| 1 | 7.5 |
| 2 | 9.0 |
| 3 | 11.7 |
| 4 | 15.1 |
| 5 | 15.5 |
| 6 | 15.8 |
| 7 | 16.1 |
| 8 | 17.3 |
| 9 | 17.8 |
| 10 | 17.9 |
| 11 | 19.5 |
| 12 | 20.3 |
| 13 | 20.5 |
| 14 | 21.7 |
| 15 | 23.4 |
| 16 | 23.5 |
| 17 | 23.8 |
| 18 | 24.5 |
| 19 | 25.0 |
| 20 | 25.7 |

In another embodiment, form Oxalate-NF1 is characterized by a diffraction pattern substantially similar to that of FIG. 25.

A Powder X-Ray Diffraction pattern of Oxalate-NF1 was obtained by standard techniques as described in the European Pharmacopeia 6ᵗʰ Edition chapter 2.9.33, and was characterised by the following X-ray powder diffractogram (monochromatic Cu—Kα₁ radiation, λ=1.5406 Å, Stoe StadiP 611 KL transmission diffractometer). See Example 10c.

In another embodiment, form Oxalate-NF1 is characterized as a crystalline anhydrous form.

Other physical properties of form Oxalate-NF1 include the following: ¹³C-NMR spectroscopic data reveal a API:Oxalate molar ratio of 1:1.1. Thermal behavior of form Oxalate-NF1 shows a melting/decomposition peak onset at approx. 188° C. Thermogravimetric analysis reveals very low weight loss <0.5 wt % up to this temperature. DSC scan of form Oxalate-NF1 was acquired on a Mettler-Toledo DSC 821 with a heating rate of 5 K/min, using nitrogen purge gas at 50 mL/min. TGA scan of form Oxalate-NF1 was acquired on a Mettler-Toledo TGA 851 with a heating rate of 5 K/min, using nitrogen purge gas at 50 mL/min. Water Vapour Sorption behavior of form Oxalate-NF1 reveals small water uptake levels <1.0 wt % in the relative humidity (rh) range 0-80% rh. Form Oxalate-NF1 can be classified as slightly hygroscopic according to Ph. Eur. Criteria (section 5.11.). Reduced Water Vapour Sorption isotherm (25° C.) of Form Oxalate-NF1 (with adsorption levels at 40% rh and 80% rh) is displayed below. Water Vapour Sorption isotherm was acquired on a DVS-Intrinsic system from SMS. Dissolution level of form Oxalate-NF1 in Fasted-State Simulated Intestinal Fluid [FaSSIF, pH 6.5] at 37° C. was determined to be approx. 58 μg/mL (after 2 h), and dissolution level of form Oxalate-NF1 in Fed-State Simulated Intestinal Fluid [FeSSIF, pH 5.0] at 37° C. was determined to be approx. 740 μg/mL (after 2 h), respectively, by far exceeding corresponding dissolution levels of free base form A1 (see example 11). Overall, form Oxalate-NF1 reveals very good solid-state properties (good crystallinity, slightly hygroscopic, high thermal stability). Surprisingly, form Oxalate-NF1 exhibits pronouncedly higher kinetic solubility compared to free base form A1 in combination with low tendency for hygroscopicity and hydrate/solvate formation.

In one embodiment, the invention provides a fumarate salt of 1-(4-{[6-Amino-5-(4-phenoxy-phenyl)-pyrimidin-4-ylamino]-methyl}-piperidin-1-yl)-propenone (Compound 1). In certain embodiments, the invention provides a fumarate salt of Compound 1 characterized as Fumarate-NF1.

In certain embodiments, form Fumarate-NF1 is characterized by one or more 2θ peaks at 6.7, 19.3, and 20.8 degrees. In certain embodiments, form Fumarate-NF1 is characterized by two or more 2θ peaks at 6.7, 19.3, and 20.8 degrees. In certain embodiments, form Fumarate-NF1 is characterized by 2θ peaks at 6.7, 19.3, and 20.8 degrees.

In certain embodiments, form Fumarate-NF1 is characterized by one or more 2θ peaks at 6.7, 14.8, 15.2, 16.7, 18.3, 19.3, and 20.8 degrees. In certain embodiments, form Fumarate-NF1 is characterized by two or more 2θ peaks at 6.7, 14.8, 15.2, 16.7, 18.3, 19.3, and 20.8 degrees. In certain embodiments, form Fumarate-NF1 is characterized by three or more 2θ peaks at 6.7, 14.8, 15.2, 16.7, 18.3, 19.3, and 20.8 degrees. In certain embodiments, form Fumarate-NF1 is characterized by four or more 2θ peaks at 6.7, 14.8, 15.2, 16.7, 18.3, 19.3, and 20.8 degrees. In certain embodiments, form Fumarate-NF1 is characterized by five or more 2θ peaks at 6.7, 14.8, 15.2, 16.7, 18.3, 19.3, and 20.8 degrees. In certain embodiments, form Fumarate-NF1 is characterized by six or more 2θ peaks at 6.7, 14.8, 15.2, 16.7, 18.3, 19.3, and 20.8 degrees. In certain embodiments, form Fumarate-NF1 is characterized by 2θ peaks at 6.7, 14.8, 15.2, 16.7, 18.3, 19.3, and 20.8 degrees.

In certain embodiments, form Fumarate-NF1 is characterized by 2θ peaks at

| No. | °2θ (Cu—Kα₁ radiation) ± 0.2° |
|---|---|
| 1 | 6.2 |
| 2 | 6.7 |
| 3 | 7.9 |
| 4 | 8.3 |
| 5 | 9.9 |
| 6 | 12.7 |
| 7 | 14.8 |
| 8 | 15.2 |
| 9 | 15.6 |
| 10 | 15.9 |
| 11 | 16.7 |
| 12 | 18.3 |
| 13 | 19.3 |
| 14 | 20.7 |
| 15 | 20.8 |
| 16 | 21.5 |
| 17 | 23.1 |
| 18 | 23.4 |
| 19 | 23.8 |
| 20 | 24.9 |
| 21 | 27.2 |

In another embodiment, form Fumarate-NF1 is characterized by a diffraction pattern substantially similar to that of FIG. 29.

A Powder X-Ray Diffraction pattern of Fumarate-NF1 was obtained by standard techniques as described in the European Pharmacopeia 6th Edition chapter 2.9.33, and was characterised by the following X-ray powder diffractogram (monochromatic Cu—Kα₁ radiation, λ=1.5406 Å, Stoe StadiP 611 KL transmission diffractometer). See Example 10d.

In another embodiment, form Fumarate-NF1 is characterized as a crystalline anhydrous form.

Other physical properties of form Fumarate-NF1 include the following: ¹H-NMR spectroscopic data reveal a API: Fumarate molar ratio of 1:1. Thermal behavior of form Fumarate-NF1 shows a melting/decomposition peak onset at approx. 175° C. Thermogravimetric analysis reveals low weight loss <1.0 wt % up to this temperature. DSC scan of form Fumarate-NF1 was acquired on a Mettler-Toledo DSC 821 with a heating rate of 5 K/min, using nitrogen purge gas at 50 mL/min. TGA scan of form Fumarate-NF1 was acquired on a Mettler-Toledo TGA 851 with a heating rate of 5 K/min, using nitrogen purge gas at 50 mL/min. Water Vapour Sorption behavior of form Fumarate-NF1 reveals very small water uptake levels <0.5 wt % in the relative humidity (rh) range 0-80% rh. Form Fumarate-NF1 can be classified as slightly hygroscopic according to Ph. Eur. Criteria (section 5.11.). Reduced Water Vapour Sorption isotherm (25° C.) of Form Fumarate-NF1 (with adsorption levels at 40% rh and 80% rh) is displayed below. Water Vapour Sorption isotherm was acquired on a DVS-Intrinsic system from SMS. Overall, form Fumarate-NF1 reveals very good solid-state properties (good crystallinity, slightly hygroscopic, high thermal stability).

In one embodiment, the invention provides a maleate salt of 1-(4-{[6-Amino-5-(4-phenoxy-phenyl)-pyrimidin-4-ylamino]-methyl}-piperidin-1-yl)-propenone (Compound 1). In certain embodiments, the invention provides a maleate salt of Compound 1 characterized as Maleate-NF1.

In certain embodiments, form Maleate-NF1 is characterized by one or more 2θ peaks at 17.9, 19.0, and 24.7 degrees. In certain embodiments, form Maleate-NF1 is characterized by two or more 2θ peaks at 17.9, 19.0, and 24.7 degrees. In certain embodiments, form Maleate-NF1 is characterized by 2θ peaks at 17.9, 19.0, and 24.7 degrees.

In certain embodiments, form Maleate-NF1 is characterized by one or more 2θ peaks at 10.5, 11.5, 17.9, 18.4, 19.0, 20.3, 20.5, and 24.7 degrees. In certain embodiments, form Maleate-NF1 is characterized by two or more 2θ peaks at 10.5, 11.5, 17.9, 18.4, 19.0, 20.3, 20.5, and 24.7 degrees. In certain embodiments, form Maleate-NF1 is characterized by three or more 2θ peaks at 10.5, 11.5, 17.9, 18.4, 19.0, 20.3, 20.5, and 24.7 degrees. In certain embodiments, form Maleate-NF1 is characterized by four or more 2θ peaks at 10.5, 11.5, 17.9, 18.4, 19.0, 20.3, 20.5, and 24.7 degrees. In certain embodiments, form Maleate-NF1 is characterized by five or more 2θ peaks at 10.5, 11.5, 17.9, 18.4, 19.0, 20.3, 20.5, and 24.7 degrees. In certain embodiments, form Maleate-NF1 is characterized by six or more 2θ peaks at 10.5, 11.5, 17.9, 18.4, 19.0, 20.3, 20.5, and 24.7 degrees. In certain embodiments, form Maleate-NF1 is characterized by 2θ peaks at 10.5, 11.5, 17.9, 18.4, 19.0, 20.3, 20.5, and 24.7 degrees.

In certain embodiments, form Maleate-NF1 is characterized by 2θ peaks at

| No. | °2θ (Cu—Kα₁ radiation) ± 0.2° |
|---|---|
| 1 | 9.5 |
| 2 | 10.5 |
| 3 | 11.5 |
| 4 | 12.9 |
| 5 | 15.0 |
| 6 | 15.9 |
| 7 | 17.1 |
| 8 | 17.3 |
| 9 | 17.9 |
| 10 | 18.4 |
| 11 | 19.0 |
| 12 | 19.8 |
| 13 | 20.3 |
| 14 | 20.5 |
| 15 | 21.3 |
| 16 | 21.7 |

-continued

| No. | °2θ (Cu—Kα₁ radiation) ± 0.2° |
|---|---|
| 17 | 22.7 |
| 18 | 24.7 |
| 19 | 25.2 |
| 20 | 26.8 |

In another embodiment, form Maleate-NF1 is characterized by a diffraction pattern substantially similar to that of FIG. 33.

A Powder X-Ray Diffraction pattern of Maleate-NF1 was obtained by standard techniques as described in the European Pharmacopeia 6 Edition chapter 2.9.33, and was characterised by the following X-ray powder diffractogram (monochromatic Cu—Kα₁ radiation, λ=1.5406 Å, Stoe StadiP 611 KL transmission diffractometer). See Example 10e.

In another embodiment, form Maleate-NF1 is characterized as a crystalline anhydrous form.

Other physical properties of form Maleate-NF1 include the following: $^1$H-NMR spectroscopic data reveal a API:Maleate molar ratio of 1:1. Thermal behavior of form Maleate-NF1 shows a melting/decomposition peak onset at approx. 163° C. Thermogravimetric analysis reveals low weight loss <1.0 wt % up to this temperature. DSC scan of form Maleate-NF1 was acquired on a Mettler-Toledo DSC 821 with a heating rate of 5 K/min, using nitrogen purge gas at 50 mL/min. TGA scan of form Maleate-NF1 was acquired on a Mettler-Toledo TGA 851 with a heating rate of 5 K/min, using nitrogen purge gas at 50 mL/min. Water Vapour Sorption behavior of form Maleate-NF1 reveals very small water uptake levels <0.5 wt % in the relative humidity (rh) range 0-80% rh. Form Maleate-NF1 can be classified as non-hygroscopic according to Ph. Eur. Criteria (section 5.11.). Reduced Water Vapour Sorption isotherm (25° C.) of Form Maleate-NF1 (with adsorption levels at 40% rh and 80% rh) is displayed below. Water Vapour Sorption isotherm was acquired on a DVS-Intrinsic system from SMS. Overall, form Maleate-NF1 reveals very good solid-state properties (good crystallinity, non-hygroscopic, high thermal stability).

In one embodiment, the invention provides a citrate salt of 1-(4-{[6-Amino-5-(4-phenoxy-phenyl)-pyrimidin-4-ylamino]-methyl}-piperidin-1-yl)-propenone (Compound 1). In certain embodiments, the invention provides a citrate salt of Compound 1 characterized as Citrate-NF1.

In certain embodiments, form Citrate-NF1 is characterized by one or more 2θ peaks at 7.5, 15.0, and 16.3 degrees. In certain embodiments, form Citrate-NF1 is characterized by two or more 2θ peaks at 7.5, 15.0, and 16.3 degrees. In certain embodiments, form Citrate-NF1 is characterized by 2θ peaks at 7.5, 15.0, and 16.3 degrees.

In certain embodiments, form Citrate-NF1 is characterized by one or more 2θ peaks at 7.5, 12.1, 13.8, 15.0, 16.3, 17.7, 20.3, and 20.8 degrees. In certain embodiments, form Citrate-NF1 is characterized by two or more 2θ peaks at 7.5, 12.1, 13.8, 15.0, 16.3, 17.7, 20.3, and 20.8 degrees. In certain embodiments, form Citrate-NF1 is characterized by three or more 2θ peaks at 7.5, 12.1, 13.8, 15.0, 16.3, 17.7, 20.3, and 20.8 degrees. In certain embodiments, form Citrate-NF1 is characterized by four or more 2θ peaks at 7.5, 12.1, 13.8, 15.0, 16.3, 17.7, 20.3, and 20.8 degrees. In certain embodiments, form Citrate-NF1 is characterized by five or more 2θ peaks at 7.5, 12.1, 13.8, 15.0, 16.3, 17.7, 20.3, and 20.8 degrees. In certain embodiments, form Citrate-NF1 is characterized by six or more 2θ peaks at 7.5, 12.1, 13.8, 15.0, 16.3, 17.7, 20.3, and 20.8 degrees. In certain embodiments, form Citrate-NF1 is characterized by 2θ peaks at 7.5, 12.1, 13.8, 15.0, 16.3, 17.7, 20.3, and 20.8 degrees.

In certain embodiments, form Citrate-NF1 is characterized by 2θ peaks at

| No. | °2θ (Cu—Kα₁ radiation) ± 0.2° |
|---|---|
| 1 | 7.5 |
| 2 | 9.3 |
| 3 | 10.0 |
| 4 | 12.1 |
| 5 | 13.8 |
| 6 | 15.0 |
| 7 | 15.5 |
| 8 | 16.3 |
| 9 | 16.6 |
| 10 | 17.7 |
| 11 | 18.1 |
| 12 | 18.7 |
| 13 | 20.0 |
| 14 | 20.3 |
| 15 | 20.8 |
| 16 | 21.1 |
| 17 | 21.6 |
| 18 | 22.2 |
| 19 | 22.6 |
| 20 | 22.9 |

In another embodiment, form Citrate-NF1 is characterized by a diffraction pattern substantially similar to that of FIG. 37.

A Powder X-Ray Diffraction pattern of Citrate-NF1 was obtained by standard techniques as described in the European Pharmacopeia 6$^{th}$ Edition chapter 2.9.33, and was characterised by the following X-ray powder diffractogram (monochromatic Cu—Kα₁ radiation. λ=1.5406 Å. Stoe StadiP 611 KL transmission diffractometer). See Example 10f.

In another embodiment, form Citrate-NF1 is characterized as a crystalline anhydrous form.

Other physical properties of form Citrate-NF1 include the following: $^1$H-NMR spectroscopic data reveal a API:Citrate molar ratio of 1:1. Thermal behavior of form Citrate-NF1 shows a melting/decomposition peak onset at approx. 134° C. Thermogravimetric analysis reveals a weight loss of ~4.0 wt % up to this temperature. DSC scan of form Citrate-NF1 was acquired on a Mettler-Toledo DSC 821 with a heating rate of 5 K/min, using nitrogen purge gas at 50 mL/min. TGA scan of form Citrate-NF1 was acquired on a Mettler-Toledo TGA 851 with a heating rate of 5 K/min, using nitrogen purge gas at 50 mL/min. Water Vapour Sorption behavior of form Citrate-NF1 reveals small water uptake levels <2.0 wt % in the relative humidity (rh) range 0-80% rh. Form Citrate-NF1 can be classified as slightly hygroscopic according to Ph. Eur. Criteria (section 5.11.). Reduced Water Vapour Sorption isotherm (25° C.) of Form Citrate-NF1 (with adsorption levels at 40% rh and 80% rh) is displayed below. Water Vapour Sorption isotherm was acquired on a DVS-Intrinsic system from SMS. Overall, form Citrate-NF1 reveals acceptable solid-state properties (good crystallinity, non-hygroscopic, acceptable thermal stability).

In one embodiment, the invention provides 1-(4-{[6-Amino-5-(4-phenoxy-phenyl)-pyrimidin-4-ylamino]-methyl}-piperidin-1-yl)-propenone (Compound 1) characterized as crystalline form A1.

In certain embodiments, form A1 is characterized by one or more 2θ peaks at 4.8, 17.4, and 20.0 degrees. In certain embodiments, form A1 is characterized by two or more 2θ peaks at 4.8, 17.4, and 20.0 degrees. In certain embodiments, form A1 is characterized by 2θ peaks at 4.8, 17.4, and 20.0 degrees.

In certain embodiments, form A1 is characterized by one or more 2θ peaks at 4.8, 9.5, 15.1, 17.4, 18.1, 20.0, and 23.8 degrees. In certain embodiments, form A1 is characterized by two or more 2θ peaks at 4.8, 9.5, 15.1, 17.4, 18.1, 20.0, and 23.8 degrees. In certain embodiments, form A1 is characterized by three or more 2θ peaks at 4.8, 9.5, 15.1, 17.4, 18.1, 20.0, and 23.8 degrees. In certain embodiments, form A1 is characterized by four or more 2θ peaks at 4.8, 9.5, 15.1, 17.4, 18.1, 20.0, and 23.8 degrees. In certain embodiments, form A1 is characterized by five or more 2θ peaks at 4.8, 9.5, 15.1, 17.4, 18.1, 20.0, and 23.8 degrees. In certain embodiments, form A1 is characterized by six or more 2θ peaks at 4.8, 9.5, 15.1, 17.4, 18.1, 20.0, and 23.8 degrees. In certain embodiments, form A1 is characterized by seven or more 2θ peaks at 4.8, 9.5, 15.1, 17.4, 18.1, 20.0, and 23.8 degrees. In certain embodiments, form A1 is characterized by 2θ peaks at 4.8, 9.5, 15.1, 17.4, 18.1, 20.0, and 23.8 degrees.

In certain embodiments, form A1 is characterized by 2θ peaks at

| No. | °2θ (Cu—K$\alpha_1$ radiation) ± 0.2° |
|---|---|
| 1 | 4.8 |
| 2 | 9.5 |
| 3 | 11.7 |
| 4 | 12.1 |
| 5 | 13.1 |
| 6 | 14.3 |
| 7 | 15.1 |
| 8 | 16.8 |
| 9 | 17.4 |
| 10 | 18.1 |
| 11 | 18.5 |
| 12 | 19.1 |
| 13 | 20.0 |
| 14 | 20.3 |
| 15 | 21.5 |
| 16 | 22.2 |
| 17 | 22.8 |
| 18 | 23.5 |
| 19 | 23.8 |
| 20 | 25.5 |
| 21 | 28.0 |

In another embodiment, form A1 is characterized by a diffraction pattern substantially similar to that of FIG. 41.

A Powder X-Ray Diffraction pattern of free base form A1 was obtained by standard techniques as described in the European Pharmacopeia 6$^{th}$ Edition chapter 2.9.33, and was characterised by the following X-ray powder diffractogram (monochromatic Cu—Kat radiation, λ=1.5406 Å, Stoe StadiP 611 KL transmission diffractometer). See Example 3.

In certain embodiments, form A1 is crystallises in the monoclinic space group P2$_1$ with the lattice parameters (at 200 K) a=12.8±0.1 Å, b=9.4±0.1 Å, c=37.3±0.2 Å, and β=98.5±0.5° (with α=γ=900). From the single crystal structure, form A1 represents an anhydrous form. Single crystal X-Ray Structure data were obtained on free base form A1 as well (SuperNova diffractometer from Agilent, equipped with CCD Detector using Cu K$_\alpha$ radiation at 200 K).

In another embodiment, form A1 is characterized is a crystalline anhydrous form.

Other physical properties of form A1 include the following: Thermal behavior of form A1 shows a melting peak onset at approx. 171±2° C. (based on multiple measurements on different samples of form A1). Thermogravimetric analysis reveals very low weight loss <1 wt % up to this temperature. DSC scan of form A1 was acquired on a Mettler-Toledo DSC 821 with a heating rate of 50 K/min, using nitrogen purge gas at 50 mL/min. TGA scan of form A1 was acquired on a Mettler-Toledo TGA 851 with a heating rate of 5 K/min, using nitrogen purge gas at 50 mL/min. Water Vapour Sorption behavior of form A1 reveals small water uptake levels ≤1 wt % in the relative humidity (rh) range 0-80% rh, and very slightly elevated water uptake levels ≤2 wt % in the relative humidity (rh) range 90-98% rh. Form A1 can be classified as slightly hygroscopic according to Ph. Eur. Criteria (section 5.11.). Water Vapor Sorption isotherm (25° C.) of form A1 is displayed below. Water Vapour Sorption isotherm was acquired on a DVS-Intrinsic system from SMS. Kinetic solubility of form A1 in Fasted-State Simulated Intestinal Fluid [FaSSIF, pH 6.5] at RT (approx 22° C.) was determined to be approx. 27 µg/mL (after 2 h) and approx. 28 µg/mL (after 4 h), respectively (see example 8a). Thermodynamic solubility (24 h) of form A1 at 37° C. was determined to be approx. 21 µg/mL in Fasted-State Simulated Intestinal Fluid [FaSSIF, pH 6.5], and approx. 14 µg/mL in USP Phosphate buffer [pH 7.4], respectively (see example 8b). Dissolution level of form A1 in Fasted-State Simulated Intestinal Fluid [FaSSIF, pH 6.5] at 37° C. was determined to be approx. 36 µg/mL (after 2 h), and dissolution level of form A1 in Fed-State Simulated Intestinal Fluid [FeSSIF, pH 5.0] at 37° C. was determined to be approx. 214 µg/mL (after 2 h), respectively (see example 11). Overall, free base form A1 reveals good solid-state properties (good crystallinity, slightly hygroscopic, high thermal stability) with very good manufacturability in larger scale.

In one embodiment, the invention provides 1-(4-{[6-Amino-5-(4-phenoxy-phenyl)-pyrimidin-4-ylamino]-methyl}-piperidin-1-yl)-propenone (Compound 1) characterized as a mixture of crystalline forms A1 and A2.

The development of solid-state preparation routes was mainly based on solvent crystallisation approaches to enable scalability to large scale as well as providing powder material with good manufacturability properties. However, it was revealed in several initial crystallisation attempts that apparently phase mixtures of known Form A1 and an unknown additional phase were obtained (see Example 2).

A mixture of morphic forms is not favorable from a regulatory and quality perspective, as phase compositions of mixtures are challenging to control from batch to batch. Variability of phase compositions requires extensive characterisation to assess impact on critical quality attributes (e.g. oral absorption behavior, stability behavior) and may also jeopardise robust DP manufacturability if parameters such as particle habit are different for different forms and mixtures thereof.

Surprisingly, the invention provides preparation routes for phase-pure crystalline form A1 of the 1-(4-{[6-Amino-5-(4-phenoxy-phenyl)-pyrimidin-4-ylamino]-methyl}-piperidin-1-yl)-propenone parent entity, which provides powder material with good manufacturability properties in large scale (see Example 3). Various novel phase-pure crystalline forms of the invention (e.g., Forms A2, NF4, NF5, NF6) of 1-(4-{[6-Amino-5-(4-phenoxy-phenyl)-pyrimidin-4-ylamino]-methyl}-piperidin-1-yl)-propenone (see Examples 4, 5, 6, and 7), exhibit beneficial solid state properties, including improved intestinal solubility, relative to Form A1 (see Example 8).

The invention also provides for novel salt forms with improved solid-state properties of 1-(4-{[6-Amino-5-(4-phenoxy-phenyl)-pyrimidin-4-ylamino]-methyl}-piperidin- 1-yl)-propenone to overcome the challenges associated with morphic form mixtures of the Free Base entity. Initial salt formation experiments with different strong mineralic acids (Hydrochloric Acid, Sulfuric Acid, Phosphoric Acid) as well as with organic acids representing a diversity of structures (aliphatic carboxylic monoprotic acids [Formic Acid, Acetic Acid], aliphatic carboxylic diprotic acid [L-Tartaric Acid], aromatic carboxylic acid [Benzoic Acid], amino acid [S-Glutamic Acid]) were attempted, no successful salt formation was obtained. This indicates that salt formation behavior of 1-(4-{[6-Amino-5-(4-phenoxy-phenyl)-pyrimidin-4-ylamino]-methyl}-piperidin-1-yl)-propenone is highly challenging (see Example 9).

Surprisingly, the invention also provides novel crystalline salt forms (e.g., Malonate-NF1, Succinate-NF1, Oxalate-NF1, Fumarate-NF1. Maleate-NF1, L-Malate-NF1, Citrate-NF1) of 1-(4-{[6-Amino-5-(4-phenoxy-phenyl)-pyrimidin-4-ylamino]-methyl}-piperidin-1-yl)-propenone (see Example 10), which exhibit good beneficial solid state properties, including improved intestinal dissolution behavior, for different kind of applications (see Example 11).

In another aspect, the invention features a pharmaceutical composition comprising any of the forms and salts described above, and a pharmaceutically acceptable carrier. In another embodiment, the pharmaceutical composition further comprises an additional therapeutic agent.

In another aspect, the invention features a process of preparing Form A2 comprising dissolving Compound 1 in an alcohol, water, or a mixture thereof.

In certain embodiments, the process comprises a mixture of alcohol and water. In certain embodiments, the alcohol is methanol, ethanol, propanol or butanol.

In certain embodiments, the alcohol is methanol. In certain embodiments, the v:v ratio of methanol:water is about 20:1. In certain embodiments, the v:v ratio of methanol:water is about 10:1. In certain embodiments, the v:v ratio of methanol:water is about 5:1. In certain embodiments, the v:v ratio of methanol:water is about 2:1. In certain embodiments, the v:v ratio of methanol:water is about 1:20. In certain embodiments, the v:v ratio of methanol:water is about 1:10. In certain embodiments, the v:v ratio of methanol:water is about 1:5. In certain embodiments, the v:v ratio of methanol:water is about 1:2. In certain embodiments, the v:v ratio of methanol:water is 1:1.

In certain embodiments, Compound 1 is dissolved at a temperature ranging from about rt to about 100° C. In certain embodiments, Compound 1 is dissolved at a temperature ranging from about rt to about 75° C. In certain embodiments, Compound 1 is dissolved at a temperature ranging from about 25° C. to about 75° C. In certain embodiments, Compound 1 is dissolved at a temperature of about 50° C.

In certain embodiments, the process comprises an alcohol then a second solvent. In certain embodiments, the alcohol is methanol, ethanol, propanol or butanol. In certain embodiments, the alcohol is ethanol. In certain embodiments, the second solvent is water.

In certain embodiments. Compound 1 is dissolved at a temperature ranging from about rt to about 100° C. In certain embodiments, Compound 1 is dissolved at a temperature ranging from about rt to about 75° C. In certain embodiments. Compound 1 is dissolved at a temperature ranging from about 25° C. to about 75° C. In certain embodiments, Compound 1 is dissolved at a temperature of about 50° C.

In another aspect, the invention features a process of preparing Form NF4 comprising dissolving Compound 1 in dichloromethane, chloroform, cyclohexane, heptane, THF, water, or a mixture thereof.

In certain embodiments, the process comprises a mixture of dichloromethane and cyclohexane. In certain embodiments, the process comprises a mixture of THF and cyclohexane. In certain embodiments, the process comprises a mixture of chloroform and cyclohexane. In certain embodiments, the process comprises a mixture of heptane and chloroform.

In certain embodiments, the v:v ratio of solvent:solvent is about 20:1. In certain embodiments, the v:v ratio of solvent:solvent is about 10:1. In certain embodiments, the v:v ratio of solvent:solvent is about 5:1. In certain embodiments, the v:v ratio of solvent:solvent is about 2:1. In certain embodiments, the v:v ratio of solvent:solvent is about 1:20. In certain embodiments, the v:v ratio of solvent:solvent is about 1:10. In certain embodiments, the v:v ratio of solvent:solvent is about 1:5. In certain embodiments, the v:v ratio of solvent:solvent is about 1:2. In certain embodiments, the v:v ratio of solvent:solvent is 1:1.

In certain embodiments, Compound 1 is dissolved at a temperature ranging from about rt to about 100° C. In certain embodiments, Compound 1 is dissolved at a temperature ranging from about rt to about 75° C. In certain embodiments, Compound 1 is dissolved at a temperature ranging from about 25° C. to about 75° C. In certain embodiments, Compound 1 is dissolved at a temperature of about 50° C.

In certain embodiments, the process comprises a first solvent, then a second solvent. In certain embodiments, the second solvent is n-heptane.

In another aspect, the invention features a process of preparing Form NF5 comprising dissolving Compound 1 in dichloromethane, chloroform, hexane, cyclohexane, heptane, THF, o-xylene, dioxane, DMSO, water, or a mixture thereof.

In certain embodiments, the process comprises a mixture of THF and o-xylene.

In certain embodiments, the v:v ratio of solvent:solvent is about 20:1. In certain embodiments, the v:v ratio of solvent:solvent is about 10:1. In certain embodiments, the v:v ratio of solvent:solvent is about 5:1. In certain embodiments, the v:v ratio of solvent:solvent is about 2:1. In certain embodiments, the v:v ratio of solvent:solvent is about 1:20. In certain embodiments, the v:v ratio of solvent:solvent is about 1:10. In certain embodiments, the v:v ratio of solvent:solvent is about 1:5. In certain embodiments, the v:v ratio of solvent:solvent is about 1:2. In certain embodiments, the v:v ratio of solvent:solvent is 1:1.

In certain embodiments, Compound 1 is dissolved at a temperature ranging from about rt to about 100° C. In certain embodiments, Compound 1 is dissolved at a temperature ranging from about rt to about 75° C. In certain embodiments, Compound 1 is dissolved at a temperature ranging from about 25° C. to about 75° C. In certain embodiments, Compound 1 is dissolved at a temperature of about 50° C.

In certain embodiments, the process comprises a first solvent, then a second solvent. In certain embodiments, the first solvent is dioxane and the second solvent is n-heptane. In certain embodiments, the first solvent is dichloromethane and the second solvent is cyclohexane. In certain embodiments, the first solvent is chloroform and the second solvent is cyclohexane. In certain embodiments, the first solvent is THF and the second solvent is n-hexane. In certain embodiments, the first solvent is THF and the second solvent is cyclohexane. In certain embodiments, the first solvent is DMSO and the second solvent is water.

In another aspect, the invention features a process of preparing Form NF6 comprising dissolving Compound 1 in dichloromethane. In certain embodiments, the process comprises a second solvent. In certain embodiments, the second solvent is n-heptane.

In certain embodiments, the compounds and solid forms of the invention were synthesized in accordance with the schemes provided in the Examples below.

4. Uses. Formulation and Administration

Pharmaceutically Acceptable Compositions

According to another embodiment, the invention provides a composition comprising a solid form of compound 1 of this invention or a pharmaceutically acceptable derivative thereof and a pharmaceutically acceptable carrier, adjuvant, or vehicle. The amount of solid form of compound 1 in compositions of this invention is such that is effective to measurably inhibit BTK, or a mutant thereof, in a biological sample or in a patient. In certain embodiments, the amount of solid form of compound 1 in compositions of this invention is such that is effective to measurably inhibit BTK, or a mutant thereof, in a biological sample or in a patient. In certain embodiments, a composition of this invention is formulated for administration to a patient in need of such composition.

The term "patient" or "subject", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the solid form of the compound with which it is formulated. Pharmaceutically acceptable carriers, adjuvants or vehicles that are used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Compositions of the present invention are administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention include aqueous or oleaginous suspension. These suspensions are formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that are employed are water, Ringer's solution and isotonic sodium chloride solution. In addition, sterile, fixed oils are conventionally employed as a solvent or suspending medium.

For this purpose, any bland fixed oil employed includes synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms are also be used for the purposes of formulation.

Pharmaceutically acceptable compositions of this invention are orally administered in any orally acceptable dosage form. Exemplary oral dosage forms are capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents are optionally also added.

Alternatively, pharmaceutically acceptable compositions of this invention are administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention are also administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches are also used.

For topical applications, provided pharmaceutically acceptable compositions are formulated in a suitable ointment containing the active component suspended or dissolved in one or more carriers. Exemplary carriers for topical administration of compounds of this are mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol benzyl alcohol and water.

Pharmaceutically acceptable compositions of this invention are optionally administered by nasal aerosol or inhalation. Such compositions are prepared according to techniques well-known in the art of pharmaceutical formulation and are prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that are optionally combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

In certain embodiments, the invention provides a method for inhibiting BTK, or a mutant thereof, in a patient or in a biological sample comprising the step of administering to said patient or contacting said biological sample with a solid form of compound 1, or pharmaceutically acceptable salts thereof, according to the invention.

In certain embodiments, the invention is directed to the use of a solid form of compound 1, or pharmaceutically acceptable salts thereof, for modulating or inhibiting a BTK enzyme. The term "modulation" denotes any change in BTK-mediated signal transduction, which is based on the action of the specific inventive compounds capable to interact with the BTK target in such a manner that makes recognition, binding and activating possible. The compounds are characterized by such a high affinity to BTK, which ensures a reliable binding of BTK. In certain embodiments, the substances are highly selective for BTK over most other kinases in order to guarantee an exclusive and directed recognition with the single BTK target. In the context of the present invention, the term "recognition"—without being limited thereto—relates to any type of interaction between the specific compounds and the target, particularly covalent or non-covalent binding or association, such as a covalent bond, hydrophobic/hydrophilic interactions, van der Waals forces, ion pairs, hydrogen bonds, ligand-receptor (enzyme-inhibitor) interactions, and the like. Such association may also encompass the presence of other molecules such as peptides, proteins or nucleotide sequences. The present protein/ligand(enzyme-inhibitor)-interaction is characterized by high affinity, high selectivity and minimal or even lacking cross-reactivity to other target molecules to exclude unhealthy and harmful impacts to the treated subject.

In certain embodiments, the present invention relates to a method for inhibiting a BTK enzyme, with at least a solid form of compound 1, or pharmaceutically acceptable salts thereof, under conditions such that said BTK enzyme is inhibited. In certain embodiments, the system is a cellular system. In other embodiments, the system is an in-vitro translation which is based on the protein synthesis without living cells. The cellular system is defined to be any subject provided that the subject comprises cells. Hence, the cellular system can be selected from the group of single cells, cell cultures, tissues, organs and animals. In certain embodiments, the method for modulating a BTK enzyme is performed in-vitro. The prior teaching of the present specification concerning a solid form of compound 1, or pharmaceutically acceptable salts thereof, including any embodiments thereof, is valid and applicable without restrictions to the compounds when used in the method for inhibiting BTK. The prior teaching of the present specification concerning a solid form of compound 1, or pharmaceutically acceptable salts thereof, is valid and applicable without restrictions to the compounds when used in the method for inhibiting BTK.

Patients with mutations in BTK have a profound block in B cell development, resulting in the almost complete absence of mature B lymphocytes and plasma cells, severely reduced Ig levels and a profound inhibition of humoral response to recall antigens (reviewed in Vihinen et al Frontiers in Bioscience 5: d917-928). Mice deficient in BTK also have a reduced number of peripheral B cells and greatly decreased serum levels of IgM and IgG3. BTK deletion in mice has a profound effect on B cell proliferation induced by anti-IgM, and inhibits immune responses to thymus-independent type II antigens (Ellmeier et al. J Exp Med 192: 1611-1623 (2000)). BTK also plays a crucial role in mast cell activation through the high-affinity IgE receptor (Fc epsilon RI). BTK deficient murine mast cells have reduced degranulation and decreased production of proinflammatory cytokines following Fc epsilon RI cross-linking (Kawakami et al. Journal of Leukocyte Biology 65: 286-290).

Provided solid forms of compound 1, or pharmaceutically acceptable salts thereof, are inhibitors of BTK and are therefore useful for treating one or more disorders associated with activity of BTK. Thus, in some embodiments, the present invention provides a method for treating a BTK-mediated disorder comprising the step of administering to a patient in need thereof a solid form of compound 1, or pharmaceutically acceptable salts thereof.

As used herein, the term "BTK-mediated" disorders or conditions as used herein means any disease or other deleterious condition in which BTK, or a mutant thereof, is known to play a role. Accordingly, another embodiment of the present invention relates to treating or lessening the severity of one or more diseases in which BTK, or a mutant thereof, is known to play a role. Specifically, the present invention relates to a method of treating or lessening the severity of a disease or condition selected from a proliferative disorder or an autoimmune disorder, wherein said method comprises administering to a patient in need thereof a compound or composition according to the present invention.

In some embodiments, the present invention provides a method for treating or lessening the severity of one or more diseases and conditions associated with BTK. In some embodiments, the disease or condition is an autoimmune disease, e.g., inflammatory bowel disease, arthritis, systemic lupus erythematosus (SLE or lupus), lupus nephritis, vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis. Sjogren's syndrome, multiple sclerosis, systemic sclerosis, Lyme neuroborreliosis. Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome. Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, or vulvodynia. In certain embodiments, the disease or condition is systemic lupus erythematosus (SLE or lupus) or lupus nephritis.

In some embodiments, the disease or condition is a hyperproliferative disease or immunologically-mediated diseases including rejection of transplanted organs or tissues and Acquired Immunodeficiency Syndrome (AIDS, also known as HIV).

In some embodiments, the present invention provides a method for treating or lessening the severity of one or more diseases and conditions associated with BTK, wherein the disease or condition is selected from heteroimmune conditions or diseases, which include, but are not limited to graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

In some embodiments, the present invention provides a method for treating or lessening the severity of one or more diseases and conditions associated with BTK, wherein the disease or condition is selected from an inflammatory disease, e.g., asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis.

In some embodiments, the present invention provides a method for treating or lessening the severity of one or more diseases and conditions associated with BTK, wherein the disease or condition is selected from a cancer. In one embodiment, the cancer is a B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma. Burkitt lymphoma/leukemia, or lymphomatoid granulomatosis. In some embodiments, the cancer is breast cancer, prostate cancer, or cancer of the mast cells (e.g., mastocytoma, mast cell leukemia, mast cell sarcoma, systemic mastocytosis). In one embodiment, the cancer is bone cancer. In another embodiment, the cancer is of other primary origin and metastasizes to the bone. In certain embodiments, the cancer is colorectal cancer or pancreatic cancer.

In some embodiments, the present invention provides a method for treating or lessening the severity of one or more diseases or conditions associated with BTK including diseases of the bone and joints including, without limitation, rheumatoid arthritis, seronegative spondyloarthropathies (including ankylosing spondylitis, psoriatic arthritis and Reiter's disease). Behcet's disease, Sjogren's syndrome, systemic sclerosis, osteoporosis, bone cancer, and bone metastasis.

In some embodiments, the present invention provides a method for treating or lessening the severity of one or more diseases and conditions associated with BTK, wherein the disease or condition is selected from a thromboembolic disorder or cardiovascular disorder, e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, or deep venous thrombosis. In certain embodiments, the present invention provides an anti-thrombotic agent because Btk is also involved in the activation of platelets.

In some embodiments, the present invention provides a method for treating or lessening the severity of one or more diseases and conditions associated with BTK, including infectious and noninfectious inflammatory events and autoimmune and other inflammatory diseases. These autoimmune and inflammatory diseases, disorders, and syndromes include inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy. Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states. Goodpasture's syndrome, atherosclerosis, Addison's disease, Parkinson's disease, Alzheimer's disease, diabetes, septic shock, systemic lupus erythematosus (SLE), rheumatoid arthritis, psoriatic arthritis, juvenile arthritis, osteoarthritis, chronic idiopathic thrombocytopenic purpura. Waldenstrom macroglobulinemia, myasthenia gravis. Hashimoto's thyroiditis, atopic dermatitis, degenerative joint disease, vitiligo, autoimmune hypopituitarism, Guillain-Barre syndrome, Behcet's disease, scleraderma, mycosis fungoides, acute inflammatory responses (such as acute respiratory distress syndrome and ischemia/reperfusion injury), and Graves' disease. In certain embodiments, the diabetes is type I diabetes.

In some embodiments, the present invention provides a method for treating or lessening the severity of one or more diseases and conditions associated with BTK, selected from rheumatoid arthritis, multiple sclerosis, B-cell chronic lymphocytic leukemia, acute lymphocytic leukemia, hairy cell leukemia, non-Hodgkin's lymphoma. Hodgkin's lymphoma, multiple myeloma, bone cancer, bone metastasis, osteoporosis, diabetes (e.g. type I diabetes), irritable bowel syndrome. Crohn's disease, lupus and renal transplant.

In certain embodiments, the invention provides a method for the treatment and/or prophylaxis of multiple sclerosis (MS), including relapsing MS (RMS), relapsing-remitting MS (RRMS), progressive MS (PMS), secondary-progressive MS (SPMS), primary-progressive MS (PPMS), and progressive-relapsing MS (PRMS), comprising administering to a subject a solid form of compound 1.

It is another object of the invention to provide a method for treating diseases that are caused, mediated and/or propagated by BTK activity, wherein a solid form of compound 1, or pharmaceutically acceptable salts thereof is administered to a mammal in need of such treatment. In certain embodiments, the invention provides a method for treating lupus, wherein a solid form of compound 1, or pharmaceutically acceptable salts thereof is administered to a mammal in need of such treatment. In certain embodiments, the compound is administered in an effective amount as defined above. In certain embodiments, the treatment is an oral administration.

The method of the invention can be performed either in-vitro or in-vivo. The susceptibility of a particular cell to treatment with the compounds according to the invention can be particularly determined by in-vitro tests, whether in the course of research or clinical application. Typically, a culture of the cell is combined with a compound according to the invention at various concentrations for a period of time which is sufficient to allow the active agents to inhibit BTK activity, usually between about one hour and one week. In-vitro treatment can be carried out using cultivated cells from a biopsy sample or cell line.

The host or patient can belong to any mammalian species, for example a primate species, particularly humans: rodents, including mice, rats and hamsters; rabbits; horses, cows, dogs, cats, etc. Animal models are of interest for experimental investigations, providing a model for treatment of human disease.

For identification of a signal transduction pathway and for detection of interactions between various signal transduction pathways, various scientists have developed suitable models or model systems, for example cell culture models and models of transgenic animals. For the determination of certain stages in the signal transduction cascade, interacting compounds can be utilized in order to modulate the signal. The compounds according to the invention can also be used as reagents for testing BTK-dependent signal transduction pathways in animals and/or cell culture models or in the clinical diseases mentioned in this application.

Moreover, the subsequent teaching of the present specification concerning the use of a solid form of compound 1, or pharmaceutically acceptable salts thereof for the production of a medicament for the prophylactic or therapeutic treatment and/or monitoring is considered as valid and applicable without restrictions to the use of the compound for the inhibition of BTK activity if expedient.

The invention also relates to the use of a solid form of compound 1, or pharmaceutically acceptable salts thereof for the prophylactic or therapeutic treatment and/or monitoring of diseases that are caused, mediated and/or propagated by BTK activity. Furthermore, the invention relates to the use of a solid form of compound 1, or pharmaceutically acceptable salts thereof for the production of a medicament for the prophylactic or therapeutic treatment and/or monitoring of diseases that are caused, mediated and/or propagated by BTK activity. In certain embodiments, the invention provides the use of a solid form of compound 1, or pharmaceutically acceptable salts thereof, for the production of a medicament for the prophylactic or therapeutic treatment of a BTK-mediated disorder.

Another object of the present invention is a solid form of compound 1, or pharmaceutically acceptable salts thereof thereof for use in the prophylactic or therapeutic treatment and/or monitoring of diseases that are caused, mediated and/or propagated by BTK activity. Another preferred object of the invention concerns a solid form of compound 1, or pharmaceutically acceptable salts thereof for use in the prophylactic or therapeutic treatment and/or monitoring of lupus.

The solid form of compound 1, or pharmaceutically acceptable salts thereof can be administered before or following an onset of disease once or several times acting as therapy. The aforementioned compounds and medical products of the inventive use are particularly used for the therapeutic treatment. A therapeutically relevant effect relieves to some extent one or more symptoms of a disorder, or returns to normality, either partially or completely, one or more physiological or biochemical parameters associated with or causative of a disease or pathological condition. Monitoring is considered as a kind of treatment provided that the compounds are administered in distinct intervals, e.g. in order to boost the response and eradicate the pathogens and/or symptoms of the disease completely. Either the identical compound or different compounds can be applied. The methods of the invention can also be used to reduce the likelihood of developing a disorder or even prevent the initiation of disorders associated with BTK activity in advance or to treat the arising and continuing symptoms.

In the meaning of the invention, prophylactic treatment is advisable if the subject possesses any preconditions for the aforementioned physiological or pathological conditions, such as a familial disposition, a genetic defect, or a previously incurred disease.

The invention furthermore relates to a medicament comprising at least one solid form of compound 1, or pharmaceutically acceptable salts thereof.

A "medicament" in the meaning of the invention is any agent in the field of medicine, which comprises one or more compounds of formula (I) or preparations thereof (e.g. a pharmaceutical composition or pharmaceutical formulation) and can be used in prophylaxis, therapy, follow-up or aftercare of patients who suffer from diseases, which are associated with BTK activity, in such a way that a pathogenic modification of their overall condition or of the condition of particular regions of the organism could establish at least temporarily.

In various embodiments, the active ingredient may be administered alone or in combination with other treatments. A synergistic effect may be achieved by using more than one compound in the pharmaceutical composition, i.e. the compound of formula (I) is combined with at least another agent as active ingredient, which is either another compound of formula (I) or a compound of different structural scaffold. The active ingredients can be used either simultaneously or sequentially.

Included herein are methods of treatment in which at least one chemical entity provided herein is administered in combination with an anti-inflammatory agent. Anti-inflammatory agents include but are not limited to NSAIDs, non-specific and COX-2 specific cyclooxygenase enzyme inhibitors, gold compounds, corticosteroids, methotrexate, tumor necrosis factor (TNF) antagonists, immunosuppressants and methotrexate.

Examples of NSAIDs include, but are not limited to, ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors such as celecoxib, valdecoxib, lumiracoxib dnd/or etoricoxib.

In some embodiments, the anti-inflammatory agent is a salicylate. Salicylates include by are not limited to acetylsalicylic acid or aspirin, sodium salicylate, and choline and magnesium salicylates.

The anti-inflammatory agent may also be a corticosteroid. For example, the corticosteroid may be cortisone, dexamethasone, methylprednisolone, prednisolone, prednisolone sodium phosphate, or prednisone.

In additional embodiments the anti-inflammatory agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide.

Other embodiments of the invention pertain to combinations in which at least one anti-inflammatory compound is an anti-monoclonal antibody (such as eculizumab or pexelizumab), a TNF antagonist, such as entanercept, or infliximab, which is an anti-TNF alpha monoclonal antibody.

Still other embodiments of the invention pertain to combinations in which at least one active agent is an immunosuppressant compound such as an immunosuppressant compound chosen from methotrexate, leflunomide, cyclosporine, tacrolimus, azathioprine, and mycophenolate mofetil.

B-cells and B-cell precursors expressing BTK have been implicated in the pathology of B-cell malignancies, including, but not limited to, B-cell lymphoma, lymphoma (including Hodgkin's and non-Hodgkin's lymphoma), hairy cell lymphoma, multiple myeloma, chronic and acute myelogenous leukemia and chronic and acute lymphocytic leukemia.

BTK has been shown to be an inhibitor of the Fas/APO-1 (CD-95) death inducing signaling complex (DISC) in B-lineage lymphoid cells. The fate of leukemia/lymphoma cells may reside in the balance between the opposing proapoptotic effects of caspases activated by DISC and an upstream anti-apoptotic regulatory mechanism involving BTK and/or its substrates (Vassilev et al., J. Biol. Chem. 1998, 274, 1646-1656).

It has also been discovered that BTK inhibitors are useful as chemosensitizing agents, and, thus, are useful in combination with other chemotherapeutic drugs, in particular, drugs that induce apoptosis. Examples of other chemotherapeutic drugs that can be used in combination with chemosensitizing BTK inhibitors include topoisomerase I inhibitors (camptothecin or topotecan), topoisomerase II inhibitors (e.g. daunomycin and etoposide), alkylating agents (e.g. cyclophosphamide, melphalan and BCNU), tubulin directed agents (e.g. taxol and vinblastine), and biological agents (e.g. antibodies such as anti CD20 antibody, IDEC 8, immunotoxins, and cytokines).

The disclosed compounds of the formula I can be administered in combination with other known therapeutic agents, including anticancer agents. As used here, the term "anti-cancer agent" relates to any agent which is administered to a patient with cancer for the purposes of treating the cancer.

The anti-cancer treatment defined above may be applied as a monotherapy or may involve, in addition to the herein disclosed compounds of formula I, conventional surgery or radiotherapy or medicinal therapy. Such medicinal therapy, e.g. a chemotherapy or a targeted therapy, may include one or more, but preferably one, of the following anti-tumor agents;

Alkylating agents: such as altretamine, bendamustine, busulfan, carmustine, chlorambucil, chlormethine, cyclophosphamide, dacarbazine, ifosfamide, improsulfan, tosilate, lomustine, melphalan, mitobronitol, mitolactol, nimustine, ranimustine, temozolomide, thiotepa, treosulfan, mechloretamine, carboquone; apaziquone, fotemustine, glufosfamide, palifosfamide, pipobroman, trofosfamide, uramustine, TH-302[4], VAL-083[4];

Platinum Compounds: such as carboplatin, cisplatin, eptaplatin, miriplatine hydrate, oxaliplatin, lobaplatin, nedaplatin, picoplatin, satraplatin; lobaplatin, nedaplatin, picoplatin, satraplatin; DNA altering agents: such as amrubicin, bisantrene, decitabine, mitoxantrone, procarbazine, trabectedin, clofarabine; amsacrine, brostallicin, pixantrone, laromustine[1,3];

Topoisomerase Inhibitors: such as etoposide, irinotecan, razoxane, sobuzoxane, teniposide, topotecan; amonafide, belotecan, elliptinium acetate, voreloxin;

Microtubule modifiers: such as cabazitaxel, docetaxel, eribulin, ixabepilone, paclitaxel, vinblastine, vincristine, vinorelbine, vindesine, vinflunine; fosbretabulin, tesetaxel;

Antimetabolites: such as asparaginase[3], azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur; doxifluridine, elacytarabine, raltitrexed, sapacitabine, tegafur[2,3], trimetrexate;

Anticancer antibiotics: such as bleomycin, dactinomycin, doxorubicin, epirubicin, idarubicin, levamisole, miltefosine, mitomycin C, romidepsin, streptozocin, valrubicin, zinostatin, zorubicin, daunurobicin, plicamycin; aclarubicin, peplomycin, pirarubicin;

Hormones/Antagonists: such as abarelix, abiraterone, bicalutamide, buserelin, calusterone, chlorotrianisene, degarelix, dexamethasone, estradiol, fluocortolone fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol; acolbifene, danazol, deslorelin, epitiostanol, orteronel, enzalutamide[1,3];

Aromatase inhibitors: such as aminoglutethimide, anastrozole, exemestane, fadrozole, letrozole, testolactone; formestane:

Small molecule kinase inhibitors: such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib; afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, rigosertib, tipifamib, tivantinib, tivozanib, trametinib, pimasertib, brivanib alaninate, cediranib, apatinib[4], cabozantinib S-malate[1,3], ibrutinib[1,3], icotinib[4], buparlisib[2], cipatinib[4], cobimetinib[1,3], idelalisib[1,3], fedratinib[1], XL-647[4]; Photosensitizers: such as methoxsalen[3]; porfimer sodium, talaporfin, temoporfin; Antibodies: such as alemtuzumab, besilesomab, brentuximab vedotin, cetuximab, denosumab, ipilimumab, ofatumumab, panitumumab, rituximab, tositumomab, trastuzumab, bevacizumab, pertuzumab[2,3]; catumaxomab, elotuzumab, epratuzumab, farletuzumab, mogamulizumab, necitumumab, nimotuzumab, obinutuzumab, ocaratuzumab, oregovomab, ramucirumab, rilotumumab, siltuximab, tocilizumab, zalutumumab, zanolimumab, matuzumab, dalotuzumab[1,2,3], onartuzumab[1,3], racotumomab[1], tabalumab[1,3], EMD-525797[4], nivolumab[1,3];

Cytokines: such as aldesleukin, interferon alfa[2], interferon alfa2a[3], interferon alfa2b[2,3]; celmoleukin, tasonermin, teceleukin, oprelvekin[1,3], recombinant interferon beta-1a[4]:

Drug Conjugates: such as denileukin diftitox, ibritumomab tiuxetan, iobenguane I123, prednimustine, trastuzumab emtansine, estramustine, gemtuzumab, ozogamicin, aflibercept; cintredekin besudotox, edotreotide, inotuzumab ozogamicin, naptumomab estafenatox, oportuzumab monatox, technetium (99mTc) arcitumomab[1,3], vintafolide[1,3];

Vaccines: such as sipuleucel[3]; vitespen[3], emepepimut-S[3], oncoVAX[4], rindopepimut[3], troVax[4], MGN-1601[4], MGN-1703[4]; and Miscellaneous: alitretinoin, bexarotene, bortezomib, everolimus, ibandronic acid, imiquimod, lenalidomide, lentinan, metirosine, mifamurtide, pamidronic acid, pegaspargase, pentostatin, sipuleucel[3], sizofiran, tamibarotene, temsirolimus, thalidomide, tretinoin, vismodegib, zoledronic acid, vorinostat; celecoxib, cilengitide, entinostat, etanidazole, ganetespib, idronoxil, iniparib, ixazomib, lonidamine, nimorazole, panobinostat, peretinoin, plitidepsin, pomalidomide, procodazol, ridaforolimus, tasquinimod, telotristat, thymalfasin, tirapazamine, tosedostat, trabedersen, ubenimex, valspodar, gendicine[4], picibanil[4], reolysin[4], retaspimycin hydrochloride[1,3], trebananib[2,3], virulizin[4], carfilzomib[1,3], endostatin[4], immucothel[4], belinostat[3], MGN-1703[4].

([1]Prop. INN (Proposed International Nonproprietary Name): [2] Rec. INN (Recommended International Nonproprietary Names); [3] USAN (United States Adopted Name); [4] no INN).

In another aspect, the invention provides for a kit consisting of separate packs of an effective amount of a compound according to the invention and/or pharmaceutically acceptable salts, derivatives, solvates and stereoisomers thereof, including mixtures thereof in all ratios, and optionally, an effective amount of a further active ingredient. The kit comprises suitable containers, such as boxes, individual bottles, bags or ampoules. The kit may, for example, comprise separate ampoules, each containing an effective amount of a compound according to the invention and/or pharmaceutically acceptable salts, derivatives, solvates and stereoisomers thereof, including mixtures thereof in all ratios, and an effective amount of a further active ingredient in dissolved or lyophilized form.

As used herein, the terms "treatment," "treat," and "treating" refer to reversing, alleviating, delaying the onset of, or inhibiting the progress of a disease or disorder, or one or more symptoms thereof, as described herein. In some embodiments, treatment is administered after one or more symptoms have developed. In other embodiments, treatment is administered in the absence of symptoms. For example, treatment is administered to a susceptible individual prior to the onset of symptoms (e.g., in light of a history of symptoms and/or in light of genetic or other susceptibility factors). Treatment is also continued after symptoms have resolved, for example to prevent or delay their recurrence.

The compounds and compositions, according to the method of the present invention, are administered using any amount and any route of administration effective for treating or lessening the severity of a disorder provided above. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention are administered orally or parenterally at dosage levels of about 0.01 mg/kg to about 100 mg/kg and preferably from about 1 mg/kg to about 50 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms optionally contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions are formulated according to the known art using suitable dispersing or wetting agents and suspending agents. The sterile injectable preparation are also a sterile injectable solution, suspension or emulsion in a nontoxic parenterally acceptable diluent or solvent, for example, as a solution in 1,3-butanediol. Among the acceptable vehicles and solvents that may be employed are water, Ringer's solution. U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This is accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form also optionally comprises buffering agents.

Solid compositions of a similar type are also employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type are also employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms also comprise, as is normal practice, additional substances other than inert diluents, e.g., tableting lubricants and other tableting aids such a magnesium stearate and microcrystalline cellulose. In the case of capsules, tablets and pills, the dosage forms optionally also comprise buffering agents. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting BTK activity in a biological sample comprising the step of contacting said biological sample with a compound of this invention, or a composition comprising said compound.

According to another embodiment, the invention relates to a method of inhibiting BTK, or a mutant thereof, activity in a biological sample in a positive manner, comprising the step of contacting said biological sample with a compound of this invention, or a composition comprising said compound.

The compounds of the invention are useful in-vitro as unique tools for understanding the biological role of BTK, including the evaluation of the many factors thought to influence, and be influenced by, the production of BTK and the interaction of BTK. The present compounds are also useful in the development of other compounds that interact with BTK since the present compounds provide important structure-activity relationship (SAR) information that facilitate that development. Compounds of the present invention that bind to BTK can be used as reagents for detecting BTK in living cells, fixed cells, in biological fluids, in tissue homogenates, in purified, natural biological materials, etc. For example, by labeling such compounds, one can identify cells expressing BTK. In addition, based on their ability to bind BTK, compounds of the present invention can be used in in-situ staining, FACS (fluorescence-activated cell sorting), sodium dodecyl sulfate polyacrylamide gel electrophoresis (SDS-PAGE), ELISA (enzyme-linked immunoadsorptive assay), etc., enzyme purification, or in purifying cells expressing BTK inside permeabilized cells. The compounds of the invention can also be utilized as commercial research reagents for various medical research and diagnostic uses. Such uses can include but are not limited to: use as a calibration standard for quantifying the activities of candidate BTK inhibitors in a variety of functional assays; use as blocking reagents in random compound screening, i.e. in looking for new families of BTK ligands, the compounds can be used to block recovery of the presently claimed BTK compounds; use in the co-crystallization with BTK enzyme, i.e. the compounds of the present invention will allow formation of crystals of the compound bound to BTK, enabling the determination of enzyme/compound structure by x-ray crystallography; other research and diagnostic applications, wherein BTK is preferably activated or such activation is conveniently calibrated against a known quantity of an BTKinhibitor, etc.; use in assays as probes for determining the expression of BTK in cells; and developing assays for detecting compounds which bind to the same site as the BTK binding ligands.

The compounds of the invention can be applied either themselves and/or in combination with physical measurements for diagnostics of treatment effectiveness. Pharmaceutical compositions containing said compounds and the use of said compounds to treat BTK-mediated conditions is a promising, novel approach for a broad spectrum of therapies causing a direct and immediate improvement in the state of health, whether in human or animal. The orally bioavailable and active new chemical entities of the invention improve convenience for patients and compliance for physicians.

The compounds of formula (I), their salts, isomers, tautomers, enantiomeric forms, diastereomers, racemates, derivatives, prodrugs and/or metabolites are characterized by a high specificity and stability, low manufacturing costs and convenient handling. These features form the basis for a reproducible action, wherein the lack of cross-reactivity is included, and for a reliable and safe interaction with the target structure.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of BTK, or a mutant thereof, activity in a biological sample is useful for a variety of purposes that are known to one of skill in the art. Examples of such purposes include, but are not limited to, blood transfusion, organ transplantation, biological specimen storage, and biological assays.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

The symbols and conventions used in the following descriptions of processes, schemes, and examples are consistent with those used in the contemporary scientific literature, for example, the Journal of the American Chemical Society or the Journal of Biological Chemistry.

All forms were characterized according to standard methods which are found in e.g. Rolf Hilfiker, 'Polymorphism in the Pharmaceutical Industry'. Wiley-VCH. Weinheim 2006 (Chapter 6: X-Ray Diffraction. Chapter 6: Vibrational Spectroscopy. Chapter 3: Thermal Analysis, Chapter 9: Water Vapour Sorption, and references therein); and H. G. Brittain, 'Polymorphism in Pharmaceutical Solids. Vol. 95. Marcel Dekker Inc., New York 1999 (Chapter 6 and references therein).

Unless otherwise indicated, all temperatures are expressed in ° C. (degrees Centigrade). All reactions were conducted at room temperature unless otherwise noted. All compounds of the present invention were synthesized by processes developed by the inventors.

$^1$H-NMR spectra were recorded on a Bruker Avance III 400 MHz. Chemical shifts are expressed in parts per million (ppm, δ units). Coupling constants are in units of Hertz (Hz). Splitting patterns describe apparent multiplicities and are designated as s (singlet), d (doublet), t (triplet), q (quartet), m (multiplet), or br (broad).

Mass spectra were obtained on Agilent 1200 Series mass spectrometers from Agilent technologies, using either Atmospheric Chemical Ionization (APCI) or Electrospray Ionization (ESI). Column: XBridge C8, 3.5 μm, 4.6×50 mm; Solvent A: water+0.1% TFA; Solvent B: CAN; Flow: 2 ml/min; Gradient: 0 min: 5% B, 8 min: 100% B, 8.1 min: 100% B, 8.5 min: 5% B, 10 min 5% B.

HPLC data were obtained using Agilent 1100 series HPLC from Agilent technologies using XBridge column (C8, 3.5 μm, 4.6×50 mm). Solvent A: water+0.1% TFA; Solvent B: ACN; Flow: 2 ml/min; Gradient: 0 min: 5% B, 8 min: 100% B, 8.1 min: 100% B, 8.5 min: 5% B, 10 min 5% B.

The microwave reactions were conducted using Biotage Initiator Microwave Synthesizer using standard protocols that are known in the art.

Some abbreviations that may appear in this application are as follows:

| | |
|---|---|
| δ | chemical shift |
| d | deuterium or doublet |
| dd | doublet of doublets |
| DCM | dichloromethane |
| DMF | dimethylformamide |
| DMSO | dimethylsulfoxide |
| THF | tetrhydrofuran |
| eq. | equivalent |
| h | hour |
| $^1$H | proton |
| HPLC | high pressure liquid chromatography |
| J | coupling constant |
| LC | liquid chromatography |
| m | multiplet |
| M | molecular ion |
| MHz | Megahertz |
| min | minute |
| mL | milliliter |
| MS | mass spectrometry |
| m/z | mass-to-charge ratio |
| NMR | nuclear magnetic resonance |
| RBF | Round Bottom Flask |
| RT | room temperature |
| s | singlet |
| TLC | thin layer chromatography |
| UV | ultraviolet |

Compound numbers utilized in the Examples below correspond to compound numbers set forth supra.

Example 1: Lyophilisation from MeOH/EtOAc Mixtures (Following Variations as Described in WO2012/170976, Method F)

a) Lyophilisation from MeOH:EtOAc 10:90 (v:v) (14/BE/19247):

Approx. 30 mg purified free base was dissolved in 2 mL of a mixture MeOH:EtOAc 10:90 (v:v) at RT (approx. 22° C.) to give a clear solution. This solution was frozen in liquid nitrogen in a 50 mL round-bottom flask, and the frozen sample was attached to a lyophilisator (Steris, Lyovac GT2) operating at approx. 0.3 mbar. After 4 days, a white solid residue was collected.

$^1$H NMR (700 MHz, DMSO-d6): δ 7.95 (s, 1H), 7.47-7.37 (m, 2H), 7.22 (d, J=8.6 Hz, 2H), 7.17 (t, J=7.4 Hz, 1H), 7.14-7.09 (m, 4H), 6.78 (dd, J=16.7, 10.5 Hz, 1H), 6.06 (dd, J=16.7, 2.4 Hz, 1H), 5.63 (dd, J=10.5, 2.4 Hz, 1H), 5.51-5.35 (m, 3H), 4.36 (d, J=13.0 Hz, 1H), 4.00 (d, J=13.5 Hz, 1H), 3.14 (t, J=6.6 Hz, 2H), 2.97 (t, J=12.1 Hz, 1H), 2.58 (t, J=11.6 Hz, 1H), 1.88-1.79 (m, 1H), 1.61 (t, J=13.0 Hz, 2H), 1.00-0.88 (m, 2H).

PXRD:

| No. | °2θ (Cu—Kα$_1$ radiation) ± 0.2° |
|---|---|
| 1 | 4.7 |
| 2 | 9.5 |
| 3 | 11.7 |
| 4 | 12.0 |
| 5 | 13.2 |
| 6 | 14.2 |
| 7 | 15.0 |
| 8 | 16.8 |
| 9 | 17.4 |
| 10 | 18.1 |
| 11 | 20.0 |
| 12 | 20.4 |
| 13 | 23.6 |

M.p.: 170.4° C. (onset)

b) Lyophilisation from MeOH:EtOAc 50:50 (v:v) (14/BE/19248):

Approx. 30 mg purified free base was dissolved in 1 mL of a mixture MeOH:EtOAc 50:50 (v:v) at RT (approx. 22° C.) to give a clear solution. This solution was frozen in liquid nitrogen in a 50 mL round-bottom flask, and the frozen sample was attached to a lyophilisator (Steris, Lyovac GT2) operating at approx. 0.3 mbar. After 4 days, a white solid residue was obtained.

$^1$H NMR (700 MHz, DMSO-d6): δ 7.95 (s, 1H), 7.46-7.40 (m, 2H), 7.22 (d, J=8.6 Hz, 2H), 7.17 (t, J=7.4 Hz, 1H), 7.15-7.09 (m, 4H), 6.78 (dd, J=16.7, 10.5 Hz, 1H), 6.06 (dd, J=16.7, 2.4 Hz, 1H), 5.63 (dd, J=10.5, 2.4 Hz, 1H), 5.51-5.35 (m, 3H), 4.36 (d, J=12.5 Hz, 1H), 4.00 (d, J=13.4 Hz, 1H), 3.14 (t, J=6.6 Hz, 2H), 2.97 (t, J=12.2 Hz, 1H), 2.58 (t, J=12.1 Hz, 1H), 1.88-1.80 (m, 1H), 1.61 (t, J=12.8 Hz, 2H), 1.00-0.88 (m, 2H).

PXRD:

| No. | °2θ (Cu—Kα$_1$ radiation) ± 0.2° |
|---|---|
| 1 | 4.7 |
| 2 | 9.5 |
| 3 | 11.7 |
| 4 | 12.0 |
| 5 | 13.1 |
| 6 | 14.2 |
| 7 | 16.8 |
| 8 | 17.4 |
| 9 | 18.1 |
| 10 | 20.0 |
| 11 | 22.8 |
| 12 | 23.6 |

M.p.: 170.8° C. (onset)

c) Lyophilisation from MeOH:EtOAc 90:10 (v:v) (14/BE/19254):

Approx. 30 mg purified free base was dissolved in 1 mL of a mixture MeOH:EtOAc 90:10 (v:v) at RT (approx. 22° C.) to give a clear solution. This solution was frozen in liquid nitrogen in a 50 mL round-bottom flask, and the frozen sample was attached to a lyophilisator (Steris, Lyovac GT2) operating at approx. 0.3 mbar. After 4 days, a white solid residue was obtained.

$^1$H NMR (700 MHz, DMSO-d6): δ 7.95 (s, 1H), 7.45-7.40 (m, 2H), 7.22 (d, J=8.6 Hz, 2H), 7.17 (t, J=7.4 Hz, 1H), 7.15-7.05 (m, 4H), 6.78 (dd, J=16.7, 10.5 Hz, 1H), 6.06 (dd, J=16.7, 2.4 Hz, 1H), 5.63 (dd, J=10.5, 2.4 Hz, 1H), 5.49-5.38 (m, 3H), 4.36 (d, J=12.6 Hz, 1H), 4.00 (d, J=13.1 Hz, 1H), 3.14 (t, J=6.6 Hz, 2H), 2.97 (t, J=12.3 Hz, 1H), 2.58 (t, J=11.9 Hz, 1H), 1.88-1.79 (m, 1H), 1.61 (t, J=12.9 Hz, 2H), 1.00-0.89 (m, 2H).

PXRD:

| No. | °2θ (Cu—Kα$_1$ radiation) ± 0.2° |
|---|---|
| 1 | 4.7 |
| 2 | 9.5 |
| 3 | 11.9 |
| 4 | 13.1 |
| 5 | 14.2 |
| 6 | 15.1 |
| 7 | 17.4 |
| 8 | 18.1 |
| 9 | 20.0 |
| 10 | 20.3 |
| 11 | 21.5 |
| 12 | 23.6 |

M.p.: 171.7° C. (onset)

Example 2: Crystallisation Trials of Free Base Yielding Morphic Form Mixtures a) Crystallisation from n-Heptane:EtOH 7:3

Approx. 200 mg crude free base was dispersed in 2 mL Methanol, and diluted with 8 mL Ethanol to give a clear solution. The sample solution was injected on a preparative chromatography column (Chiralpak AD, 50×5 cm), using an isocratic mobile phase of n-Heptane:Ethanol (7:3, v:v) with 100 mL/min flow rate. Resulting fractions of purified free base were collected, and evaporated to dryness under vacuum at 50° C.

$^1$H NMR (500 MHz, DMSO-d6): δ 7.95 (s, 1H), 7.42 (dd, J=8.5, 7.5 Hz, 2H), 7.22 (d, J=8.6 Hz, 2H), 7.16 (t, J=7.4 Hz, 1H), 7.14-7.08 (m, 4H), 6.76 (dd, J=16.7, 10.5 Hz, 1H), 6.05 (dd, J=16.7, 2.4 Hz, 1H), 5.62 (dd, J=10.5, 2.4 Hz, 1H), 5.45-5.37 (m, 3H), 4.35 (d, J=12.3 Hz, 1H), 3.99 (d, J=13.1 Hz, 1H), 3.14 (t, J=6.5 Hz, 2H), 2.97 (t, J=12.3 Hz, 1H), 2.57 (t, J=12.0 Hz, 1H), 1.88-1.77 (m, 1H), 1.66-1.56 (m, 2H), 1.01-0.87 (m, 2H).

b) Crystallisation from Ethanol 3250 g crude free base was dissolved in 7.0 L ethanol at 70° C. Subsequently 200 g of seeding crystals were added and the mixture was slowly cooled down within 6 hours to 20° C. Thereafter the suspension was further cooled down to 0° C. within 16 hours. The suspension was the filtered and the residue was washed with 2.0 L ethanol. Subsequently the solid was dried at 80 mbar and 30° C. until mass consistency.

$^1$H NMR (500 MHz, DMSO-d6): δ 7.96 (s, 1H), 7.43 (dd, J=8.5, 7.5 Hz, 2H), 7.24 (d, J=8.7 Hz, 2H), 7.17 (t, J=7.4 Hz, 1H), 7.15-7.10 (m, 4H), 6.77 (dd, J=16.7, 10.5 Hz, 1H), 6.06 (dd, J=16.7, 2.5 Hz, 1H), 5.63 (dd, J=10.5, 2.4 Hz, 1H), 5.47-5.38 (m, 3H), 4.36 (d, J=12.3 Hz, 1H), 4.00 (d, J=13.0 Hz, 1H), 3.16 (t, J=6.5 Hz, 2H), 2.98 (t, J=12.4 Hz, 1H), 2.58 (t, J=11.9 Hz, 1H), 1.89-1.79 (m, 1H), 1.67-1.57 (m, 2H), 1.03-0.88 (m, 2H).

Example 3: Crystallisation Processes of Free Base to Obtain Pure Form A1 a) Crystallisation from THF

Approximately 10.4 g free base of compound 1 was dissolved in 300 mL THF at RT. Approximately 16.6 g of Si-DMT scavenger was dispersed, and the suspension was stirred overnight. Afterwards, the suspension was filtered, and resulting filter cake was washed with 2×100 ml THF. The clear filtrate was concentrated to dryness to afford a white solid which was dried under vacuum.

$^1$H NMR (500 MHz, DMSO-d6): δ 7.95 (s, 1H), 7.45-7.40 (m, 2H), 7.23 (d, J=8.7 Hz, 2H), 7.17 (t, J=7.4 Hz, 1H), 7.14-7.10 (m, 4H), 6.78 (dd, J=16.7, 10.5 Hz, 1H), 6.06 (dd, J=16.7, 2.5 Hz, 1H), 5.63 (dd, J=10.5, 2.5 Hz, 1H), 5.49-5.37 (m, 3H), 4.36 (d, J=12.7 Hz, 1H), 4.00 (d, J=13.4 Hz, 1H), 3.14 (t, J=6.5 Hz, 2H), 2.97 (t, J=12.6 Hz, 1H), 2.58 (t, J=11.7 Hz, 1H), 1.89-1.79 (m, 1H), 1.66-1.57 (m, 2H), 1.00-0.87 (m, 2H).

b) Water anti-solvent crystallisation from Isopropylacetate solution A suspension of 1 eq. of 5-(4-Phenoxyphenyl)-N-piperidin-4-ylmethyl-pyrimidine-4,6-diamine and 1 eq. $K_2CO_3$ in N,N-Dimethylacetamide (5 vol. eq.) was cooled down to −20° C. Acryloyl chloride (1 eq.) was then added drop-wise over 5 hrs. After reaction completion (by HPLC), an aqueous solution of 1N Acetic Acid/15 vol. eq.) was added to the reaction mixture keeping the internal temperature below 5° C. At the end of the addition, the solution was heated up to 20° C. and extracted with Isopropylacetate (4×15 vol eq.). The combined organics were concentrated to give a dark oil and after a treatment with 5% $NaHCO_3$ aqueous solution, a suspension was obtained. The precipitate was aged for 2 hrs and then filtered to afford the final product, which was dried under vacuum at 50° C. overnight.

$^1$H NMR (500 MHz, DMSO-d6) δ 7.94 (s, 1H), 7.42 (dd, J=8.6, 7.4 Hz, 2H), 7.22 (d, J=8.6 Hz, 2H), 7.16 (tt, J=7.4, 1.0 Hz, 1H), 7.13-7.09 (m, 4H), 6.76 (dd, J=16.7, 10.5 Hz, 1H), 6.05 (dd, J=16.7, 2.4 Hz, 1H), 5.62 (dd, J=10.5, 2.4 Hz, 1H), 5.44-5.35 (m, 3H), 4.35 (d, J=12.4 Hz, 1H), 3.99 (d, J=13.1 Hz, 1H), 3.14 (t, J=6.5 Hz, 2H), 2.97 (t, J=12.3 Hz, 1H), 2.57 (t, J=11.9 Hz, 1H), 1.88-1.78 (m, 1H), 1.65-1.55 (m, 2H), 1.01-0.87 (m, 2H).

Example 4: Crystallisation Processes of Free Base to Obtain Novel Form A2 a) Crystallisation from MeOH:Water (1:1, v:v)

Approximately 2400 mg crude free base of compound 1 were dissolved in 250 mL Methanol:Water mixture (1:1, v:v) at 50° C. The solution was filtrated, and the clear filtrate was evaporated to dryness at 50° C. at ambient pressure.

$^1$H NMR (400 MHz, DMSO-d6): δ 7.95 (s, 1H), 7.43 (dd, J=8.5, 7.5 Hz, 2H), 7.23 (d, J=8.7 Hz, 2H), 7.17 (t, J=7.4 Hz, 1H), 7.15-7.09 (m, 4H), 6.77 (dd, J=16.7, 10.5 Hz, 1H), 6.06 (dd, J=16.7, 2.5 Hz, 1H), 5.63 (dd, J=10.5, 2.5 Hz, 1H), 5.47-5.37 (m, 3H), 4.35 (d, J=12.3 Hz, 1H), 4.00 (d, J=12.9 Hz, 1H), 3.15 (t, J=6.5 Hz, 2H), 2.98 (t, J=12.3 Hz, 1H), 2.58 (t, J=11.6 Hz, 1H), 1.91-1.76 (m, 1H), 1.68-1.55 (m, 2H), 1.03-0.86 (m, 2H).

b) Water anti-solvent crystallisation from filtrated Ethanol solution 1. eq. of crude free base product (following example 3b) was dissolved in hot Ethanol (5 vol. eq.), transferred to a reactor via filtration (the API solution was clarified through 10 µm cartridge) and cooled down to 10° C. over 5 hrs. The product was isolated by filtration and dried under vacuum for 8 hrs at 50° C. The dried API was dissolved again in hot Ethanol (15 vol. eq.), cooled down to ambient and filtered first through paper and then through a 0.22 µm cartridge. The resulting clear solution was charged back to the reactor and water (30 vol. eq.) was added at 25° C. Precipitation occured, and the resulting suspension was cooled down to 10° C. and the solid was isolated by filtration to obtain the final product which was dried under vacuum at 50° C. overnight.

$^1$H NMR (500 MHz, DMSO-d6) δ 7.94 (s, 1H), 7.42 (dd, J=8.5, 7.5 Hz, 2H), 7.22 (d, J=8.6 Hz, 2H), 7.16 (t, J=7.4 Hz, 1H), 7.13-7.08 (m, 4H), 6.76 (dd, J=16.7, 10.5 Hz, 1H), 6.05 (dd, J=16.7, 2.4 Hz, 1H), 5.62 (dd, J=10.5, 2.4 Hz, 1H), 5.44-5.34 (m, 3H), 4.35 (d, J=12.4 Hz, 1H), 3.99 (d, J=13.1 Hz, 1H), 3.14 (t, J=6.5 Hz, 2H), 2.97 (t, J=12.4 Hz, 1H), 2.57 (t, J=11.9 Hz, 1H), 1.88-1.77 (m, 1H), 1.65-1.55 (m, 2H), 1.01-0.87 (m, 2H).

Example 5: Crystallisation Processes of Free Base to Obtain Novel Form NF4 a) Evaporation Crystallisation from Dichloromethane:Cyclohexane Mixture

Approximately 17 mg crude free base were dissolved in 2 mL Dichloromethane:Cyclohexane mixture (1:1, vol:vol), and evaporated at 50° C. to obtain a solid residue.

b) Evaporation Crystallisation from THF:Cyclohexane Mixture

Approximately 16 mg crude free base were dissolved in 2 mL THF:Cyclohexane mixture (1:1. vol:vol), and evaporated at 50° C. to obtain a solid residue.

c) Evaporation Crystallisation from Chloroform:Cyclohexane Mixture Approximately 17 mg crude free base were dissolved in 2 mL Chloroform:Cyclohexane mixture (1:1, vol:vol), and evaporated at 50° C. to obtain a solid residue.

d) n-Heptane Anti-Solvent Crystallisation from Chloroform Solution

Approximately 20 mg crude free base were dissolved in 0.5 mL Chloroform, and poured into 4 mL n-Heptane reservoir upon vigorous stirring. The resulting suspension was centrifuged, and separated solid-state residue dried under nitrogen flow to obtain a powder.

Example 6: Crystallisation Processes of Free Base to Obtain Novel Form NF5 a) Evaporation Crystallisation from THF:o-Xylene Mixture Approximately 20 mg crude free base were dissolved in 2 mL THF:o-Xylene mixture (1:1. vol:vol), and evaporated at 50° C. to obtain a solid residue.

b) n-Heptane Anti-Solvent Crystallisation from Dioxane Solution

Approximately 8 mg crude free base were dissolved in 0.5 mL Dioxane, and poured into 3.5 mL n-Heptane reservoir upon vigorous stirring. The resulting suspension was centrifuged, and separated solid-state residue dried under nitrogen flow to obtain a powder.

c) Cyclohexane Anti-Solvent Crystallisation from Dichloromethane Solution

Approximately 20 mg crude free base were dissolved in 0.5 mL Dichloromethane, and poured into 4 mL Cyclohexane reservoir upon vigorous stirring. The resulting suspension was centrifuged, and separated solid-state residue dried under nitrogen flow to obtain a powder.

d) Cyclohexane Anti-Solvent Crystallisation from Chloroform Solution

Approximately 20 mg crude free base were dissolved in 0.5 mL Chloroform, and poured into 4 mL Cyclohexane reservoir upon vigorous stirring. The resulting suspension was centrifuged, and separated solid-state residue dried under nitrogen flow to obtain a powder.

e) n-Hexane Anti-Solvent Crystallisation from THF Solution

Approximately 20 mg crude free base were dissolved in 0.5 mL THF, and poured into 4 mL n-Hexane reservoir upon vigorous stirring. The resulting suspension was centrifuged, and separated solid-state residue dried under nitrogen flow to obtain a powder.

f) Cyclohexane Anti-Solvent Crystallisation from THF Solution

Approximately 20 mg crude free base were dissolved in 0.5 mL THF, and poured into 4 mL Cyclohexane reservoir upon vigorous stirring. The resulting suspension was centrifuged, and separated solid-state residue dried under nitrogen flow to obtain a powder.

g) Water Anti-Solvent Crystallisation from DMSO Solution

Approximately 11 mg crude free base were dissolved in 0.5 mL DMSO, and poured into 4 mL Water reservoir upon vigorous stirring. The resulting suspension was centrifuged, and separated solid-state residue dried under nitrogen flow to obtain a powder.

Example 7: Crystallisation Processes of Free Base to Obtain Novel Form NF6 a) n-Heptane Anti-Solvent Crystallisation from Dichloromethane Solution 470 g of 5-(Phenoxy-phenyl)-piperinin-4-ylmethyl-pyrimidine-4,6-diamine was added to a mixture of 10 L dichloromethane and 10 L N,N-dimethylformamide. Subsequently 1 L of N-ethyldiisopropylamine was added to the resulting suspension and stirred for 5 min at 0° C. After that a solution of 105 mL acryloyl chloride in 10 L dichloromethane was added within 8 hours whereas the temperature remained at −5° C. After stirring overnight at 0° C. the reaction mixture was slowly added to chilled deionized water. The organic layer was washed three times with deionized water each, dried over sodium sulfate and evaporated to dryness. The solid residue was triturated with 10 L deionized water for 16 hours. The suspension was filtered and the solid washed again with 10 L deionized water. After drying overnight under vacuum the crude product was dissolved in 2 L dichloromethane and treated slowly under stirring with 5 L n-heptane at 0° C. The solid was filtered off and dried under vacuum until mass consistency.

$^1$H NMR (500 MHz. DMSO-d6) δ 7.96 (s, 1H), 7.43 (dd, J=8.5, 7.5 Hz, 2H), 7.23 (d, J=8.6 Hz, 2H), 7.18 (t, J=7.4 Hz, 1H), 7.15-7.09 (m, 4H), 6.77 (dd, J=16.7, 10.5 Hz, 1H), 6.06 (dd, J=16.7, 2.4 Hz, 1H), 5.63 (dd, J=10.5, 2.4 Hz, 1H), 5.48-5.36 (m, 3H), 4.36 (d, J=12.3 Hz, 1H), 4.00 (d, J=12.9 Hz, 1H), 3.16 (t, J=6.5 Hz, 2H), 2.98 (t, J=12.3 Hz, 1H), 2.59 (t, J=11.9 Hz, 1H), 1.89-1.79 (m, 1H), 1.67-1.56 (m, 2H), 1.04-0.88 (m, 2H).

Example 8: Solubility Data of Free Base Forms a) Kinetic Solubility Data (Approx. 22° C.) of Free Base Forms A1, A2, NF5, NF6

Approximately 5 mg of 1-(4-{[6-Amino-5-(4-phenoxy-phenyl)-pyrimidin-4-ylamino]-methyl}-piperidin-1-yl)-propenone free base (form A1, form A2, form NF5, form NF6) were dispersed in 1-2 mL FaSSIF medium (pH 6.5) in glass vials, and shaken at RT (approx. 22° C.) for defined time intervals (2 h, 4 h) with an overhead shaker. Dispersions were then centrifuged, and clear supernatants were analysed by HPLC for dissolved quantities of 1-(4-{[6-Amino-5-(4-phenoxy-phenyl)-pyrimidin-4-ylamino]-methyl}-piperidin-1-yl)-propenone.

Results from kinetic solubility determinations in FaSSIF are summarised below.

| Form | Kinetic solubility @ 2 h | Kinetic solubility @ 4 h |
| --- | --- | --- |
| Free base form A1 | 27 μg/mL | 28 μg/mL |
| Free base form A2 | 25 μg/mL | n.a. |
| Free base form NF5 | 30 μg/mL | 45 μg/mL |
| Free base form NF6 | 95 μg/mL | 84 μg/mL | b) Thermodynamic Solubility Data (37° C.) of Free Base Forms A1, A2

Approximately 10-20 mg of 1-(4-{[6-Amino-5-(4-phenoxy-phenyl)-pyrimidin-4-ylamino]-methyl}-piperidin-1-yl)-propenone free base (form A1, form A2,) were dispersed in 1-2 mL of FaSSIF medium (pH 6.5) or 1-2 mL of USP Phosphate buffer pH 7.4 in Whatmann Uniprep Syringless Filter (5 mL total volume; 0.45 μm PTFE membrane filter), and agitated at 37° C. for 24 h at 450 rpm using a horizontal shaker in an incubator. Dispersions were then filtrated through internal PTFE membrane from Whatman Uniprep vials, and clear filtrates were analysed by HPLC for dissolved quantities of 1-(4-{[6-Amino-5-(4-phenoxy-phenyl)-pyrimidin-4-ylamino]-methyl}-piperidin-1-yl)-propenone.

Results from thermodynamic solubility determinations are summarised below.

| Form | Thermodynamic solubility FaSSIF pH 6.5 | Thermodynamic solubility PBS buffer 7.4 |
| --- | --- | --- |
| Free base form A1 | 21 μg/mL | 14 μg/mL |
| Free base form A2 | 33 μg/mL | 27 μg/mL |

Example 9: Initial Salt Formation Trials a) HCl Salt Preparations:
i) Experiment from Acetone: Approx. 17.5 mg of free base (as obtained following Example 2) were dissolved in 200 μL Acetone at 50° C., and added with 40.8 μL of 1 N HCl solution. The clear solution was cooled down from 50 C to 5° C. at approx. 0.1 K/min. No crystallisation was observed upon cooling. The solution was further exposed to excess quantities of Diethylether vapour in a closed beaker to induce crystallisation via anti-solvent vapour diffusion, however, no crystallisation was observed upon anti-solvent vapour diffusion.

ii) Experiment from THF:Approx. 19.5 mg of free base (as obtained following Example 2) were dissolved in 200 μL THF at 50° C. and added with 45.3 μL of 1 N HCl solution. The clear solution was cooled down from 50 C to 5° C. at approx. 0.1 K/min. No crystallisation was observed upon cooling. The solution was further exposed to excess quantities of Diethylether vapour in a closed beaker to induce crystallisation via anti-solvent vapour diffusion, however, no crystallisation was observed upon anti-solvent vapour diffusion.

b) Sulfate Salt Preparation:

i) Experiment from Acetone: Approx. 20.6 mg of free base (as obtained following Example 2) were dissolved in 200 μL Acetone at 50° C., and added with 20.6 μL of 98% Sulfuric Acid solution. The clear solution was cooled down from 50 C to 5° C. at approx. 0.1 K/min. No crystallisation was observed upon cooling. The solution was further exposed to excess quantities of Diethylether vapour in a closed beaker to induce crystallisation via anti-solvent vapour diffusion, however, no crystalline solid was obtained upon anti-solvent vapour diffusion.

ii) Experiment from THF:Approx. 19.6 mg of free base (as obtained following Example 2) were dissolved in 200 μL THF at 50° C., and added with 28.2 μL of 98% Sulfuric Acid solution. The clear solution was cooled down from 50 C to 5° C. at approx. 0.1 K/min. No crystallisation was observed upon cooling. The solution was further exposed to excess quantities of Diethylether vapour in a closed beaker to induce crystallisation via anti-solvent vapour diffusion, however, however, no crystalline solid was obtained upon anti-solvent vapour diffusion.

c) Phosphate Salt Preparation:

i) Experiment from Acetone: Approx. 17.7 mg of free base (as obtained following Example 2) were dissolved in 200 μL Acetone at 50° C., and added with 30.6 μL of 85% Phosphoric Acid solution. The clear solution was cooled down from 50 C to 5° C. at approx. 0.1 K/min. No crystallisation was observed upon cooling. The solution was further exposed to excess quantities of Diethylether vapour in a closed beaker to induce crystallisation via anti-solvent vapour diffusion, however, no crystalline solid was obtained upon anti-solvent vapour diffusion.

ii) Experiment from THF:Approx. 20.4 mg of free base (as obtained following Example 2) were dissolved in 200 μL THF at 50° C., and added with 35.2 μL of 85% Phosphoric Acid solution. The clear solution was cooled down from 50 C to 5° C. at approx. 0.1 K/min. No crystallisation was observed upon cooling. The solution was further exposed to excess quantities of Diethylether vapour in a closed beaker to induce crystallisation via anti-solvent vapour diffusion, however, no crystalline solid was obtained upon anti-solvent vapour diffusion.

d) Formiate Salt Preparation:

i) Experiment from Acetone: Approx. 25.5 mg of free base (as obtained following Example 2) were dissolved in 200 μL Acetone at 50° C. and added with 34.2 μL of Formic Acid. The clear solution was cooled down from 50 C to 5° C. at approx. 0.1 K/min. Obtained crystalline solid was identified as free base material as initially used, i.e. no salt formation was achieved.

ii) Experiment from THF:Approx. 24.7 mg of free base (as obtained following Example 2) were dissolved in 200 μL THF at 50° C., and added with 23.8 μL of Formic Acid. The clear solution was cooled down from 50 C to 5° C. at approx. 0.1 K/min. No crystallisation was observed upon cooling. The solution was further exposed to excess quantities of Diethylether vapour in a closed beaker to induce crystallisation via anti-solvent vapour diffusion, however, however, no crystalline solid was obtained upon anti-solvent vapour diffusion.

e) Acetate Salt Preparation:

i) Experiment from Acetone: Approx. 22.2 mg of free base (as obtained following Example 2) were dissolved in 200 μL Acetone at 50° C., and added with 31.1 μL of concentrated Acetic Acid. The clear solution was cooled down from 50 C to 5° C. at approx. 0.1 K/min. Obtained crystalline solid was identified as free base material as initially used, i.e. no salt formation was achieved.

ii) Experiment from THF:Approx. 18.7 mg of free base (as obtained following Example 2) were dissolved in 200 μL THF at 50° C. and added with 27.4 μL of concentrated Acetic Acid. The clear solution was cooled down from 50 C to 5° C. at approx. 0.1 K/min. Obtained crystalline solid was identified as free base material as initially used, i.e. no salt formation was achieved.

f) L-Tartrate Salt Preparation:

i) Experiment from Acetone: Approx. 20.6 mg of free base (as obtained following Example 2) were dissolved in 200 μL Acetone at 50° C., and added with 7.7 mg of L-Tartaric Acid. The clear solution was cooled down from 50 C to 5° C. at approx. 0.1 K/min. No crystallisation was observed upon cooling. The solution was further exposed to excess quantities of Diethylether vapour in a closed beaker to induce crystallisation via anti-solvent vapour diffusion, however, however, no crystalline solid was obtained upon anti-solvent vapour diffusion.

ii) Experiment from THF:Approx. 18.2 mg of free base (as obtained following Example 2) were dissolved in 200 μL THF at 50° C. and added with 6.3 mg of L-Tartaric Acid. The clear solution was cooled down from 50 C to 5° C. at approx. 0.1 K/min. No crystallisation was observed upon cooling. The solution was further exposed to excess quantities of Diethylether vapour in a closed beaker to induce crystallisation via anti-solvent vapour diffusion, however, no crystalline solid was obtained upon anti-solvent vapour diffusion.

g) Benzoate Salt Preparation:

i) Experiment from THF:Approx. 17.9 mg of free base (as obtained following Example 2) were dissolved in 200 μL THF at 50° C. and added with 5.1 mg of Benzoic Acid. The clear solution was cooled down from 50 C to 5° C. at approx. 0.1 K/min. No crystallisation was observed upon cooling. The solution was further exposed to excess quantities of Diethylether vapour in a closed beaker to induce crystallisation via anti-solvent vapour diffusion. Obtained crystalline solid was identified as free base material as initially used, i.e. no salt formation was achieved.

h) S-Glutamate Salt Preparation:

i) Experiment from THF:Approx. 18.6 mg of free base (as obtained following Example 2) were dissolved in 200 μL THF at 50° C., and added with 6.6 mg of S-Glutamic Acid. The clear solution was cooled down from 50 C to 5° C. at approx. 0.1 K/min. No crystallisation was observed upon cooling. The solution was further exposed to excess quantities of Diethylether vapour in a closed beaker to induce crystallisation via anti-solvent vapour diffusion. Obtained crystalline solid was identified as free base material as initially used, i.e. no salt formation was achieved.

Example 10: Preparation Processes for Novel Salt Forms a) Malonate Salt (Malonate-NF1) Preparations:
i) Experiment from Acetone: Approximately 24.6 mg of free base (as obtained following Example 2) were dissolved in 200 μL Acetone at 50° C., and added with 6.0 mg of Malonic Acid. The clear solution was cooled down from 50 C to 5° C. at approximately 0.1 K/min. No crystallisation was observed upon cooling. The solution was further exposed to excess quantities of Diethylether vapour in a closed beaker to induce crystallisation via anti-solvent vapour diffusion. Obtained crystals after vapour diffusion were separated from mother liquor by vacuum suction.

$^1$H NMR (500 MHz. DMSO-d6) δ 13.07 (s br, 2H), 8.01 (s, 1H), 7.47-7.39 (m, 2H), 7.24 (d, J=8.6 Hz, 2H), 7.18 (t, J=7.4 Hz, 1H), 7.15-7.10 (m, 4H), 6.77 (dd, J=16.7, 10.5 Hz, 1H), 6.06 (dd, J=16.7, 2.4 Hz, 1H), 5.69-5.58 (m, 4H), 4.36 (d, J=12.3 Hz, 1H), 4.00 (d, J=12.9 Hz, 1H), 3.19-3.14 (m, 4H), 2.98 (t, J=12.3 Hz, 1H), 2.58 (t, J=11.8 Hz, 1H), 1.89-1.78 (m, 1H), 1.66-1.56 (m, 2H), 1.03-0.88 (m, 2H).

ii) Experiment from THF: Approximately 21.9 mg of free base (as obtained following Example 2) were dissolved in 200 μL THF at 50° C. and added with 5.7 mg of Malonic Acid. The clear solution was cooled down from 50 C to 5° C. at approx. 0.1 K/min. No crystallisation was observed upon cooling. The solution was further exposed to excess quantities of Diethylether vapour in a closed beaker to induce crystallisation via anti-solvent vapour diffusion. Obtained crystals after vapour diffusion were separated from mother liquor by vacuum suction.

iii) Upscale experiment from Acetone: Approximately 103.8 mg of free base (as obtained following Example 2) were dissolved in 1 mL Acetone at 50° C. and added with 25.3 mg of Malonic Acid. The clear solution was cooled down from 50 C to 5° C. at approx. 0.1 K/min. No crystallisation was observed upon cooling. The solution was further exposed to excess quantities of Diethylether vapour in a closed beaker to induce crystallisation via anti-solvent vapour diffusion. Obtained crystals after vapour diffusion were separated from mother liquor by vacuum suction.

$^1$H NMR (500 MHz. DMSO-d6) δ 13.03 (s br, 2H), 8.00 (s, 1H), 7.42 (dd, J=8.5, 7.5 Hz, 2H), 7.22 (d, J=8.7 Hz, 2H), 7.17 (tt, J=7.5, 1.0 Hz, 1H), 7.14-7.09 (m, 4H), 6.76 (dd, J=16.7, 10.5 Hz, 1H), 6.05 (dd, J=16.7, 2.4 Hz, 1H), 5.69-5.55 (m, 4H), 4.35 (d, J=12.2 Hz, 1H), 3.99 (d, J=12.8 Hz, 1H), 3.20-3.11 (m, 4H), 2.97 (t, J=12.3 Hz, 1H), 2.57 (t, J=11.8 Hz, 1H), 1.88-1.77 (m, 1H), 1.66-1.54 (m, 2H), 1.02-0.85 (m, 2H).

b) Succinate Salt (Succinate-NF1) Preparations:
i) Experiment from Acetone: Approximately 27.6 mg of free base (as obtained following Example 2) were dissolved in 200 μL Acetone at 50° C. and added with 12.9 mg of Succinic Acid. The clear solution was cooled down from 50 C to 5° C. at approx. 0.1 K/min. No crystallisation was observed upon cooling. The solution was further exposed to excess quantities of Diethylether vapour in a closed beaker to induce crystallisation via anti-solvent vapour diffusion. Obtained crystals after vapour diffusion were separated from mother liquor by vacuum suction.

$^1$H NMR (500 MHz, DMSO-d6) δ 12.19 (s, 2H), 7.96 (s, 1H), 7.43 (dd, J=8.5, 7.5 Hz, 2H), 7.23 (d, J=8.6 Hz, 2H), 7.18 (t, J=7.4 Hz, 1H), 7.14-7.10 (m, 4H), 6.77 (dd, J=16.7, 10.5 Hz, 1H), 6.06 (dd, J=16.7, 2.4 Hz, 1H), 5.63 (dd, J=10.5, 2.4 Hz, 1H), 5.46-5.39 (m, 3H), 4.36 (d, J=12.2 Hz, 1H), 4.00 (d, J=13.1 Hz, 1H), 3.15 (t, J=6.5 Hz, 2H), 2.98 (t, J=12.3 Hz, 1H), 2.58 (t, J=12.0 Hz, 1H), 2.43 (s, 5H), 1.89-1.78 (m, 1H), 1.67-1.57 (m, 2H), 1.03-0.86 (m, 2H).

ii) Upscale experiment from Acetone: Approximately 103.9 mg of free base (as obtained following Example 2) were dissolved in 1 mL Acetone at 50° C. and added with 29.5 mg of Succinic Acid. The clear solution was cooled down from 50 C to 5° C. at approx. 0.1 K/min. No crystallisation was observed upon cooling. The solution was further exposed to excess quantities of Diethylether vapour in a closed beaker to induce crystallisation via anti-solvent vapour diffusion. Obtained crystals after vapour diffusion were separated from mother liquor by vacuum suction.

$^1$H NMR (500 MHz. DMSO-d6) δ 12.19 (s br, 2H), 7.94 (s, 1H), 7.42 (dd, J=8.6, 7.4 Hz, 2H), 7.22 (d, J=8.7 Hz, 2H), 7.16 (tt, J=7.5, 1.0 Hz, 1H), 7.13-7.08 (m, 4H), 6.76 (dd, J=16.7, 10.5 Hz, 1H), 6.05 (dd, J=16.7, 2.4 Hz, 1H), 5.62 (dd, J=10.5, 2.4 Hz, 1H), 5.45-5.36 (m, 3H), 4.35 (d, J=12.3 Hz, 1H), 3.99 (d, J=12.9 Hz, 1H), 3.14 (t, J=6.5 Hz, 2H), 2.97 (t, J=12.4 Hz, 1H), 2.57 (t, J=11.8 Hz, 1H), 2.41 (s, 4H), 1.88-1.76 (m, 1H), 1.65-1.55 (m, 2H), 1.01-0.87 (m, 2H).

c) Oxalate Salt (Oxalate-NF1) Preparations:
i) Experiment from Acetone: Approximately 17.0 mg of free base (as obtained following Example 2) were dissolved in 200 μL Acetone at 50° C., and added with 5.1 mg of Oxalic Acid (dihydrate). The clear solution was cooled down from 50 C to 5° C. at approx. 0.1 K/min. Obtained crystals after cooling were separated from mother liquor by vacuum suction.

$^1$H NMR (500 MHz, DMSO-d6) δ 8.14 (s, 1H), 7.44 (dd, J=8.5, 7.5 Hz, 2H), 7.26 (d, J=8.6 Hz, 2H), 7.19 (t, J=7.4 Hz, 1H), 7.16-7.11 (m, 4H), 6.77 (dd, J=16.7, 10.5 Hz, 1H), 6.28 (s, 2H), 6.15 (t, J=5.9 Hz, 1H), 6.06 (dd, J=16.7, 2.4 Hz, 1H), 5.63 (dd, J=10.5, 2.4 Hz, 1H), 4.36 (d, J=12.3 Hz, 1H), 4.00 (d, J=12.9 Hz, 1H), 3.20 (t, J=6.5 Hz, 2H), 2.98 (t, J=12.3 Hz, 1H), 2.59 (t, J=11.9 Hz, 1H), 1.89-1.79 (m, 1H), 1.66-1.57 (m, 2H), 1.03-0.90 (m, 2H). $^{13}$C NMR (126 MHz, DMSO-d6) δ 164.1, 162.8, 159.4, 156.6, 156.5, 156.4, 152.7, 132.3, 130.0, 128.6, 126.7, 126.1, 123.6, 119.9, 118.8, 45.6, 44.9, 41.3, 35.7, 30.3, 29.2.

ii) Experiment from THF: Approximately 16.9 mg of free base (as obtained following Example 2) were dissolved in 200 μL THF at 50° C., and added with 4.9 mg of Oxalic Acid (dihydrate). The clear solution was cooled down from 50 C to 5° C. at approx. 0.1 K/min. Obtained crystals after cooling were separated from mother liquor by vacuum suction.

iii) Upscale experiment from Acetone: Approximately 99.6 mg of free base (as obtained following Example 2) were dissolved in 1 mL Acetone at 50° C., and added with 29.0 mg of Oxalic Acid (dihydrate). The clear solution was cooled down from 50 C to 5° C. at approx. 0.1 K/min. Obtained crystals after cooling were separated from mother liquor by vacuum suction.

$^1$H NMR (500 MHz, DMSO-d6) S 8.12 (s, 1H), 7.43 (dd, J=8.5, 7.5 Hz, 2H), 7.24 (d, J=8.6 Hz, 2H), 7.18 (t, J=7.4 Hz, 1H), 7.15-7.09 (m, 4H), 6.76 (dd, J=16.7, 10.5 Hz, 1H), 6.26 (s, 2H), 6.13 (t, J=5.9 Hz, 1H), 6.05 (dd, J=16.7, 2.4 Hz, 1H), 5.62 (dd, J=10.5, 2.4 Hz, 1H), 4.35 (d, J=12.2 Hz, 1H), 3.99 (d, J=13.0 Hz, 1H), 3.19 (t, J=6.5 Hz, 2H), 2.97 (t, J=12.3 Hz, 1H), 2.58 (t, J=12.0 Hz, 1H), 1.88-1.77 (m, 1H), 1.66-1.56 (m, 2H), 1.03-0.88 (m, 2H). $^{13}$C NMR (126 MHz. DMSO-d6) δ 164.1, 162.8, 159.4, 156.6, 156.4, 152.8, 132.3, 130.0, 128.6, 126.7, 126.1, 123.6, 119.9, 118.9, 45.6, 45.0, 41.4, 35.7, 30.3, 29.2.

d) Fumarate Salt (Fumarate-NF1) Preparations:
i) Experiment from Acetone: Approximately 18.9 mg of free base (as obtained following Example 2) were dissolved in 200 μL Acetone at 50° C. and added with 5.0 mg of Fumaric Acid. The clear solution was cooled down from 50 C to 5° C. at approx. 0.1 K/min. Obtained crystals after cooling were separated from mother liquor by vacuum suction.

$^1$H NMR (500 MHz, DMSO-d6) δ 13.13 (s br, 2H), 7.97 (s, 1H), 7.43 (dd, J=8.5, 7.5 Hz, 2H), 7.23 (d, J=8.6 Hz, 2H), 7.18 (t, J=7.4 Hz, 1H), 7.14-7.08 (m, 4H), 6.77 (dd, J=16.7, 10.5 Hz, 1H), 6.63 (s, 2H), 6.06 (dd, J=16.7, 2.4 Hz, 1H), 5.63 (dd, J=10.5, 2.4 Hz, 1H), 5.51-5.39 (m, 3H), 4.36 (d, J=12.3 Hz, 1H), 4.00 (d, J=12.9 Hz, 1H), 3.15 (t, J=6.5 Hz, 2H), 2.98 (t, J=12.3 Hz, 1H), 2.58 (t, J=11.9 Hz, 1H), 1.89-1.78 (m, 1H), 1.66-1.56 (m, 2H), 1.03-0.87 (m, 2H).

ii) Experiment from THF: Approximately 19.5 mg of free base (as obtained following Example 2) were dissolved in 200 μL THF at 50° C. and added with 5.7 mg of Fumaric Acid. The clear solution was cooled down from 50 C to 5° C. at approx. 0.1 K/min. Obtained crystals after cooling were separated from mother liquor by vacuum suction.

iii) Upscale experiment from Acetone: Approximately 131.8 mg of free base (as obtained following Example 2) were dissolved in 1 mL Acetone at 50° C. and added with 39.0 mg of Fumaric Acid. The clear solution was cooled down from 50 C to 5° C. at approx. 0.1 K/min. Obtained crystals after cooling were separated from mother liquor by vacuum suction.

$^1$H NMR (500 MHz, DMSO-d6) δ 13.07 (s br, 1H), 7.95 (s, 1H), 7.42 (dd, J=8.5, 7.5 Hz, 2H), 7.22 (d, J=8.6 Hz, 2H), 7.16 (t, J=7.4 Hz, 1H), 7.13-7.09 (m, 4H), 6.76 (dd, J=16.7, 10.5 Hz, 1H), 6.62 (s, 2H), 6.05 (dd, J=16.7, 2.4 Hz, 1H), 5.62 (dd, J=10.5, 2.4 Hz, 1H), 5.48-5.40 (m, 3H), 4.35 (d, J=12.4 Hz, 1H), 3.99 (d, J=13.1 Hz, 1H), 3.14 (t, J=6.5 Hz, 2H), 2.97 (t, J=12.4 Hz, 1H), 2.57 (t, J=12.0 Hz, 1H), 1.88-1.78 (m, 1H), 1.66-1.54 (m, 2H), 1.02-0.87 (m, 2H).

e) Maleate Salt (Maleate-NF1) Preparations:
i) Experiment from Acetone: Approximately 23.8 mg of free base (as obtained following Example 2) were dissolved in 200 μL Acetone at 50° C., and added with 6.5 mg of Maleic Acid. The clear solution was cooled down from 50° C. to 5° C. at approx. 0.1 K/min. Obtained crystals after cooling were separated from mother liquor by vacuum suction.

$^1$H NMR (500 MHz, DMSO-d6): δ 15.29 (s br, 1H), 8.22 (s, 1H), 7.45 (dd, J=8.5.7.5 Hz, 2H), 7.26 (d, J=8.7 Hz, 2H), 7.20 (t, J=7.4 Hz, 1H), 7.17-7.12 (m, 4H), 6.78 (dd, J=16.7, 10.5 Hz, 1H), 6.55 (t, J=6.0 Hz, 1H), 6.42 (s, 2H), 6.11 (s, 2H), 6.07 (dd, J=16.7, 2.4 Hz, 1H), 5.64 (dd, J=10.5, 2.4 Hz, 1H), 4.37 (d, J=12.2 Hz, 1H), 4.01 (d, J=13.0 Hz, 1H), 3.21 (t, J=6.6 Hz, 2H), 2.98 (t, J=12.3 Hz, 1H), 2.59 (t, J=11.9 Hz, 1H), 1.89-1.78 (m, 1H), 1.67-1.55 (m, 2H), 1.05-0.89 (m, 2H).

ii) Experiment from THF: Approximately 19.9 mg of free base (as obtained following Example 2) were dissolved in 200 μL THF at 50° C., and added with 5.3 mg of Maleic Acid. The clear solution was cooled down from 50° C. to 5° C. at approx. 0.1 K/min. Obtained crystals after cooling were separated from mother liquor by vacuum suction.

iii) Upscale experiment from Acetone: Approximately 119.9 mg of free base (as obtained following Example 2) were dissolved in 1 mL Acetone at 50° C., and added with 32.4 mg of Maleic Acid. The clear solution was cooled down from 50 C to 5° C. at approx. 0.1 K/min. Obtained crystals after cooling were separated from mother liquor by vacuum suction.

$^1$H NMR (500 MHz, DMSO-d6) δ 15.20 (s br, 1H), 8.21 (s, 1H), 7.44 (dd, J=8.5, 7.5 Hz, 2H), 7.25 (d, J=8.7 Hz, 2H), 7.19 (t, J=7.4 Hz, 1H), 7.16-7.10 (m, 4H), 6.76 (dd, J=16.7, 10.5 Hz, 1H), 6.55 (t, J=6.1 Hz, 1H), 6.41 (s, 2H), 6.09 (s, 2H), 6.05 (dd, J=16.7, 2.4 Hz, 1H), 5.63 (dd, J=10.5, 2.4 Hz, 1H), 4.36 (d, J=12.3 Hz, 1H), 4.00 (d, J=13.0 Hz, 1H), 3.20 (t, J=6.6 Hz, 2H), 2.97 (t, J=12.4 Hz, 1H), 2.57 (t, J=11.9 Hz, 1H), 1.87-1.77 (m, 1H), 1.66-1.56 (m, 2H), 1.03-0.89 (m, 2H).

f) Citrate Salt (Citrate-NF1) Preparations:
i) Experiment from Acetone: Approximately 23.2 mg of free base (as obtained following Example 2) were dissolved in 200 μL Acetone at 50° C. and added with 10.5 mg of Citric Acid. The clear solution was cooled down from 50° C. to 5° C. at approx. 0.1 K/min. Obtained crystals after cooling were separated from mother liquor by vacuum suction.

$^1$H NMR (500 MHz, DMSO-d6) δ 11.10 (s br, 2H), 8.01 (s, 1H), 7.43 (dd, J=8.5, 7.5 Hz, 2H), 7.23 (d, J=8.6 Hz, 2H), 7.18 (t, J=7.4 Hz, 1H), 7.15-7.10 (m, 4H), 6.77 (dd, J=16.7, 10.5 Hz, 1H), 6.06 (dd, J=16.7, 2.4 Hz, 1H), 5.67-5.56 (m, 4H), 4.36 (d, J=12.2 Hz, 1H), 4.00 (d, J=12.7 Hz, 1H), 3.16 (t, J=6.5 Hz, 2H), 2.98 (t, J=12.4 Hz, 1H), 2.74 (d, J=15.3 Hz, 2H), 2.64 (d, J=15.4 Hz, 2H), 2.59 (t, J=12.2 Hz, 1H), 1.89-1.78 (m, 1H), 1.66-1.56 (m, 2H), 1.03-0.88 (m, 2H).

Example 11: Mini-Dissolution Data of Novel Salt Forms Vs Parent

Approximately 5 mg of 1-(4-{[6-Amino-5-(4-phenoxy-phenyl)-pyrimidin-4-ylamino]-methyl}-piperidin-1-yl)-propenone free base (form A1), and respective Malonate salt (form Malonate-NF1), Succinate salt (form Succinate-NF1), and Oxalate salt (form Oxalate-NF1) were weighed into 12 mL glass vials, and dispersed in 7 mL FaSSIF medium (pH 6.5) or FeSSIF medium (pH 5.0), respectively.

All dispersions were agitated at 37° C. for up to 2 hours. At defined time intervals (30 min. 60 min, 120 min), sample aliquots of homogeneous dispersions were withdrawn by a syringe, and filtrated via syringe filter adapters (PTFE, 0.45 μm). Clear filtrates were analysed by HPLC for dissolved quantities of 1-(4-{[6-Amino-5-(4-phenoxy-phenyl)-pyrimidin-4-ylamino]-methyl}-piperidin-1-yl)-propenone free base.

Results from mini dissolution studies are summarised below.

| | Dissolution levels in FaSSIF pH 6.5 (μg/mL) | | | |
|---|---|---|---|---|
| Time | Free base form A1 | Malonate-NF1 | Succinate-NF1 | Oxalate-NF1 |
| 30 min | 25 | 47 | 92 | 50 |
| 60 min | 33 | 53 | 95 | 54 |
| 120 min | 36 | 75 | 100 | 58 |

| | Dissolution levels in FeSSIF pH 5.0 (μg/mL) | | | |
|---|---|---|---|---|
| Time | Free base form A1 | Malonate-NF1 | Succinate-NF1 | Oxalate-NF1 |
| 30 min | 190 | 651 | 625 | 600 |
| 60 min | 205 | 694 | 708 | 700 |
| 120 min | 214 | 740 | 743 | 740 |

While a number of embodiments of this invention are described herein, it is apparent that the basic examples may be altered to provide other embodiments that utilize the compounds and methods of this invention. Therefore, it will be appreciated that the scope of this invention is to be defined by the appended claims rather than by the specific embodiments that have been represented by way of example.

We claim:
1. A solid form of compound 1,

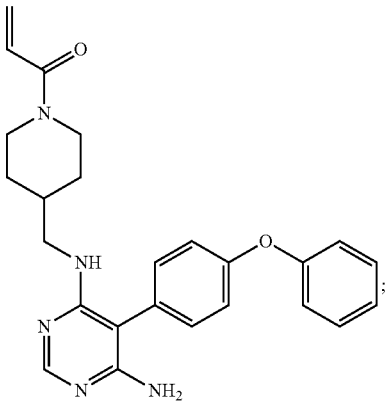

wherein said solid form is a crystalline form A2,
wherein said form A2 is characterized by a crystal form, having a monoclinic space group $P2_1$ with the lattice parameters (at 200 K) a=9.4±0.1 Å, b=37.2±0.2 Å, c=12.8±0.1 Å, and β=91.9±0.5° (with α=γ=90°).

2. The solid form of claim 1, characterized as a mixture of crystalline forms A1 and A2; wherein said crystalline form A1 is characterized by a crystal form, having a monoclinic space group $P2_1$ with the lattice parameters (at 200 K) a=12.8±0.1 Å, b 9.4±0.1 Å, c=37.3±0.2 Å, and β=98.5±0.5° (with α=γ=90°).

3. A pharmaceutical composition, comprising:
   the solid form of compound 1 of claim 1, and
   a pharmaceutically acceptable adjuvant, carrier, or vehicle.

4. A method for treating a BTK-mediated disorder in a patient in thereof, comprising:
   administering to said patient a solid form of compound 1 of claim 1;
   wherein said BTK-mediated disorder is systemic lupus erythematosus (SLE), multiple sclerosis, or rheumatoid arthritis.

5. A pharmaceutical composition, comprising:
   a solid form of compound 1 of claim 2, and
   a pharmaceutically acceptable adjuvant, carrier, or vehicle.

6. A method for treating a BTK-mediated disorder in a patient in need thereof, comprising:
   administering to said patient a solid form of compound 1 of claim 2;
   wherein said BTK-mediated disorder is systemic lupus erythematosus (SLE), multiple sclerosis, or rheumatoid arthritis.

* * * * *